(12) United States Patent
Murphy et al.

(10) Patent No.: US 12,083,245 B2
(45) Date of Patent: Sep. 10, 2024

(54) AMNIOTIC MEMBRANE POWDER AND ITS USE IN WOUND HEALING AND TISSUE ENGINEERING CONSTRUCTS

(71) Applicant: WAKE FOREST UNIVERSITY HEALTH SCIENCES, Winston-Salem, NC (US)

(72) Inventors: Sean V. Murphy, Winston-Salem, NC (US); Aleksander Skardal, Clemmons, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 6 days.

(21) Appl. No.: 15/515,049

(22) PCT Filed: Oct. 1, 2015

(86) PCT No.: PCT/US2015/053571
§ 371 (c)(1),
(2) Date: Mar. 28, 2017

(87) PCT Pub. No.: WO2016/054423
PCT Pub. Date: Apr. 7, 2016

(65) Prior Publication Data
US 2017/0203004 A1    Jul. 20, 2017

Related U.S. Application Data

(60) Provisional application No. 62/058,969, filed on Oct. 2, 2014.

(51) Int. Cl.
| | |
|---|---|
| *A61L 27/36* | (2006.01) |
| *A61K 31/726* | (2006.01) |
| *A61K 35/50* | (2015.01) |
| *A61K 38/17* | (2006.01) |
| *A61K 38/36* | (2006.01) |
| *A61K 38/39* | (2006.01) |
| *A61L 26/00* | (2006.01) |
| *A61L 27/20* | (2006.01) |
| *A61L 27/22* | (2006.01) |
| *A61L 27/24* | (2006.01) |
| *A61L 27/26* | (2006.01) |
| *A61L 27/52* | (2006.01) |
| *A61L 27/54* | (2006.01) |
| *A61L 27/60* | (2006.01) |

(52) U.S. Cl.
CPC ........ *A61L 27/3604* (2013.01); *A61K 31/726* (2013.01); *A61K 35/50* (2013.01); *A61K 38/177* (2013.01); *A61K 38/36* (2013.01); *A61K 38/39* (2013.01); *A61L 26/0057* (2013.01); *A61L 26/008* (2013.01); *A61L 27/20* (2013.01); *A61L 27/222* (2013.01); *A61L 27/227* (2013.01); *A61L 27/24* (2013.01); *A61L 27/26* (2013.01); *A61L 27/3641* (2013.01); *A61L 27/3683* (2013.01); *A61L 27/52* (2013.01); *A61L 27/54* (2013.01); *A61L 27/60* (2013.01); *A61L 2300/236* (2013.01); *A61L 2300/252* (2013.01); *A61L 2300/412* (2013.01); *A61L 2430/34* (2013.01)

(58) Field of Classification Search
None
See application file for complete search history.

(56) References Cited

U.S. PATENT DOCUMENTS

| | | |
|---|---|---|
| 4,001,944 A | 1/1977 | Williams |
| 5,514,378 A | 5/1996 | Mikos et al. |
| 6,323,219 B1 | 11/2001 | Costanzo |
| 6,350,463 B1 | 2/2002 | Herman et al. |
| 7,871,646 B2 | 1/2011 | Ghinelli et al. |
| 7,968,085 B2 | 6/2011 | Hersel et al. |
| 8,821,857 B2 | 9/2014 | Bhatia et al. |
| 8,932,805 B1 | 1/2015 | Brahm et al. |
| 9,198,939 B2 | 12/2015 | Tseng et al. |
| 9,526,770 B2 | 12/2016 | Tseng et al. |
| 9,585,983 B1 | 3/2017 | Brahm et al. |
| 10,016,464 B2 | 7/2018 | Murphy et al. |
| 10,967,009 B2 | 4/2021 | Murphy et al. |
| 2004/0048796 A1 | 3/2004 | Hariri et al. |
| 2004/0048798 A1 | 3/2004 | Raitano et al. |
| 2005/0220848 A1 | 10/2005 | Bates |

(Continued)

FOREIGN PATENT DOCUMENTS

| | | |
|---|---|---|
| EP | 2708226 A1 | 3/2014 |
| JP | 2012517235 A | 8/2012 |

(Continued)

OTHER PUBLICATIONS

Kharkar et al. (Chem Soc Rev. Aug. 5, 2013; 42(17): 7335-7372) (Year: 2013).*
Camci-Unal et al. (Biomacromolecules 2013, 14, 1085-1092) (Year: 2013).*
Vanderhooft et al. (Biomacromolecules. Sep. 2007;8(9):2883-9) (Year: 2007).*
Wilshaw et al. (Tissue Eng. Aug. 2006;12(8):2117-29) (Year: 2006).*
Extended European Search Report for European Patent Application No. 15847740.6 issued May 4, 2018.

(Continued)

*Primary Examiner* — Sergio Coffa
(74) *Attorney, Agent, or Firm* — Saul Ewing LLP; Kathryn Doyle; Justin Crotty

(57) ABSTRACT

The present invention includes compositions and methods for wound healing and tissue regeneration. The compositions of the present invention comprise amniotic membrane powder. The compositions of the present invention comprise amniotic membrane powder and a scaffold. The methods of the present invention comprises applying a composition of the present invention to a subject to induce wound healing and tissue regeneration.

25 Claims, 45 Drawing Sheets

(56) References Cited

U.S. PATENT DOCUMENTS

| | | | |
|---|---|---|---|
| 2007/0003525 | A1 | 1/2007 | Moehlenbruck et al. |
| 2007/0071740 | A1 | 3/2007 | Tseng et al. |
| 2008/0039940 | A1 | 2/2008 | Hashimoto et al. |
| 2008/0108045 | A1 | 5/2008 | Ghinelli et al. |
| 2008/0306455 | A1 | 12/2008 | Dias et al. |
| 2009/0280182 | A1 | 11/2009 | Beck et al. |
| 2010/0055184 | A1 | 3/2010 | Zeitels et al. |
| 2010/0254900 | A1 | 10/2010 | Campbell et al. |
| 2011/0189301 | A1 | 8/2011 | Yang et al. |
| 2011/0206645 | A1 | 8/2011 | Zhang et al. |
| 2011/0206776 | A1 | 8/2011 | Tom et al. |
| 2011/0219462 | A1 | 9/2011 | Delbeck et al. |
| 2012/0077272 | A1 | 3/2012 | Kharazi et al. |
| 2012/0078378 | A1 | 3/2012 | Daniel et al. |
| 2012/0189583 | A1 | 7/2012 | Liu et al. |
| 2013/0006385 | A1 | 1/2013 | Daniel et al. |
| 2013/0202676 | A1 | 8/2013 | Koob et al. |
| 2013/0210760 | A1 | 8/2013 | Liu et al. |
| 2013/0230561 | A1 | 9/2013 | Daniel et al. |
| 2013/0280344 | A1* | 10/2013 | Tseng .................. A61K 35/50 424/583 |
| 2014/0051059 | A1 | 2/2014 | Pringle et al. |
| 2014/0106447 | A1 | 4/2014 | Brown et al. |
| 2014/0147511 | A1 | 5/2014 | Tseng et al. |
| 2014/0342015 | A1 | 11/2014 | Murphy et al. |
| 2015/0342998 | A1 | 12/2015 | Tseng et al. |
| 2016/0120912 | A1 | 5/2016 | Tseng |
| 2016/0199417 | A1 | 7/2016 | Werber et al. |
| 2016/0339061 | A1 | 11/2016 | Tseng et al. |

FOREIGN PATENT DOCUMENTS

| | | | |
|---|---|---|---|
| JP | 2013536737 | A | 9/2013 |
| WO | 0041732 | A1 | 7/2000 |
| WO | 03024496 | A1 | 3/2003 |
| WO | 2006094247 | A2 | 9/2006 |
| WO | 2007038686 | A2 | 4/2007 |
| WO | 2012170905 | A1 | 12/2012 |
| WO | WO 2012/170905 | * | 12/2012 |
| WO | 2013032938 | A1 | 3/2013 |
| WO | 2013114132 | A1 | 8/2013 |
| WO | 2014040026 | A2 | 3/2014 |
| WO | WO 2014/089440 | * | 6/2014 |
| WO | 2016040385 | A1 | 3/2016 |

OTHER PUBLICATIONS

Vanderhooft, et al., "Synthesis and Characterization of Novel Thiol-Reactive Poly(ethylene glycol) Cross-Linkers for Extracellular-Matrix-Mimetic Biomaterials", Biomacromolecules 8, 2007, 2883-2889.
PCT International Search Report and Written Opinion for PCT International Application No. PCT/US2015/053571 issued Dec. 28, 2015.
Thermo Scientific: Thermo Scientific Hycolne Hystem Hydrogels; Product Packet, Cell Culture & BioProcessing, Logan, UT, 2008, 6 pages.
ESI BIO: Hystem-C Hydrogels; Online URL <http://www.esibio.com/hystem-c-hydrogels/>, Accessed Apr. 27, 2016, 3 pages.
Atala, et al., "Formation of urothelial structures in vivo from dissociated cells attached to biodegradable polymer scaffolds in vitro", J Urol. 148(2 Pt 2), 1992, 658-662.
Atala, et al., "Implantation in vivo and retrieval of artificial structures consisting of rabbit and human urothelium and human bladder muscle", J Urol. 150(2 Pt 2), 1993, 608-612.
Brannon-Peppas, "Preparation and Characterization of Cross-linked Hydrophilic Networks", Absorbent Polymer Technology, Brannon-Peppas and Harland, Eds. 1990, Elsevier: Amsterdam, pp. 45-66.
Burdick, et al., "Hyaluronic acid hydrogels for biomedical applications", Adv Mater. 23(12), Mar. 25, 2011, H41-56, 1-31.
Cherry, et al., "National Ambulatory Medical Care Survey: 2006 summary", Natl Health Stat Report (3), 2008, 1-39.
Cock, et al., "Pulmonary elastin synthesis and deposition in developing and mature sheep: effects of intrauterine growth restriction", Exp Lung Res. 30(5), 2004, 405-418.
Fedorovich, et al., "Hydrogels as extracellular matrices for skeletal tissue engineering: state-of-the-art and novel application in organ printing", Tissue Eng. 13(8), 2007, 1905-1925.
Hennink, et al., "Novel crosslinking methods to design hydrogels", Adv. Drug Del. Rev. 54, 2002, 13-36.
Hill-West, et al., "Inhibition of thrombosis and intimal thickening by in situ photopolymerization of thin hydrogel barriers", Proc Natl Acad Sci U S A. 91(13), Jun. 21, 1994, 5967-5971.
Hoffman, "Hydrogels for biomedical applications", Adv. Drug Del. Rev. 43, 2002, 3-12.
Hussin, et al., "The Fabrication of Human Amniotic Membrane Based Hydrogel for Cartilage Tissue Engineering Applications: A Preliminary Study", Biomed. IFMBE Proceedings 35, 2011, 841-844.
Hwang, et al., "Chondrogenic Differentiation of Human Embryonic Stem Cell-Derived Cells in Arginine-Glycine-Aspartate-Modified Hydrogels", Tissue Eng. 12, 2006, 26952-706.
Ifkovits, et al., "Review: Photopolymerizable and Degradable Biomaterials for Tissue Engineering Applications", Tissue Eng. 13(10), 2007, 2369-2385.
Katta, et al., "Continuous Electrospinning of Aligned Polymer Nanofibers onto a Wire Drum Collector", Nano Letters 4(11), 2004, 2215-2218.
Kim, et al., "Control of degradation rate and hydrophilicity in electrospun non-woven poly(D,L-lactide) nanofiber scaffolds for biomedical application", Biomaterials. 24(27), 2003, 4977-4985.
Kurd, et al., "Evaluation of the use of prognostic information for the care of individuals with venous leg ulcers or diabetic neuropathic foot ulcers", Wound Repair Regen. 17(3), 2009, 318-325.
Lesher, et al., "Effectiveness of Biobrane for treatment of partial-thickness burns in children", J Pediatr Surg. 46(9), 2011, 1759-1763.
Li, et al., "Collecting Electrospun Nanofibers with Patterned Electrodes", Nano Lett. 5(5), 2005, 913-916.
Li, et al., "Human placenta-derived adherent cells prevent bone loss, stimulate bone formation, and suppress growth of multiple myeloma in bone", Stem Cells. 29(2), Feb. 2011, 263-273.
Miller, et al., "National burn repository 2007 report: a synopsis of the 2007 call for data", J Burn Care Res. 29(6), 2008, 862-870.
Mironov, et al., "Organ printing: computer-aided jet-based 3D tissue engineering", Trends Biotechnol. 21(4), 2003, 157-161.
Nguyen, et al., "Photopolymerizable hydrogels for tissue engineering applications", Biomaterials 23(22), 2002, 4307-4314.
Peck, "Epidemiology of burns throughout the world. Part I: Distribution and risk factors", Burns. 37(7), 2011, 1087-1100.
Peppas, et al., "Preparation Methods and Structure of Hydrogels", Hydrogels in Medicine and Pharmacy, Peppas, Ed. 1986, CRC Press: Boca Raton, Florida, pp. 1-27.
Pitts, et al., "National Hospital Ambulatory Medical Care Survey: 2006 emergency department summar", Natl Health Stat Report.(7), 2008, 1-38.
Rahmanian-Schwarz, et al., "A clinical evaluation of Biobrane(®) and Suprathel(®) in acute burns and reconstructive surgery", Burns. 37(8), 2011, 1343-1348.
Ratner, et al., "Synthetic Hydrogels for Biomedical Applications", Hydrogels for Medical and Related Applications, Andrade Ed. American Chemical Society: Washington, D.C., 1976, 1-36.
Reading, et al., "Antiviral activity of the long chain pentraxin PTX3 against influenza viruses", J Immunol. 180(5), 2008, 3391-3398.
Rosen, et al., "Artificial nerve graft using collagen as an extracellular matrix for nerve repair compared with sutured autograft in a rat model", Ann Plast Surg. 25(5), 1990, 375-387.
Sen, et al., "Human skin wounds: a major and snowballing threat to public health and the economy", Wound Repair Regen. 17(6), 2009, 763-771.
Serban, et al., "Synthesis, characterization and chondroprotective properties of a hyaluronan thioethyl ether derivative", Biomaterials. 29(10), 2008, 1388-1399.
Shin, "Biomimetic materials for tissue engineering", Biomaterials 24, 2003, 4353-4364.

(56) References Cited

OTHER PUBLICATIONS

Vanderhooft, et al., "Rheological properties of cross-linked hyaluronan-gelatin hydrogels for tissue engineering", Macromol Biosci. 9(1), Jan. 9, 2009, 20-28.

Visconti, et al., "Towards organ printing: engineering an intra-organ branched vascular tree", Expert Opin Biol Ther. 10(3), 2010, 409-420.

Zarembinski, et al., "The Use of a Hydrogel Matrix as a Cellular Delivery Vehicle in Future Cell-Based Therapies: Biological and Non-Biological Considerations", Regenerative Medicine and Tissue Engineering Cells and Biomaterials, 2011.

Zong, "Electrospun fine-textured scaffolds for heart tissue constructs", Biomaterials. 26(26), 2005, 5330-5338.

Zong, et al., "Structure and process relationship of electrospun bioabsorbable nanofiber membranes", Polymer 43 (16), 2002, 4403-4412.

Phelps, et al., "Maleimide Cross-Linked Bioactive PEG Hydrogel Exhibits Improved Reaction Kinetics and Cross-Linking for Cell Encapsulation and In Situ Delivery", Adv. Mater. (2012), vol. 24, pp. 64-70.

* cited by examiner

A: Shaving and Sterilization   B: Tattoo and Medication

C: Wound Creation and Imaging   D: Treatment Administration

E: Non-adherent Bandaging   F: Protective Saddle and Jacket

E: Biochemical Analysis

A: Contraction

B: Wound healing

A

B

AMNIOTIC MEMBRANE POWDER AND ITS USE IN WOUND HEALING AND TISSUE ENGINEERING CONSTRUCTS

CROSS-REFERENCE TO RELATED APPLICATIONS

The present application is a 35 U.S.C. § 371 national phase application from, and claims priority to, International Application No. PCT/US2015/053571, filed Oct. 1, 2015, and published under PCT Article 21(2) in English, which claims priority under 35 U.S.C. § 119(e) to U.S. Provisional Application No. 62/058,969, filed Oct. 2, 2014, all of which applications are incorporated herein by reference in their entireties.

BACKGROUND OF THE INVENTION

Extensive burns and full thickness skin wounds can be devastating to patients, even when treated. There are an estimated 500,000 burns treated in the United States each year (Cherry et al., 2008, Natl. Health Stat. Report: 1-39; Pitts et al., 2008, Natl. Health Stat. Report: 1-38). The overall mortality rate for burn injury was 4.9% between 1998-2007 and medical costs for burn treatments approach $2 billion per year (Miller et al., 2008, J. Burn Car. Res., 29: 862-871). Globally, this statistic increases to 11 million injuries per year (Peck, 2011, Burns, 37: 1087-1100). In addition to burns, full-thickness chronic wounds constitute a large patient base, and despite technological advancement of treatments, healing rates remain below a 50% success rate (Kurd et al., 2009, Wound Repair Regen., 17: 318-325). These non-healing chronic wounds are estimated to effect 7 million people per year in the United States, with yearly costs approaching $25 billion (Sen et al., 2009, Wound Repair Regen., 17: 763-771). Patients who suffer from either of these types of injuries benefit from rapid treatments that result in complete closure and protection of the wounds. In particular, burn patients who receive delayed treatments often are subject to extensive scarring that can result in negative long-term physiological effects.

The gold standard in the treatment of wound healing is an autologous split-thickness skin graft. This involves removing a piece of skin from a secondary surgical site for the patient, and re-applying the graft on the wound or burn. While this treatment yields a reasonable clinical outcome, if the wound is extensive, then the number and size of donor sites are limited. Allografts are an additional option, and are accompanied by the need for immunosuppressive drugs to prevent immune rejection of the graft. These limitations have thus led to the development of non-cellular dermal substitutes, which are most often comprised of a polymeric scaffold and are costly to produce and result in relatively poor cosmetic outcomes.

Thus, there is a need in the art for a wound healing and regenerative medicine product that has high clinical efficiency. The present invention satisfies this unmet need.

SUMMARY OF THE INVENTION

The present invention relates generally to compositions and methods for inducing wound healing and tissue regeneration.

In one aspect, the present invention includes a composition comprising amniotic membrane powder. In certain embodiments, the amniotic membrane powder of the present invention comprises an amount of total protein in the range of 30 mg/g to 500 mg/g. In other embodiments, the amniotic membrane powder further comprises an amount of elastin in the range of 4 mg/g to 100 mg/g. In yet other embodiments, the amniotic membrane powder further comprises an amount of collagen in the range of 10 mg/g to 800 mg/g. In yet other embodiments, the amniotic membrane powder further comprises an amount of glycosaminoglycans in the range of 0.1 mg/g to 5 mg/g. In yet other embodiments, the amniotic membrane powder further comprises an amount of thrombospondin-1 (TSP-1) in the range of 30 µg/g to 1000 µg/g. In yet other embodiments, the amniotic membrane powder further comprises an amount of pentraxin 3 (PTX-3) in the range of 0.1 µg/g to 50 µg/g. In yet other embodiments, the amniotic membrane powder further comprises an amount of tumor necrosis factor-stimulated gene 6 (TSG-6) less than 1.5 ng/g.

In another aspect, the present invention includes a composition comprising amniotic membrane powder and a scaffold. In certain embodiments, the scaffold is a hydrogel, wherein amniotic membrane powder is incorporated within the hydrogel. In other embodiments, amniotic membrane powder is incorporated within a hyaluronic acid (HA)-based hydrogel. In yet other embodiments, the scaffold comprises at least one biopolymer selected from the group consisting of hyaluronan, chitosan, alginate, collagen, dextran, pectin, carrageenan, polylysine, gelatin and agarose. In yet other embodiments, the scaffold comprises at least one synthetic polymer selected from the group consisting of (meth)acrylate-oligolactide-PEO-oligolactide-(meth)acrylate, poly (ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate.

In yet another aspect, the present invention includes a method of inducing wound healing and tissue regeneration in a subject comprising administering the composition of the present invention to a treatment site in the subject. In certain embodiments, the composition is applied directly to a wound in a subject. In other embodiments, the composition is applied as an aerosol spray, gel, cream, or ointment.

In yet another aspect, the present invention includes a kit pack for inducing wound healing and tissue regeneration in a subject. In certain embodiments, the kit pack comprises a first compartment containing a predetermined amount of hydrogel precursor materials and a second compartment containing a predetermined amount of a composition comprising amniotic membrane powder and a composition comprising a crosslinker. In other embodiments, the kit pack comprises a first compartment containing a predetermined amount of hydrogel precursor materials and a composition comprising amniotic membrane powder and a second compartment containing a predetermined amount of a composition comprising a crosslinker. In yet other embodiments, the kit pack comprises a predetermined amount of amniotic membrane powder, hydrogel precursor materials coated by a water soluble material, and a crosslinker, wherein the amniotic membrane powder, the hydrogel precursor materials coated by the water soluble material, and the crosslinker are desiccated. In yet other embodiments, the kit pack comprises a predetermined amount of amniotic membrane powder, hydrogel precursor materials, and a crosslinker coated by a water soluble material, wherein the amniotic membrane powder, the hydrogel precursor materials, and the crosslinker coated by the water soluble material are desiccated. In yet other embodiments, the kit pack comprises a predetermined amount of amniotic membrane powder, hydrogel precursor materials, and a crosslinker, wherein the hydrogel precursor materials and the crosslinker are desiccated from a solution with a pH<7.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

DETAILED DESCRIPTION

Figure 1:
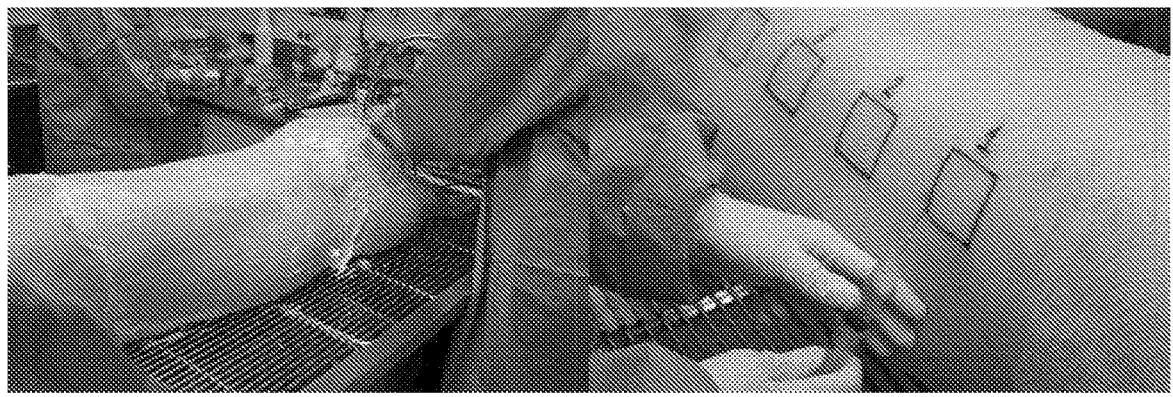
FIG. 1 illustrates the steps involved in the preparation, wound creation, treatment administration and protective bandaging of animals in the study.
Figure 1:
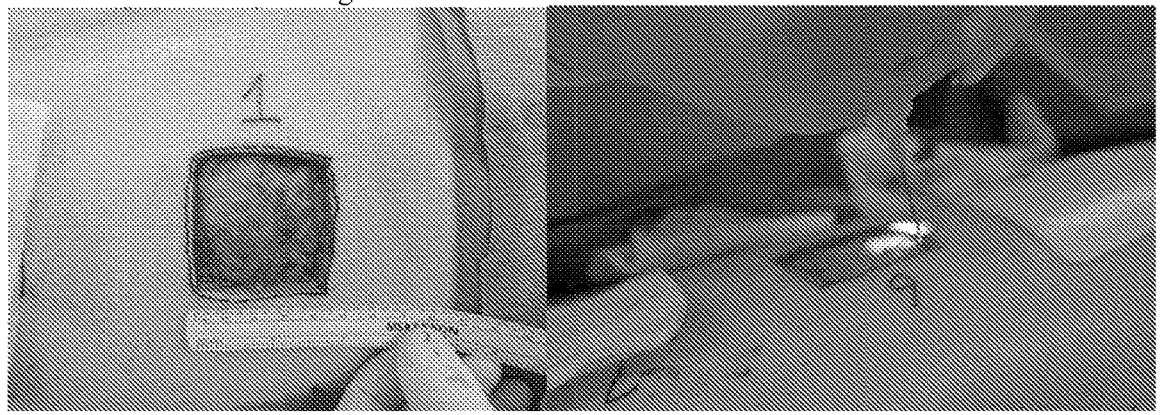
Figure 1:
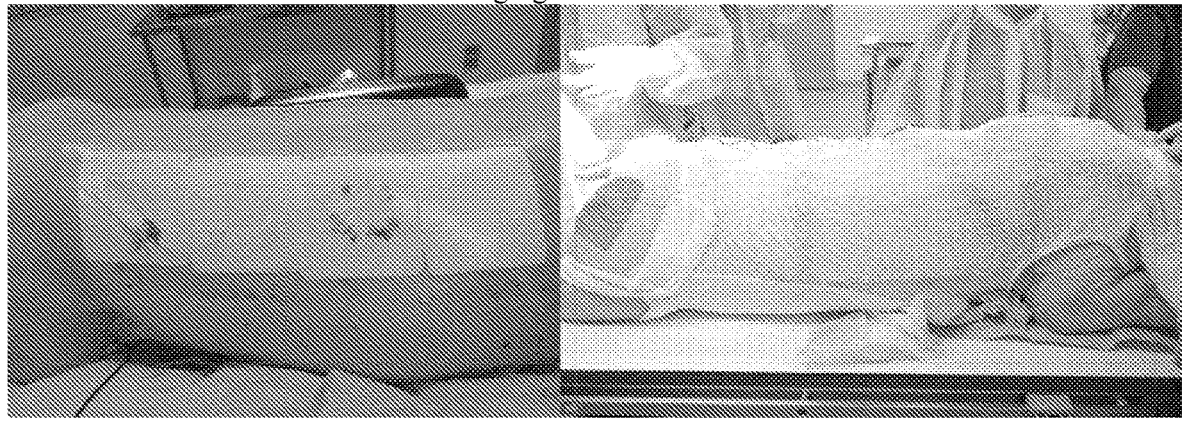

The present invention relates generally to compositions and methods for inducing wound healing and tissue regeneration. In one embodiment, the present invention includes a composition comprising amniotic membrane powder.

In one embodiment, the composition of the invention is cell-free, thereby minimizing potential inflammatory responses in the subject to whom it is administered. The wound healing product of the invention has high clinical efficiency without requiring a cellular component, yet the wound healing product of the invention retains the bioactivity of a cellular treatment.

In one embodiment, the present invention includes a method of applying an amniotic membrane-containing composition to a subject to induce wound healing. For example, in one embodiment, the composition is applied directly to a wound in a subject. In certain embodiments, the composition is applied as an aerosol spray, gel, cream, or ointment.

In one embodiment, the present invention includes an amniotic membrane-based scaffold. In one embodiment, the scaffold is a hydrogel, wherein amniotic membrane powder is incorporated within the hydrogel. In another embodiment, the amniotic membrane-based scaffold of the invention enhances tissue regeneration. In yet another embodiment, the amniotic membrane-based scaffold of the invention reduces tissue contraction. In yet another embodiment, the amniotic membrane-based scaffold enhances blood vessel development in regenerating tissue.

In one embodiment, the present invention includes a method of promoting tissue regeneration in a subject comprising administering to the subject an amniotic membrane-based scaffold.

In another embodiment, amniotic membrane powder is incorporated within a hyaluronic acid (HA)-based hydrogel.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "AMNIOGRAFT®" refers to the amniotic membrane allograft sold by Bio-Tissue, Inc.

As used herein, the term "amniotic membrane-based scaffold" refers to a scaffold that can be used in conjunction with amniotic membrane powder or amniotic solution. For example, such scaffold can be mixed with amniotic membrane powder prior to use, or can be applied to a wound on top of amniotic membrane powder or amniotic solution already applied to such wound.

As used herein, the term "amniotic membrane powder composition" refers to a composition comprising amniotic powder.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure includes a biocompatible substrate onto which different cell populations can be infused. Decellularized biostructures may be rigid, or semi-rigid, having an ability to alter their shapes. Examples of decellularized organs useful in aspects of the present invention include, but are not limited to, the heart, kidney, liver, pancreas, spleen, bladder, ureter and urethra, cartilage, bone, brain, spine cord, peripheral nerve.

The term "derived from" is used herein to mean to originate from a specified source.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, the term "Electrospun Patch" refers to electrospun dextran with amniotic membrane-derived material having no amnion contained therein.

As used herein "endogenous" refers to any material from or produced inside an organism, cell or system.

"Exogenous" refers to any material introduced from or produced outside an organism, cell, or system.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" is used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft," "allogeneic transplant," "allogeneic implant," and "allogeneic graft." A graft from an individual to his identical twin is referred to herein as an "isograft," a "syngeneic transplant," a "syngeneic implant" or a "syngeneic graft." A "xenograft," "xenogeneic transplant," or "xenogeneic implant" refers to a graft from one individual to another of a different species.

As used herein, "GRAFTJACKET®" refers to a scaffold sold by Wright Medical Technology, Inc. It comprises biological substrate components including collagen type I, III, IV, and VII, elastin, chondroitin sulfate, proteoglycans, hyaluronic acid, laminin, tenacin, and fibroblast growth factor.

As used herein "a growth factor" is intended to include the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein, the term "hydrogel precursor materials" refers to hydrophilic biopolymers or synthetic polymers, or a mixture thereof, used to make a hydrogel by reacting the precursor materials with a crosslinker. The hydrophilic biopolymers or synthetic polymer may be modified to better facilitate the crosslinking reaction. One non-limiting example of modification is thiolation (e.g., incorporating thiol functional groups).

"Native cells," as used herein means cells that are native, resident, or endogenous to the placental membrane, i.e., cells that are not exogenously added to the placental membrane.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a mammal, and in other embodiments, the mammal is a human.

"Proliferation" is used herein to refer to the reproduction or multiplication of similar forms, especially of cells. That is, proliferation encompasses production of a greater number of cells, and may be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g., a form with two-dimensions substantially greater than the third dimension), ribbons, cords, sheets, flat discs, cylinders, spheres, 3-dimensional amorphous shapes, etc. One non-limiting example of a scaffold is a hydrogel.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

As used herein, "tissue engineering" refers to the process of generating a tissue ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, the terms "tissue grafting" and "tissue reconstructing" both refer to implanting a graft into an individual to treat or alleviate a tissue defect, such as a lung defect or a soft tissue defect.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

The term "wound" as used herein refers to all types of tissue injuries, including those inflicted by surgery and trauma, including burns, as well as injuries from chronic medical conditions, such as atherosclerosis, vascular disease, or diabetes. The compositions described herein are useful for treatment of all types of wounds, including wounds to internal and external tissues. The wound dressings are intended to treat the various etiologies of wounds that affect the three layers of the skin (i.e., the epidermis, dermis, and subcutaneous layers).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Composition

The present invention includes an amniotic membrane composition comprising amniotic membrane powder for use in wound healing and tissue regeneration applications. The amniotic membrane, or amnion, is a thin tissue that forms the wall of the amniotic sac. During pregnancy, the amniotic membrane surrounds and protects a developing embryo. The amniotic membrane comprises a thick basement membrane and an avascular stromal matrix.

In one aspect, the composition comprises an amount of total protein in the range of 30 mg/g to 500 mg/g. Suitably, the amount is in the range of 40 mg/g to 450 mg/g; suitably, the amount is in the range of 50 mg/g to 400 mg/g; suitably, the amount is in the range of 50 mg/g to 250 mg/g; suitably, the amount is in the range of 60 mg/g to 350 mg/g; suitably, the amount is in the range of 70 mg/g to 300 mg/g; suitably, the amount is in the range of 80 mg/g to 250 mg/g; suitably, the amount is in the range of 90 mg/g to 250 mg/g; suitably, the amount is in the range of 100 mg/g to 250 mg/g; suitably, the amount is in the range of 110 mg/g to 250 mg/g; suitably, the amount is in the range of 120 mg/g to 250 mg/g; suitably, the amount is in the range of 130 mg/g to 250 mg/g; suitably, the amount is in the range of 140 mg/g to 250 mg/g.

In another aspect, the composition comprises an amount of elastin in the range of 4 mg/g to 100 mg/g. Suitably, the amount is in the range of 5 mg/g to 60 mg/g; suitably, the amount is in the range of 10 mg/g to 95 mg/g; suitably, the amount is in the range of 15 mg/g to 90 mg/g; suitably, the amount is in the range of 20 mg/g to 85 mg/g; suitably, the amount is in the range of 25 mg/g to 80 mg/g; suitably, the amount is in the range of 30 mg/g to 75 mg/g; suitably, the amount is in the range of 35 mg/g to 70 mg/g; suitably, the amount is in the range of 40 mg/g to 65 mg/g; suitably, the amount is in the range of 40 mg/g to 60 mg/g; suitably, the amount is in the range of 40 mg/g to 55 mg/g.

In yet another aspect, the composition comprises an amount of collagen in the range of 10 mg/g to 800 mg/g. Suitably, the amount is in the range of 10 mg/g to 600 mg/g; suitably, the amount is in the range of 50 mg/g to 750 mg/g; suitably, the amount is in the range of 100 mg/g to 700 mg/g; suitably, the amount is in the range of 150 mg/g to 650 mg/g; suitably, the amount is in the range of 200 mg/g to 600 mg/g; suitably, the amount is in the range of 250 mg/g to 550 mg/g; suitably, the amount is in the range of 300 mg/g to 500 mg/g; suitably, the amount is in the range of 350 mg/g to 450 mg/g; suitably, the amount is in the range of 400 mg/g to 550 mg/g.

In yet another aspect, the composition comprises an amount of glycosaminoglycans in the range of 0.1 mg/g to 5 mg/g. Suitably, the amount is in the range of 0.2 mg/g to 3.5 mg/g; suitably, the amount is in the range of 0.3 mg/g to 3.0 mg/g; suitably, the amount is in the range of 0.4 mg/g to 2.5 mg/g; suitably, the amount is in the range of 0.5 mg/g to 2.0 mg/g; suitably, the amount is in the range of 0.6 mg/g to 1.8 mg/g; suitably, the amount is in the range of 0.7 mg/g to 1.5 mg/g; suitably, the amount is in the range of 0.8 mg/g to 1.4 mg/g; suitably, the amount is in the range of 0.9 mg/g to 1.3 mg/g.

In yet another aspect, the composition comprises an amount of thrombospondin-1 (TSP-1) in the range of 30 µg/g to 1000 µg/g. Suitably, the amount is in the range of 50 µg/g to 950 µg/g; suitably, the amount is in the range of 50 µg/g to 400 µg/g; suitably, the amount is in the range of 75 µg/g to 900 µg/g; suitably, the amount is in the range of 100 µg/g to 850 µg/g; suitably, the amount is in the range of 125 µg/g to 800 µg/g; suitably, the amount is in the range of 150 µg/g to 750 µg/g; suitably, the amount is in the range of 175 µg/g to 700 µg/g; suitably, the amount is in the range of 200 µg/g to 650 µg/g; suitably, the amount is in the range of 225 µg/g to 600 µg/g; suitably, the amount is in the range of 250 µg/g to 550 µg/g; suitably, the amount is in the range of 275 µg/g to 500 µg/g; suitably, the amount is in the range of 300 µg/g to 450 µg/g.

In yet another aspect, the composition comprises an amount of pentraxin 3 (PTX-3) in the range of 0.1 µg/g to 50 µg/g. Suitably, the amount is in the range of 1 µg/g to 45 µg/g; suitably, the amount is in the range of 1 µg/g to 40 µg/g; suitably, the amount is in the range of 2 µg/g to 40 µg/g; suitably, the amount is in the range of 3 µg/g to 35 µg/g; suitably, the amount is in the range of 4 µg/g to 40 µg/g; suitably, the amount is in the range of 5 µg/g to 35

μg/g; suitably, the amount is in the range of 6 μg/g to 30 μg/g; suitably, the amount is in the range of 7 μg/g to 25 μg/g; suitably, the amount is in the range of 8 μg/g to 25 μg/g. Suitably, the amount is in the range of 9 μg/g to 20 μg/g; suitably, the amount is in the range of 10 μg/g to 15 μg/g.

In yet another aspect, the composition comprises an amount of tumor necrosis factor-stimulated gene 6 (TSG-6) less than 1.5 ng/g. Suitably, the amount of TSG-6 is less than 1.3 ng/g; suitably, the amount of TSG-6 is less than 1.1 ng/g; suitably, the amount of TSG-6 is less than 1.0 ng/g; suitably, the amount of TSG-6 is less than 0.7 ng/g; suitably, the amount of TSG-6 is less than 0.5 ng/g; suitably, the amount of TSG-6 is less than 0.3 ng/g; suitably, the amount of TSG-6 is less than 0.1 ng/g.

In certain embodiments, the composition comprises total protein in the range of 30 mg/g to 500 mg/g and elastin in the range of 4 mg/g to 100 mg/g. Suitably, the amount of total protein is in the range of 50 mg/g to 250 mg/g and elastin is in the range of 5 mg/g to 60 mg/g; suitably, the amount of total protein is in the range of 100 mg/g to 250 mg/g and elastin is in the range of 20 mg/g to 60 mg/g.

In certain embodiments, the composition comprises total protein in the range of 30 mg/g to 500 mg/g and collagen in the range of 10 mg/g to 800 mg/g. Suitably, the amount of total protein is in the range of 50 mg/g to 250 mg/g and collagen is in the range of 10 mg/g to 600 mg/g; suitably, the amount of total protein is in the range of 100 mg/g to 250 mg/g and collagen is in the range of 100 mg/g to 600 mg/g.

In certain embodiments, the composition comprises total protein in the range of 30 mg/g to 500 mg/g and glycosaminoglycans in the range of 0.1 mg/g to 5 mg/g. Suitably, the amount of total protein is in the range of 50 mg/g to 250 mg/g and glycosaminoglycans is in the range of 0.5 mg/g to 4 mg/g; suitably, the amount of total protein is in the range of 100 mg/g to 250 mg/g and glycosaminoglycans is in the range of 0.5 mg/g to 2 mg/g.

In certain embodiments, the composition comprises collagen in the range of 10 mg/g to 800 mg/g and glycosaminoglycans in the range of 0.1 mg/g to 5 mg/g. Suitably, the amount of collagen is in the range of 10 mg/g to 600 mg/g and glycosaminoglycans is in the range of 0.5 mg/g to 4 mg/g; suitably, the amount of collagen is in the range of 100 mg/g to 600 mg/g and glycosaminoglycans is in the range of 0.5 mg/g to 2 mg/g.

In certain embodiments, the composition comprises collagen in the range of 10 mg/g to 800 mg/g and elastin in the range of 4 mg/g to 100 mg/g. Suitably, the amount of collagen is in the range of 10 mg/g to 600 mg/g and elastin is in the range of 5 mg/g to 60 mg/g; suitably, the amount of collagen is in the range of 100 mg/g to 600 mg/g and elastin is in the range of 20 mg/g to 60 mg/g.

In certain embodiments, the composition comprises glycosaminoglycans in the range of 0.1 mg/g to 5 mg/g and elastin in the range of 4 mg/g to 100 mg/g. Suitably, the amount of glycosaminoglycans is in the range of 0.5 mg/g to 4 mg/g and elastin is in the range of 5 mg/g to 60 mg/g; suitably, the amount of glycosaminoglycans is in the range of 0.5 mg/g to 2 mg/g and elastin is in the range of 20 mg/g to 60 mg/g.

In certain embodiments, the composition comprises total protein in the range of 30 mg/g to 500 mg/g, elastin in the range of 4 mg/g to 100 mg/g, and collagen in the range of 10 mg/g to 800 mg/g. Suitably, the amount of total protein is in the range of 50 mg/g to 250 mg/g, elastin is in the range of 5 mg/g to 60 mg/g, and collagen is in the range of 10 mg/g to 600 mg/g; suitably, the amount of total protein is in the range of 100 mg/g to 250 mg/g, elastin is in the range of 20 mg/g to 60 mg/g, and collagen is in the range of 100 mg/g to 600 mg/g.

In certain embodiments, the composition comprises total protein in the range of 30 mg/g to 500 mg/g, elastin in the range of 4 mg/g to 100 mg/g, and glycosaminoglycans in the range of 0.1 mg/g to 5 mg/g. Suitably, the amount of total protein is in the range of 50 mg/g to 250 mg/g, elastin is in the range of 5 mg/g to 60 mg/g, and glycosaminoglycans is in the range of 0.5 mg/g to 4 mg/g; suitably, the amount of total protein is in the range of 100 mg/g to 250 mg/g, elastin is in the range of 20 mg/g to 60 mg/g, and glycosaminoglycans is in the range of 0.5 mg/g to 2 mg/g.

In certain embodiments, the composition comprises total protein in the range of 30 mg/g to 500 mg/g, collagen in the range of 10 mg/g to 800 mg/g, and glycosaminoglycans in the range of 0.1 mg/g to 5 mg/g. Suitably, the amount of total protein is in the range of 50 mg/g to 250 mg/g, collagen is in the range of 10 mg/g to 600 mg/g, and glycosaminoglycans is in the range of 0.5 mg/g to 4 mg/g; suitably, the amount of total protein is in the range of 100 mg/g to 250 mg/g, collagen is in the range of 100 mg/g to 600 mg/g, and glycosaminoglycans is in the range of 0.5 mg/g to 2 mg/g.

In certain embodiments, the composition comprises elastin in the range of 4 mg/g to 100 mg/g, collagen in the range of 10 mg/g to 800 mg/g, and glycosaminoglycans in the range of 0.1 mg/g to 5 mg/g. Suitably, the amount of elastin is in the range of 5 mg/g to 60 mg/g, collagen is in the range of 10 mg/g to 600 mg/g, and glycosaminoglycans is in the range of 0.5 mg/g to 4 mg/g; suitably, the amount of elastin is in the range of 20 mg/g to 60 mg/g, collagen is in the range of 100 mg/g to 600 mg/g, and glycosaminoglycans is in the range of 0.5 mg/g to 2 mg/g.

In certain embodiments, the composition comprises total protein in the range of 30 mg/g to 500 mg/g, elastin in the range of 4 mg/g to 100 mg/g, collagen in the range of 10 mg/g to 800 mg/g, and glycosaminoglycans in the range of 0.1 mg/g to 5 mg/g. Suitably, the amount of total protein is in the range of 50 mg/g to 250 mg/g, elastin is in the range of 5 mg/g to 60 mg/g, collagen is in the range of 10 mg/g to 600 mg/g, and glycosaminoglycans is in the range of 0.5 mg/g to 4 mg/g; suitably, the amount of total protein is in the range of 100 mg/g to 250 mg/g, elastin is in the range of 20 mg/g to 60 mg/g, collagen is in the range of 100 mg/g to 600 mg/g, and glycosaminoglycans is in the range of 0.5 mg/g to 2 mg/g.

In certain embodiments, the composition comprises total protein in the range of 30 mg/g to 500 mg/g, elastin in the range of 4 mg/g to 100 mg/g, collagen in the range of 10 mg/g to 800 mg/g, glycosaminoglycans in the range of 0.1 mg/g to 5 mg/g, and thrombospondin-1 (TSP-1) in the range of 30 μg/g to 1,000 μg/g.

In certain embodiments, the composition comprises total protein in the range of 30 mg/g to 500 mg/g, elastin in the range of 4 mg/g to 100 mg/g, collagen in the range of 10 mg/g to 800 mg/g, glycosaminoglycans in the range of 0.1 mg/g to 5 mg/g, and pentraxin 3 (PTX-3) in the range of 0.1 μg/g to 50 μg/g.

In certain embodiments, the composition comprises total protein in the range of 30 mg/g to 500 mg/g, elastin in the range of 4 mg/g to 100 mg/g, collagen in the range of 10 mg/g to 800 mg/g, glycosaminoglycans in the range of 0.1 mg/g to 5 mg/g, and tumor necrosis factor-stimulated gene 6 (TSG-6) less than 1.5 ng/g.

In yet another aspect, the composition comprises total protein in the range of 30 mg/g to 500 mg/g, elastin in the range of 4 mg/g to 100 mg/g, collagen in the range of 10 mg/g to 800 mg/g, glycosaminoglycans in the range of 0.1 mg/g to 5 mg/g, thrombospondin-1 (TSP-1) in the range of 30 μg/g to 1,000 μg/g, pentraxin 3 (PTX-3) in the range of 0.1 μg/g to 50 μg/g, and tumor necrosis factor-stimulated gene 6 (TSG-6) less than 1.5 ng/g.

The method of preparing amniotic membrane powder and composition comprising amniotic membrane powder is disclosed in PCT/US13/58940, filed Sep. 10, 2013, the disclosure of which is incorporated herein in its entirety.

The present invention also includes pharmaceutical compositions comprising amniotic membrane powder. As described elsewhere herein, the present invention is based upon the finding that amniotic membrane enhances wound healing and tissue regeneration. Formulations may be employed in admixtures with additional ingredients, for example, conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of amnionic membrane powder. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g., disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

In certain instances, one benefit of the composition of the present invention is that it has the ability to fill irregular and deep wounds. Thus, in one embodiment, the pharmaceutical composition may be topically applied to a wound or to a site in need of tissue regeneration.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the formulations suitable for topical administration may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the amniotic membrane components into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

Formulations suitable for topical administration should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

In another embodiment, the pharmaceutical composition comprising amniotic membrane powder may be applied to a bandage or dressing, which is then applied to the wound or treatment site of a subject. For example, in one embodiment, a dressing is soaked in a liquid solution or liquid suspension comprising amniotic membrane powder. In another embodiment, an ointment comprising amniotic membrane powder is applied to a surface of a dressing or bandage.

In another embodiment, the pharmaceutical composition comprises an aerosolized or atomized solution or suspension comprising amniotic membrane powered. Such aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Amniotic Membrane-Based Scaffolds

The present invention includes an amniotic membrane-based scaffold useful in wound healing and tissue regeneration. For example, in one embodiment, amniotic membrane powder is incorporated within a scaffold. In some instances, amniotic membrane powder is applied to the surface of a scaffold or mixed on site with the scaffold. In one embodiment, the scaffold is applied to the wound area on top of amniotic membrane powder or a composition comprising amniotic membrane powder and a scaffold is applied to the wound area. For example, when the scaffold is a hydrogel, the hydrogel is applied to the wound area directly on top of amniotic membrane powder or a composition comprising amniotic membrane powder is applied to the wound area. The scaffold of the invention may be of any type known in the art. Non-limiting examples of such a scaffold include hydrogel, electrospun scaffold, foam, mesh, sheet, patch, and sponge.

In one embodiment, the scaffold may comprise any polysaccharide, including glycosaminoglycans (GAGs) or glucosaminoglycans, with suitable viscosity, molecular mass and other desirable properties. Glycosaminoglycan refers to any glycan (i.e., polysaccharide) comprising an unbranched polysaccharide chain with a repeating disaccharide unit, provided one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glucosaminoglycan is also intended any glycan (i.e., polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate. For clarity, although the scaffold may itself be a hydrogel, the scaffold does not necessarily have to be a hydrogel.

(a) Hydrogels

In one embodiment, the present invention includes a composition comprising a hydrogel and amniotic membrane powder. Hydrogels can generally absorb a great deal of fluid and, at equilibrium, typically are composed of 60-99% fluid and only 1-40% polymer. In some instances, the water content of hydrogel is about 99%. In other instances, the water content of hydrogel is about 70-90%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility may be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels may be prepared by crosslinking hydrophilic biopolymers or synthetic polymers or both. In other words, hydrogels are prepared by reacting precursor materials with crosslinkers, wherein the precursor materials are hydrophilic biopolymers or synthetic polymers or both. Examples of the hydrogels formed from physical or chemical crosslinking of hydrophilic biopolymers, include but are not limited to, hyaluronans, chitosans, gelatin, alginates, collagen, dextran, pectin, carrageenan, polylysine, gelatin or agarose. (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly (ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12).

There are many types of crosslinkers known in the art that can be used to make hydrogels in the invention (Fei, et al., 2000, Journal of Applied Polymer Science, 78: 278-283;

Hennink, et al., 2002, Advanced Drug Delivery Reviews, 54: 13-36; Janik, et al., 2008, Nuclear Instruments & Methods in Physics Research Section B-Beam Interactions with Materials and Atoms, 208: 374-379; Liu, et al., 2005, Radiation Physics and Chemistry 72: 635-638; Nagasawa, et al., 2004, Carbohydrate Polymers, 58: 109-113; Onuki, et al, 2008, International Journal of Pharmaceutics, 349: 47-52; Shen, et al., 2006, Polymer Bulletin, 56: 137-143; Shu, et al., 2004, Biomaterials, 25: 1339-1348). In certain embodiments, one or more crosslinkers may be utilized to make hydrogels. Such crosslinkers may include, but not limited to, glutaraldehyde, epoxides (e.g., bis-oxiranes), oxidized dextran, p-azidobenzoyl hydrazide, N-[α.-maleimidoacetoxy] succinimide ester, p-azidophenyl glyoxal monohydrate, bis-[β-(4-azidosalicylamido)ethyl]disulfide, bis [sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS), poly(ethylene glycol) diacrylate (PEGDA), PEGDMal and other bifunctional cross-linking reagents known to those skilled in the art. It should be appreciated by those in skilled in the art that the mechanical properties of the hydrogel are greatly influenced by the cross-linking time and the amount of cross-linking agents. In one embodiment, the crosslinkers is poly(ethylene glycol) diacrylate (PEGDA); in another embodiment, the cross-linker is poly (ethylene glycol) based crosslinker with maleimide functional groups (PEGDMal).

In one embodiment, the hydrogel comprises at least one biopolymer. In other embodiments, the hydrogel scaffold further comprises at least two biopolymers. In yet other embodiments, the hydrogel scaffold further comprises at least one biopolymer and at least one synthetic polymer. In one embodiment, the hydrogel of the present invention comprises hyaluronic acid, gelatin, and PEGDMal.

In one embodiment, components of the hydrogel of the invention are modified. For example, in one embodiment, monomers may be modified with methacrylic anhydride (MA); in another embodiment, monomers or the hydrogel precursor materials may be thiolated (e.g., incorporating thiol functional groups).

Hydrogels and methods of their preparation that can be used in the present invention have been disclosed in patent application PCT/US13/58940, filed Sep. 10, 2013, which is hereby incorporated herein in its entirety.

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels may also be made degradable in vivo by incorporating PLA, PLGA or PGA polymers. Moreover, hydrogels may be modified with fibronectin, laminin, vitronectin, or, for example, RGD for surface modification, which may promote cell adhesion and proliferation (Heungsoo Shin, 2003, Biomaterials 24: 4353-4364; Hwang et al., 2006 Tissue Eng. 12: 2695-706). Indeed, altering molecular weights, block structures, degradable linkages, and cross-linking modes may influence strength, elasticity, and degradation properties of the instant hydrogels (Nguyen and West, 2002, Biomaterials 23(22): 4307-14; Ifkovits and Burkick, 2007, Tissue Eng. 13(10): 2369-85).

Hydrogels may also be modified with functional groups for covalently attaching a variety of proteins (e.g., collagen) or compounds such as therapeutic agents. Therapeutic agents which may be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix may be via a protease sensitive linker or other biodegradable linkage. Molecules which may be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent may include any compound, especially polar compounds that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents may be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the crosslinked macromolecules in the presence of the enhancing and strengthening polar amino acids, as well as other enhancing agents.

In one embodiment, amniotic membrane powder is incorporated into the hydrogel. For example, amniotic membrane powder may be added to or mixed with the hydrogel solution prior to gelation or polymerization of the gel. Amniotic membrane powder may be added to a hydrogel solution in any amount desired to produce a desired effect. In one embodiment, an effective amount of amniotic membrane powder is applied to a wound directly, then a hydrogel is applied on top of the amniotic membrane powder. In some embodiments, the hydrogel permits diffusion of amniotic membrane components into and throughout the hydrogel.

(b) Method for Forming Scaffolds

Method of preparing scaffolds that can be used with present invention have been disclosed in patent application PCT/US13/58940, filed Sep. 10, 2013, which is hereby incorporated herein in its entirety.

Therapeutics

In one application, the invention includes a method of promoting the closure of a wound in a patient using the composition of the invention. In one embodiment, the method of the invention is useful for clinical and personal wound care and soft tissue regeneration. In accordance with the method, the composition comprising amniotic membrane powder is transferred to a wound. The method promotes closure of both external (e.g., surface) and internal wounds. Wounds for which the present inventive method is useful in promoting closure include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, or tangential wounds. The method need not achieve complete healing or closure of the wound; it is sufficient that the method serve to promote any degree of wound closure. In this respect, the method may be employed alone or as an adjunct to other methods for healing wounded tissue.

In one embodiment, the composition comprising amniotic membrane powder is applied directly to a wound or treatment site of a subject. As described elsewhere herein, the amniotic membrane powder may be incorporated into a pharmaceutical formulation including topical ointments, creams, aerosol sprays, and the like.

In one aspect of the invention, the method comprises using an amniotic membrane-based scaffold, described elsewhere herein, as a wound dressing or graft for external skin wounds. In a clinical setting, the scaffold may be used to treat wounds resulting from trauma, burns, ulcers, abrasions, lacerations, surgery, or other damage. Surgeons can use these scaffolds to cover and protect the wound area, to temporarily replace lost or damaged skin tissue, and to guide new tissue generation and wound healing into the damaged area. In a clinical setting, in some embodiments, the scaffold may be secured to the wound area using sutures, adhesives, or overlaying bandages. The scaffold may be cut to match the size of the wound, or may overlap the wound edges. In some instances the scaffold may be shaped to penetrate into cavities formed by deep wounds.

In one embodiment, a hydrogel is applied in a flowable state to a wound or treatment site. In some instances, the hydrogel polymerizes at the wound or treatment site. In one embodiment, the hydrogel is induced to polymerize instantaneously prior to use, for example through PEGDMal. In another embodiment, the hydrogel is formed at the treatment site instantaneously using a duel chamber syringe or the like, wherein one chamber contains a crosslinker, while the other contains a biopolymer or a synthetic polymer or both. In another embodiment, the hydrogel is applied to a wound right after a composition comprising amniotic membrane powder is applied to such wound.

In another aspect of the invention, the method includes a kit pack for inducing wound healing and tissue regeneration in a subject. The pack has two compartments with a barrier or the like to separate them. In other words, the pack has one enclosure and one barrier that separates the enclosure into two compartments. In one embodiment, the two compartments are the same size. In another embodiment, the two compartments are different in size. In yet another embodiment, one compartment encloses the other compartment. In one embodiment, one compartment of the pack contains a predetermined amount of hydrogel precursor materials; the other compartment contains a predetermined amount of a composition comprising amniotic membrane powder and a composition comprising a crosslinker. In another embodiment, one compartment of the pack contains a predetermined amount of a composition comprising amniotic membrane powder and hydrogel precursor materials and the other compartment contains a composition comprising a crosslinker. In yet another embodiment, one compartment contains a predetermined amount of hydrated hydrogel precursor materials and a composition comprising amniotic membrane powder; the other compartment contains a composition comprising a crosslinker.

The barrier must be sufficiently strong to maintain seals between the compartments during normal handling. At the same time, the barrier must be susceptible to a means of rupture at the time of use. Rupture of the barrier is accomplished by gripping the pack in the middle and rapidly pulling or jerking from both ends. Alternatively, the barrier can be ruptured by squeezing, cap twisting, pressing a plunger, shaking vigorously or kneading the compartments. Once the barrier is ruptured, the amniotic membrane powder in one compartment can be mixed with the hydrogel therein or formed in situ.

Alternatively, the barrier functions like a valve with a control outside the pack to open the barrier right before use. In this case, the barrier does not have to be ruptured.

In another embodiment, the pack has one compartment. Such compartment comprises a predetermined amount of amniotic membrane powder, hydrogel precursor materials coated with a water soluble material, and a crosslinker. All these components are in desiccated form so that the hydrogel precursor materials coated with a water soluble material do not react with the crosslinker Immediately prior to use, water is added into the pack which dissolves the coating. The exposed hydrogel precursor materials then react with the crosslinker to form a hydrogel. In one non-limiting example, the water soluble coating material is gelatin.

In yet another embodiment, the pack has one compartment. Such compartment comprises a predetermined amount of amniotic membrane powder, hydrogel precursor materials, and a crosslinker coated with a water soluble material. All these components are in desiccated form so that the hydrogel precursor materials do not react with the crosslinker coated with a water soluble material Immediately prior to use, water is added into the pack which dissolves the coating. The exposed crosslinker then reacts with the hydrogel precursor materials to form a hydrogel. In one non-limiting example, the water soluble coating material is gelatin.

In yet another embodiment, the pack also has one compartment. The compartment comprises a predetermined amount of amniotic membrane powder, hydrogel precursor materials, and a crosslinker. The hydrogel precursor materials and crosslinker are desiccated from a solution having a pH less than 7. In certain embodiments, the pH is in the range 0.1 to 6.5. In one example, the pH is 6; or 5; or 4; or 3; or 2; or 1 Immediately prior to use, basic water is added into the pack to neutralize the resulting solution to approximately pH=7, whereupon the hydrogel precursor materials and the crosslinker react to form the hydrogel.

In yet another embodiment, the pack is vacuum sealed and further comprises desiccant materials.

The kit pack is beneficial for increasing storage time, maintaining suitable storage temperatures, maintenance of bioactive components, and for providing convenient timing for the formation of the hydrogel and application of the product to the subject.

In one embodiment, the enclosure is made of polyethylene, polypropylene, polyester aluminum, aluminized polymer film, and other conventional plastic or other packaging materials suitable for the present invention.

In one embodiment, the barrier is made of polyethylene, polypropylene, polyester aluminum, aluminized polymer film, gelatin and other conventional plastic or other packaging materials suitable for the present invention.

In one embodiment, the kit pack has an indicator to indicate the barrier or the like is ruptured. In one instance, the indicator is a pH-dependent dye (such as phenol red). Upon mixing the pH equilibrates at 7, resulting in the correct color.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

General Procedure of Preparing Amniotic Membrane Powder

Donated human placenta was collected and stored at 4° C. until further use. The amnion membrane (avascular/inner) was manually dissected from the chorion membrane (vascular/outer). Any blood clots which were present were removed. The membrane was washed with 500-1000 mL of sterile saline.

Using sterile scissors and forceps, the amnion membrane was cut into approximately 5×5 cm pieces. The amnion pieces were then transferred into a sterile 500 mL container and washed five times with 100 mL sterile saline. Pieces were then washed with 500 mL sterile water.

The amnion pieces were transferred into 50 mL tubes. During transfer, the pieces were dragged along the edge of the 500 mL container in order to remove as much water as possible from each piece. Each 50 mL tube was filled to a maximum of 25 mL. The 50 mL tubes containing the amnion pieces were then kept at −80° C. for 12-24 hours.

The lids of the 50 mL tubes were removed, and the tubes were covered with parafilm. Several small holes were poked into the parafilm. The tubes were placed in a pre-cooled glass lyophilizer container, and were lyophilized for 48-72 hours.

A SPEX® SAMPLEPREP®8970 freezer/mill was filled with liquid nitrogen. The lyophilized amnion membrane pieces were placed into the freezer/mill chamber. Membrane pieces were milled for 3 cycles of 5 minutes of cool, 5 minutes of mill. The powder was then gamma irradiated for 1 hour at 1 mega rad, and then was stored in aliquots at −80° C. until further use.

Comparison Experiments

A comparison study has been conducted between the amniotic membrane powder of the present invention (hereinafter "AMP") and amnion membrane-derived product described in Tseng, et al., US 2007/0071740 A1 (hereinafter "Tseng Product").

Steps of Preparation of AMP:
1. Collect donated human placenta. Store at 4° C. until use.
2. Manually dissect amnion membrane (avascular/inner) from the chorion membrane (vascular/outer).
3. Remove any blood clots and wash membrane with 500-1000 mL sterile saline.
4. Use sterile scissors and forceps to cut amnion membrane into approximately 5×5 cm pieces.
5. Transfer amnion pieces into sterile 500 mL container and wash with 100 mL sterile saline five times.
6. Perform wash with 500 mL sterile water.
7. Transfer amnion pieces into 50 mL tubes removing as much water as possible from each piece by dragging along edge of 500 mL container.
8. Fill each 50 mL tube to maximum of 25 mL.
9. Place 50 mL tubes containing amnion pieces into −80° C. for 12-24 hours.
10. Remove lids from 50 mL tubes and cover with Parafilm. Poke several small holes in the Parafilm.
11. Place tubes in a pre-cooled glass lyophilizer container and lyophilize for 24-48 hrs.
12. Fill Spex Sampleprep 6870 freezer/mill with liquid nitrogen.
13. Place lyophilized amnion membrane into freezer/mill chamber and mill for 3× cycles of 5 minutes cool, 5 minutes mill.
14. Weigh powder and store at −80° C.

Steps of Preparation of Tseng (Based on US 2007/0071740 A1. Claims and Paragraph [0095])
1. Collect and freeze placenta in a commercially available −80° C. deep freezer (storage can range from 48 hours to 7 days).
2. Transfer placenta to an environment of 4° C. (refrigerator) for 24 hours.
3. Move to room temperature with or without addition of normal saline solution for 4 hours.
4. Isolate amniotic material from thawed placenta.
5. Wash in HBSS (Invitrogen Cat #14175), place in sterile centrifuge tube and centrifuge at 4° C. for 5 minutes at 5000 rpm.
6. Remove fluid and weigh amnion material.

Steps 7 and 8 Optional but Performed
7. Slice amniotic membrane into small pieces to fit into barrel of a Biopulverizer.
8. Freeze in liquid nitrogen, pulverize into fine powder and weigh.
9. Prepare cold 1×PBS buffer, pH 7.4, containing protease inhibitors (protease inhibitor cocktail P8340, Sigma, and supplemented with 1 mM PMSF) and phosphatase inhibitors (50 mM sodium fluoride and 0.2 mM sodium vanadate).
10. Add buffer to powder at 1:1 (mL/g).
11. Keep on ice and homogenize with a Tissue Tearor (Biospec products) 5 times, 1 minute each, with a 2 minute cooling interval.

12. These water-soluble extracts are designated "Total" Amniotic membrane Extracts (AME).
13. Store Total AME for further analysis.

Initial Observations

The protocol disclosed in Tseng involves multiple and prolonged freeze/thaw steps, resulting in the storage of the amnion material at 4° C. or room temperature for extended periods of time. In comparison, the AMP is isolated as rapidly as possible and immediately frozen at −80° C. before preservation by lyophilization. This methodology ensures the preservation of sensitive and potentially bioactive components of the product. The AMP is stable and maintains its powder state at room temperature. The Tseng Product only resembles a powder briefly after removing it from liquid nitrogen at step 8. After this stage, the powder rapidly 'melts' into a liquid slurry. Additionally, the lack of repeated and thorough washing steps results in a product that is contaminated with blood and other biological contaminants, resulting in the final product appearing red, while AMP is white/beige in appearance.

Assays

Figure 26:
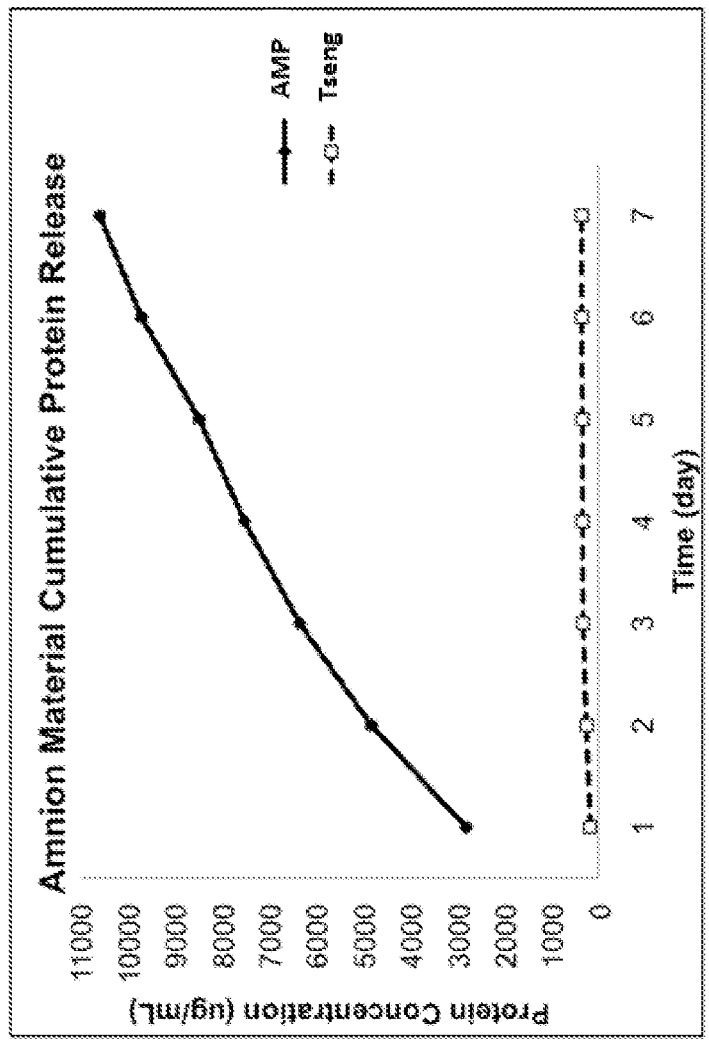
FIG. 26 is a graph illustrating cumulative protein release over time from amniotic membrane powder described herein (AMP) vs. Tseng (US 2007/0071740 A1; hereinafter "Tseng Product").

All assays were performed with equal amounts of products by weight. The final Tseng Product is in a liquid form comprising 1 g/mL Tseng 'powder.' Therefore, a suitable volume of Tseng Product was used to match the weight of AMP. The assays used included colorimetric assays (PIERCE®/SIRCOL®) to measure total protein, collagen, elastin and GAGs, QUANTIKINE® ELISA kits (R&D systems, MyBiosource) to measure TSG-6, PTX-3, and TSP-1. Real-time PCR was performed to measure gene expression. Protein release from the AMP and Tseng Product over 7 days was assessed (FIG. 26). Twenty five mg of each material was placed in microcentrifuge tubes and topped up to 200 uL with PBS. Each day, the tubes were centrifuged for 5 minutes at 6000 rpm to separate the insoluble material and the supernatant. The supernatants were collected and frozen for future analysis and 200 uL of fresh PBS was added back to each tube. Incubation was performed at 37° C. on a shaker. All assays were formed on three separate amnion isolations for each amnion product (n=3) and were performed using positive control standards used to generate standard curves for the colorimetric assays and plate-based ELISAs. Maximum suggested starting material weight was used for all assays with the exception of the TSG-6 ELISA.

In assessing TSG-6, the first attempt using the suggested maximum starting material weight resulted in all tested samples having components lower than the detectable limit. A second assay was performed using double the suggested maximum starting material, and the Tseng Product had low, but detectable TSG-6. TSG-6 was not detectable in the AMP. It was not possible to further increase the starting material volume due to space limitations in the assay wells.

Results

A summary of the average amount of components in each composition is listed in Table 1 below. The results demonstrate that the amount of total protein in AMP is about 10 times higher than that in the Tseng Product; the amount of elastin in AMP is about 15 times higher than that in the Tseng Product; and the amount of collagen in AMP is about 100 times higher than that in the Tseng Product. The amount of glycosaminoglycans in AMP is about 1 mg/g while there was no detectable glycosaminoglycans in the Tseng Product.

RT-PCR results demonstrated that both samples contained intact RNA, capable of being amplified (GAPDH); however no TSG-6 gene expression was detected.

Removal of RNA and DNA can be accomplished in an optional step: adding water to AMP to make a solution; adding RNase and DNase to the solution; incubating under suitable reaction conditions and then lyophilizing the resulting solution.

The resulting cumulative release curve (FIG. 26) demonstrated a significantly increased amount of protein released from AMP as compared with the Tseng Product. These differences were significant (p<0.001) at all time points.

The results of each of these assays are summarized in Table 1.

TABLE 1

|  | Tseng Product Data | AMP Data |
| --- | --- | --- |
| Total Protein | 19.75 ± 5.1 mg/g (1.97%) | 199.7 ± 44.2 mg/g (19.97%) |
| Elastin | 3.313 ± 0.2 mg/g (0.33%) | 48.5 ± 4.9 mg/g (4.85%) |
| Collagen | 4.7 ± 0.47 mg/g (0.47%) | 489 ± 38.4 mg/g (48.9%) |
| Glycosaminoglycans (GAGs) | Not Detected | 1.01 ± 0.13 mg/g (0.1%) |
| Tumor necrosis factor-stimulated gene 6 (TSG-6) | 1.85 ± 0.22 ng/g | Not Detected |
| Pentraxin 3 (PTX-3) | 0.03 ± 0.003 µg/g | 12.81 ± 2.6 µg/g |
| Thrombospondin-1 (TSP-1) | 24.74 ± 4.2 µg/g | 319.06 ± 92.5 µg/g |
| Total RNA | 38.1 ± 8.0 ng/mg | 1647.19 ± 129.4 ng/mg |
| TSG-6 Gene | Not Detected | Not Detected |
| Control (GAPDH) Gene | Detected | Detected |

In Vivo Study One

Study/Methods Overview

Animals:

Six Specific Pathogen Free (SPF) Yorkshire pigs were purchased and allowed to acclimatize for the required 2-week period. At the start of the study the pigs weighed approximately 40-50 kg. This study was reviewed and approved by the Wake Forest University Institutional Animal Care and Use Committee (A13-015-Amnion products for Wound Healing in Pigs).

Saddle Training:

Prior to surgery, the animals were trained to tolerate the plastic saddle. Animal crackers were provided as a distraction and incentive for human contact. First, the animals were acclimated to the odor of the plastic. Once acclimated, the saddle was placed on the animal under supervision for a period of time, gradually increasing the time until the animal was comfortable wearing the saddle indefinitely. The time with the saddle was gradually increased until the animal was fully accustomed to the plastic. This process typically takes 2-3 weeks (can be part of original 2 week period).

Full Thickness Wounds:

The animals were sedated and anesthetized with a combination of ketamine, xylazine, acepromazine, and were maintained under anesthesia using inhaled isoflurane via endotracheal tube. The anesthetized pigs had their backs depilated by shaving. The animals were immobilized and placed in a dorsal position. The animals were tattooed with eight 4×4 cm tattoos on the dorsum to denote the area of the excisional wound. The dorsal skin was cleaned with water and soap, and sterilized with β-iodine and 70% alcohol. For the creation of the defect, 8 areas of skin wound were created by removing 4×4 cm of full thickness skin in the central back along the thoracic and lumbar area. Incisions were made along the wound edges with a surgical blade to the panniculus carnosus layer and the overlying skin was excised (FIG. 1).

Wound Treatments:

Subsequently, the wound area was treated either with commercially available products according to the manufacturer's instructions, or with the presently invented amnion-derived products in a similar manner. An additional group underwent no treatment. The six experimental options were distributed over the 8 skin defects to control for differences in wound locations, resulting in a total of 8 applications of each product. The six pigs were treated in two rounds of experiments, where treatment of the second round was begun following euthanasia of the first round. Each experimental round ran for 30 days, during which the wounds were inspected 2 times each week for 1) documentation of wound size, re-epithelialization, and closure, and 2) cleaning, administration of antibiotics, and re-bandaging.

Hydrogel Preparation:

The amnion hydrogel used in this in vivo study one was prepared according to following steps:
1. IRGACURE® 2959 photoinitiator (4-(2-hydroxyethoxy)phenyl-(2-propyl)ketone, Sigma St. Louis, MO) was dissolved in sterile water to make a 0.05% w/v solution. HEPRASIL® (thiolated and heparinized HA-derivative) and GELIN-S® (thiolated gelatin) were dissolved in water to make 2% w/v solutions. EXTRALINK®, a PEGDA crosslinker, was dissolved in water to make a 4% w/v solution.
2. HEPRASIL®, GELIN-S®, and EXTRALINK® solutions are then mixed in a 2:2:1 ratio by volume.

Note: The resulting solution spontaneously crosslinks by a Michael-type addition thiol-acrylate reaction over the course of 15-30 minutes. This type of crosslinking is the normal crosslinking method described by the manufacturer. This time-frame is too slow to be implemented efficiently for wound care. Instead, the following crosslinking method is used.

3. The three components are mixed together, vortexed and applied to the desired target area as a liquid and irradiated with UV light (365 nm, 18 w/cm$^2$) to initiate a much faster thiol-ene stepwise crosslinking reaction.

Groups:
1. Untreated control
2. AMNIOGRAFT® (Bio-Tissue, Inc)
3. GRAFTJACKET® (Wright medical Technology, Inc.)
4. Amnion Powder, made according to the procedure described in present invention.
5. Amnion Hydrogel
6. Electrospun Patch Bandaging:

After treatment application and for scheduled bandage changes, the wound area was covered by dressing materials which helped to ensure that a protective barrier remained over the wound, as per the wound experiment protocols. The materials included a topical antibiotic cream, TEGADERM® (3M Company), cast padding, cohesive bandaging, stockinette, a protective plastic saddle, and finally a specially designed jacket to hold the bandage in place. The edges of the saddle were covered with porous surgical tape along the front of the saddle to protect the pig's neck. Four VELCO® straps were used to position a stretchable strap on the saddle as a means to secure it to the pig.

Figure 2:
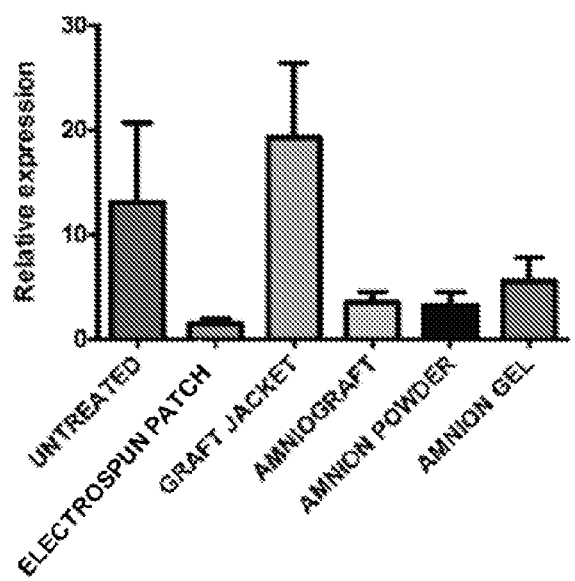
FIG. 2 is a set of images illustrating the steps of imaging and tissue harvesting. Panels A-C illustrates the steps of tissue harvesting. Panels D and E illustrate ex vivo analysis.

Euthanasia:

At 30 days post-treatment, the study was terminated and the wound areas were harvested. Animals were sedated with ketamine, xylazine, and acepromazine. The animal was then brought to the necropsy room. A lethal overdose of beuthanasia was given by intravenous injection. Wounds from each animal were each split into 4 quarters: two for histology and immunohistochemistry, one for PCR analysis of wound healing biomarkers, and one for protein assays (FIG. 2).

Figure 3:
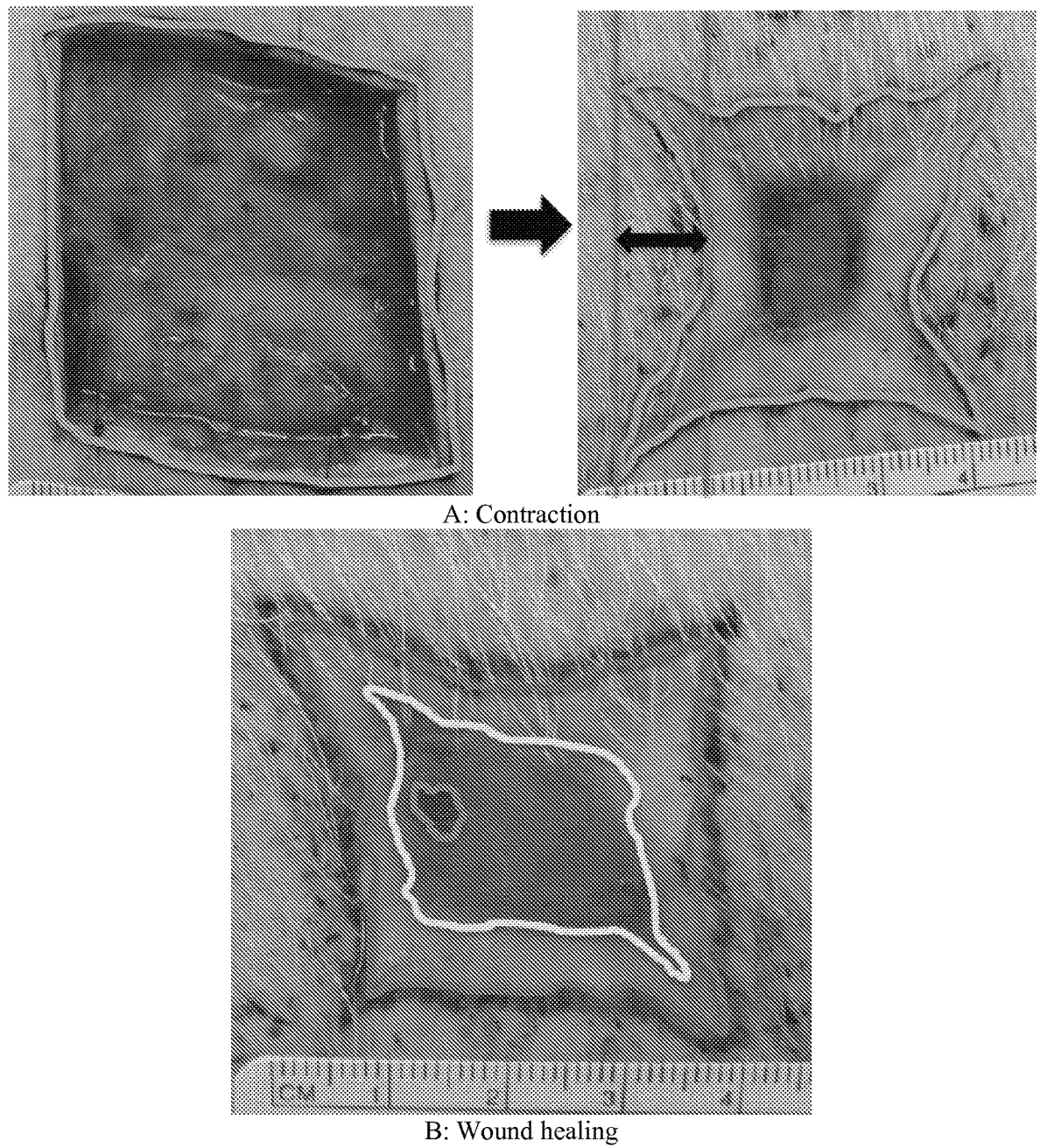
FIG. 3 illustrates image analysis methodology. Panel A illustrates contraction measured by the area defined by the tattoo (purple) at each time-point. Contraction ratio is the measurement of the shape change that occurs during wound contraction. Panel B illustrates wound closure and epithelialization determined by measuring the area of open wound (red), immature epithelium (yellow), and mature epithelium (green).
Figure 4:
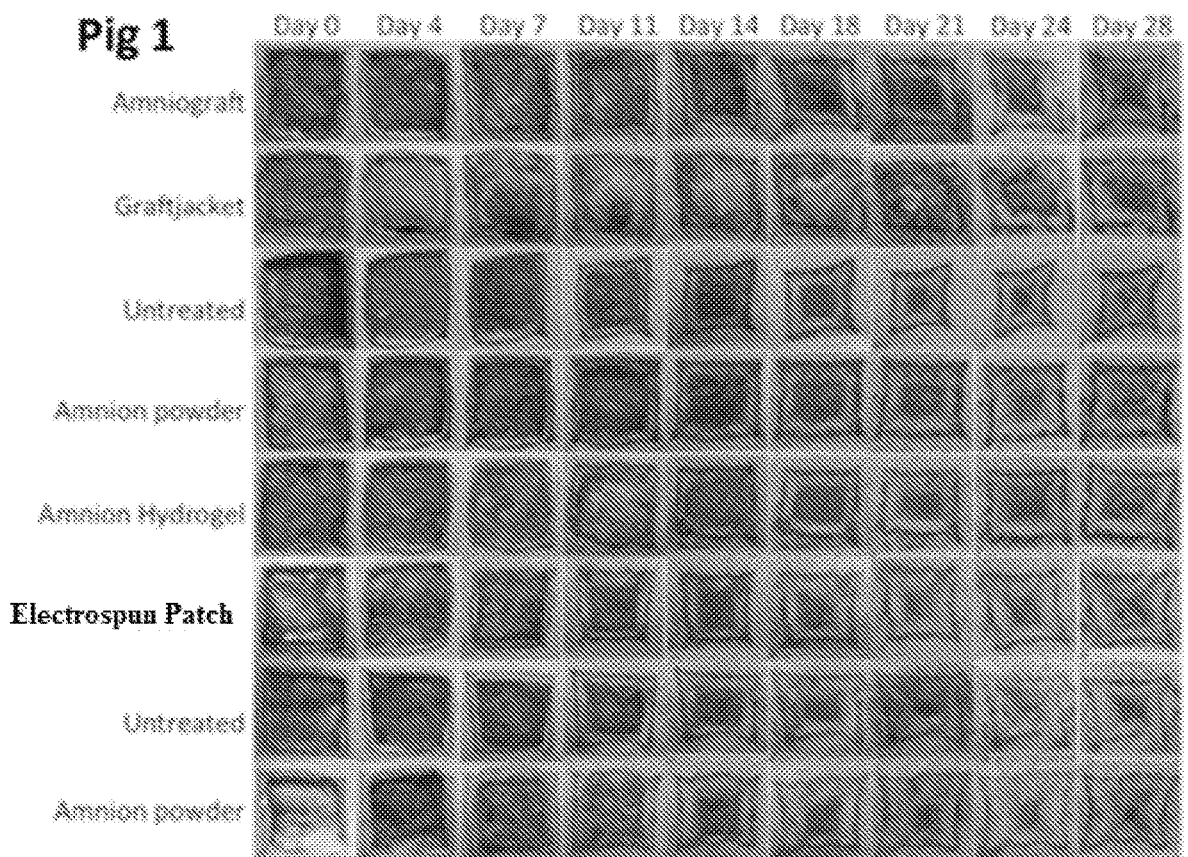
FIG. 4 is a set of images illustrating wounds from Pig 1 at different time points under different treatments.
Figure 5:
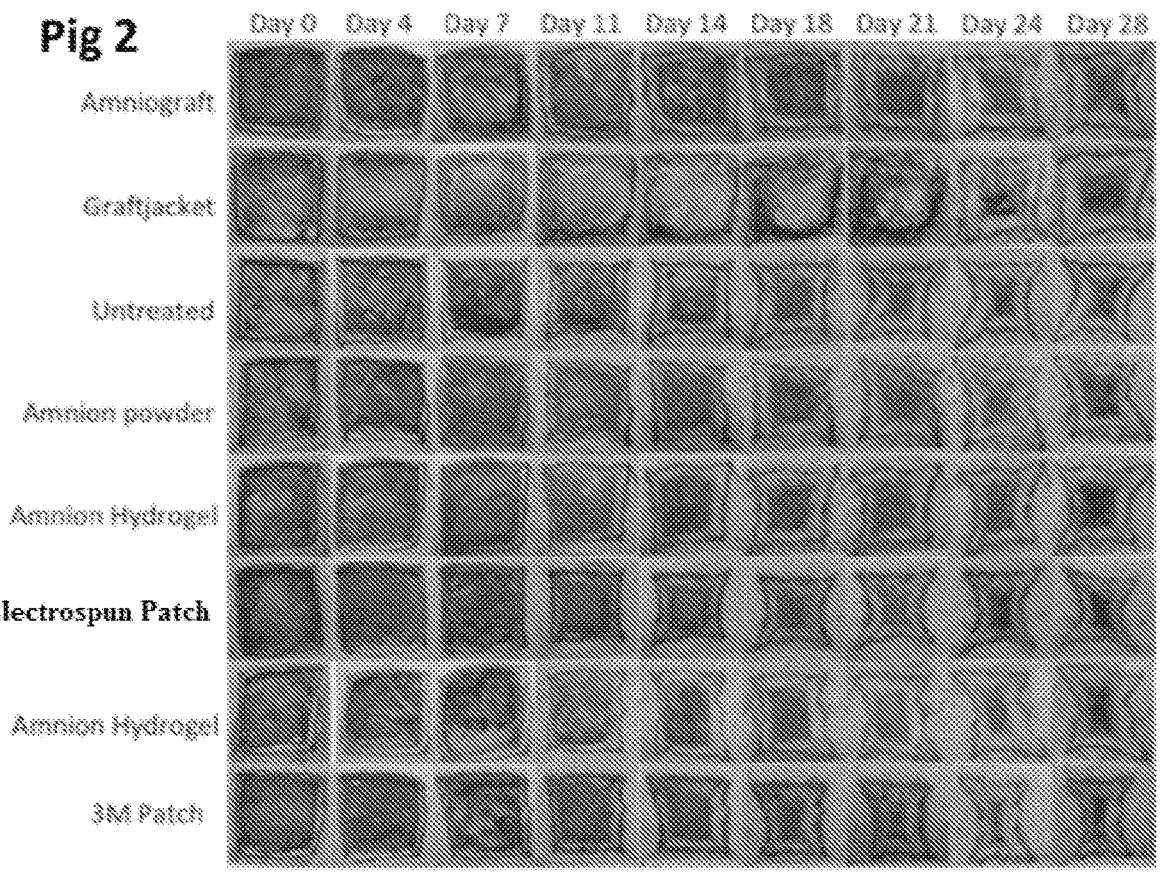
FIG. 5 is a set of images illustrating wounds from Pig 2 at different time points under different treatments.
Figure 6:
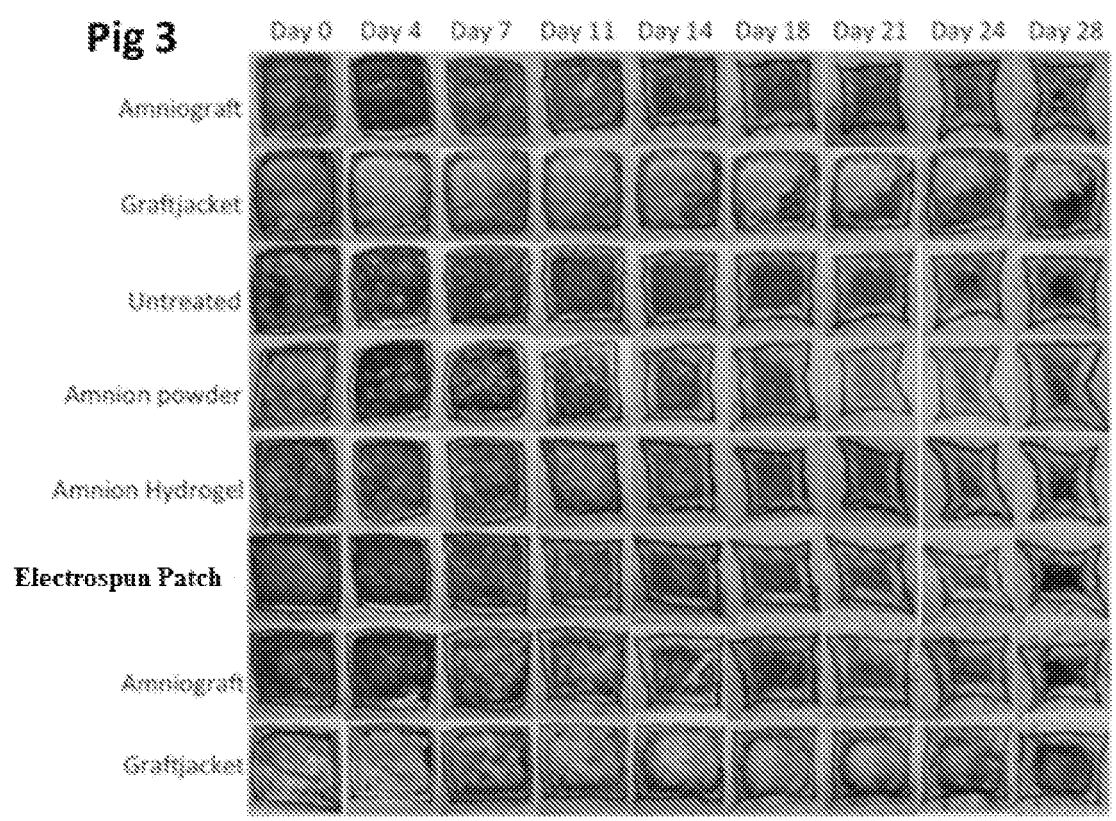
FIG. 6 is a set of images illustrating wounds from Pig 3 at different time points under different treatments.
Figure 7:
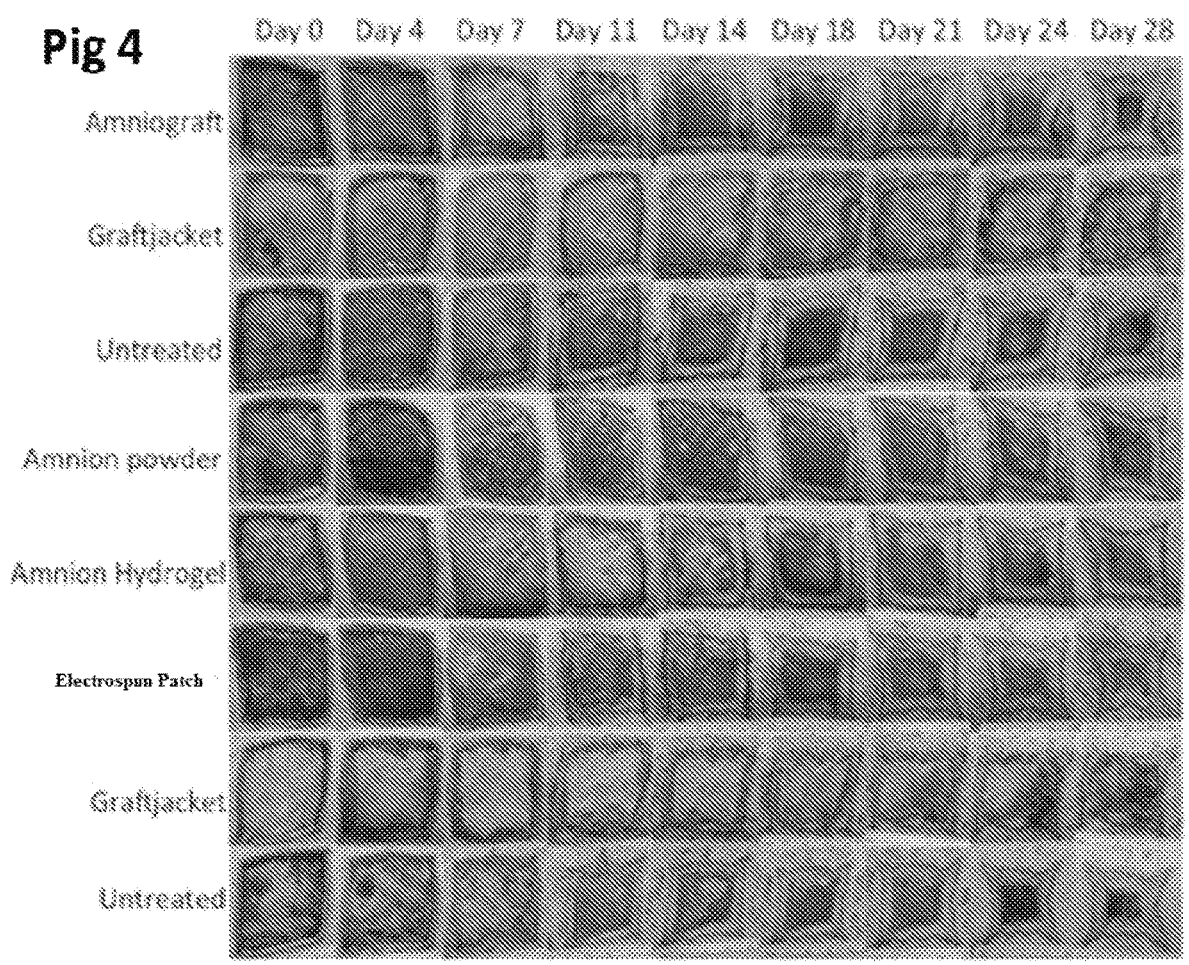
FIG. 7 is a set of images illustrating wounds from Pig 4 at different time points under different treatments.
Figure 8:
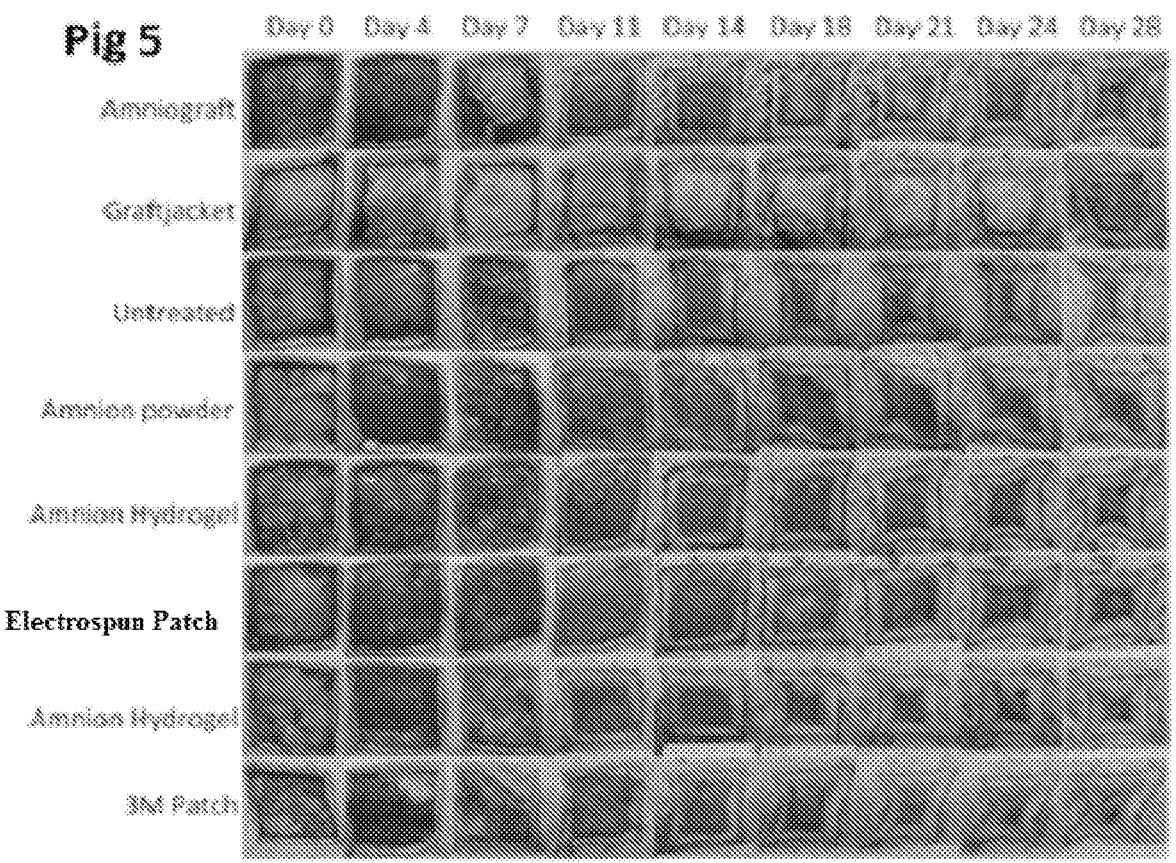
FIG. 8 is a set of images illustrating wounds from Pig 5 at different time points under different treatments.
Figure 9:
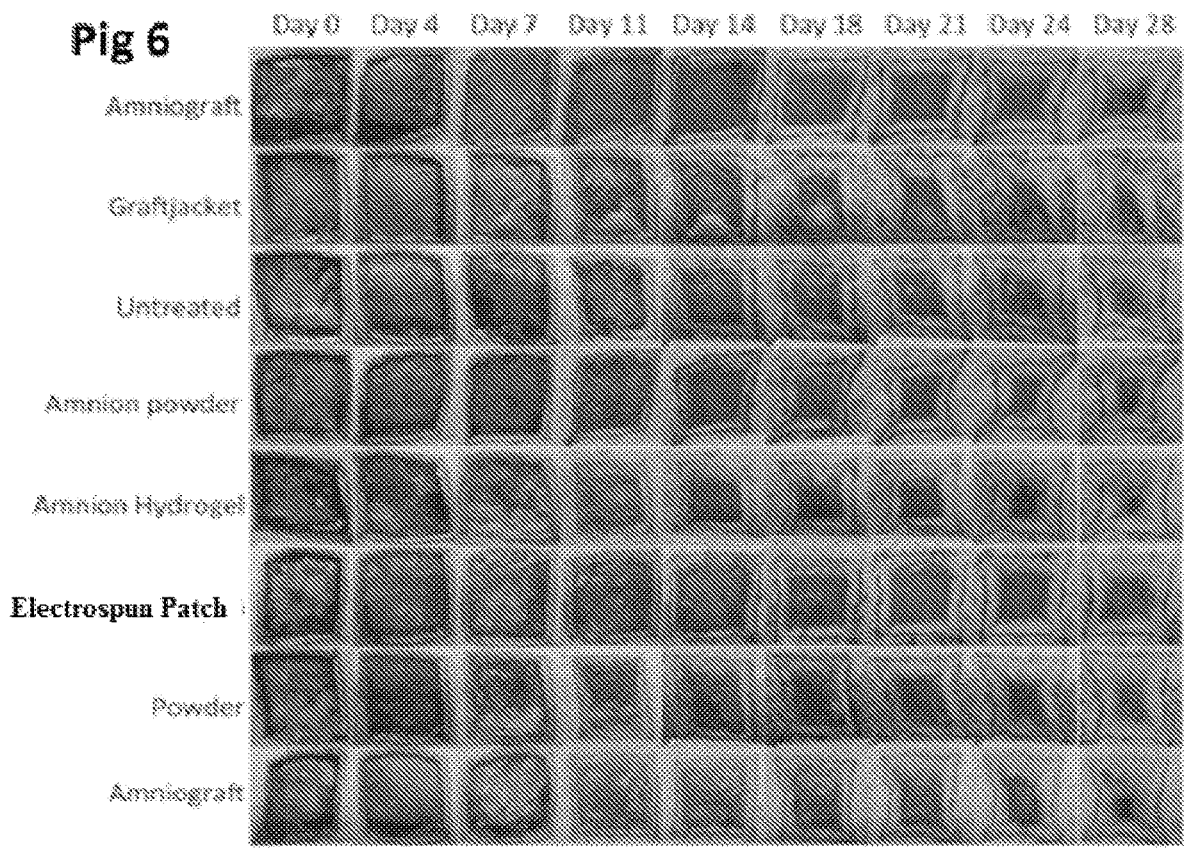
FIG. 9 is a set of images illustrating wounds from Pig 6 at different time points under different treatments.

Image Analysis:

Contraction was measured at each of the time-points by measuring the area inside the tattooed square using the software ImageJ and expressed relative to original tattoo size. A wound contraction ratio has been used in previous studies as an additional means to describe contracted wounds. In addition to the previously discussed wound contraction area measurement, the wound contraction ratio describes the extent of which the wound has changed shape from the initial square wound. Wounds that heal by re-epithelialization normally maintain their initial square shape while contracting slightly and symmetrically. However, highly contractile wounds, usually contract from the edges of the wound, resulting in a star shaped wound. Wound closure and epithelialization was measured by using ImageJ to determine the area of open wound, mature, and immature epithelium, which can be identified by color and texture of the healing wound. Generally open wounds were dark red and shiny, immature epithelium was light red and opaque/matte (due to a thin epidermis covering), and mature epithelium was white/pink and opaque/matte. These components were measured expressed as individual measurements relative to the original wound size, and combined to demonstrate the contribution of all components to the wound healing over time (FIG. 3).

TABLE 2

Wound Distribution

| Pig | Front right Wound 1 | Wound 2 | Wound 3 | Rear Right Wound 4 | Front Left Wound 5 | Wound 6 | Wound 7 | Rear Left Wound 8 |
| --- | --- | --- | --- | --- | --- | --- | --- | --- |
| #1 | Untreated | Powder | Amnion Hydrogel | Electrospun Patch | AMNIOGRAFT® | GRAFTJACKET® | Untreated | Powder |
| #2 | Electrospun Patch | Amnion Hydrogel | Powder | Amnion Hydrogel | Electrospun Patch | AMNIOGRAFT® | GRAFTJACKET® | Untreated |
| #3 | AMNIOGRAFT® | GRAFTJACKET® | Untreated | Powder | Amnion Hydrogel | Electrospun Patch | AMNIOGRAFT® | GRAFTJACKET® |
| #4 | GRAFTJACKET® | Untreated | GRAFTJACKET® | Untreated | Powder | Amnion Hydrogel | Electrospun Patch | AMNIOGRAFT® |
| #5 | Amnion Hydrogel | Electrospun Patch | AMNIOGRAFT® | GRAFTJACKET® | Untreated | Powder | Amnion Hydrogel | Electrospun Patch |
| #6 | Powder | AMNIOGRAFT® | Electrospun Patch | AMNIOGRAFT® | GRAFTJACKET® | Untreated | Powder | Amnion Hydrogel |

Histology and IHC:
1) H&E staining
2) Pentachrome staining for collagen, mucins/GAGs, elastin and mature fibers
3) Sirius Red staining for mature and immature collagens
4) Alcian Blue stain for mucins/GAGs
5) Iron colloid for mucins/GAGs
6) Immunohistochemistry for Collagen Type I and Collagen Type III
7) Immunohistochemistry Neutrophil infiltration Wound Healing Biomarkers:

Quantitative PCR was performed for biomarkers of healing and non-healing wounds, including inflammatory markers of non-healing wounds (IL1 alpha, IL1 beta and IP-10), Monocyte-related inflammatory markers (MCP-1, MIP-1 beta and IL-8) and anti-inflammatory markers of healed wounds (IL2, IL-4 and IL-5). These markers were selected due their success in predicting wound healing or requirement for debridement in human patients. Gene expression from all treatments was expressed relative to normal healthy skin.

Biomarkers were selected based on data in the publication: Hawksworth, J. S. et al. *Inflammatory biomarkers in combat wound healing. Ann Surg* 250, 1002-1007 (2009).

Protein Analysis:

Protein was isolated from a section of skin corresponding to a quarter of the harvested tissue.

Results

General Observations

All surgical procedures were performed without complications. Wounds were created with a uniform size and depth, although some 'sagging of the skin was observed following removal of the square skin section. Wound treatment products were generally easy to administer. AMNIOGRAFT® was the most difficult to apply due to the thin and fragile nature of the product, and difficulties removing from the backing paper. This product required 4 hands to ensure it did not roll up on itself or fold, which occurred on several occasions. GRAFTJACKET® was easier to administer due to its thickness, however the size of this product did vary and positioning and suturing was difficult. The Electrospun Patch was the easiest of the 3 'patch-type' products to administer with an intermediate thickness and stiffness. Significant variation was observed in the Electrospun Patch product, especially with the final 4 patches received (applied to round 2 animals). These patches had areas of inconsistent coloration, with dark blotches resembling a semi-dried liquid. The Amnion Hydrogel was easy to apply by one person and did not require any contact with the wounds. Amnion liquid was applied by syringe with one hand and the UV light held approximately 5 cm above the wound surface. As expected the liquid rapidly formed a gel within the wound and filled the entire wound area in 10-15 seconds. Amnion Powder was the easiest product to administer. A measured dose of powder was evenly distributed by tapping the tube gently over the wound, followed by the application of 1 mL of sterile saline to wet the powder. In In Vivo Study Two described below, the powder was suspended in 1 mL of saline before application and then applied directly to the wound as a liquid to the three pigs. No differences were detected between each method of delivery for any measured parameters.

Image Analysis:

Digital photos were taken for each of the time-points (Days 0, 4, 7, 11, 14, 18, 21, 24 and 28) and compiled for each of the 8 wounds (FIGS. 4-9). Note: Wound-healing distribution is described in Table 2 above. Treatment options are kept in the same order for each animal for ease of comparison. The lower 2 treatments on each pig are the repeated 2 treatment options for that pig.

Figure 10:
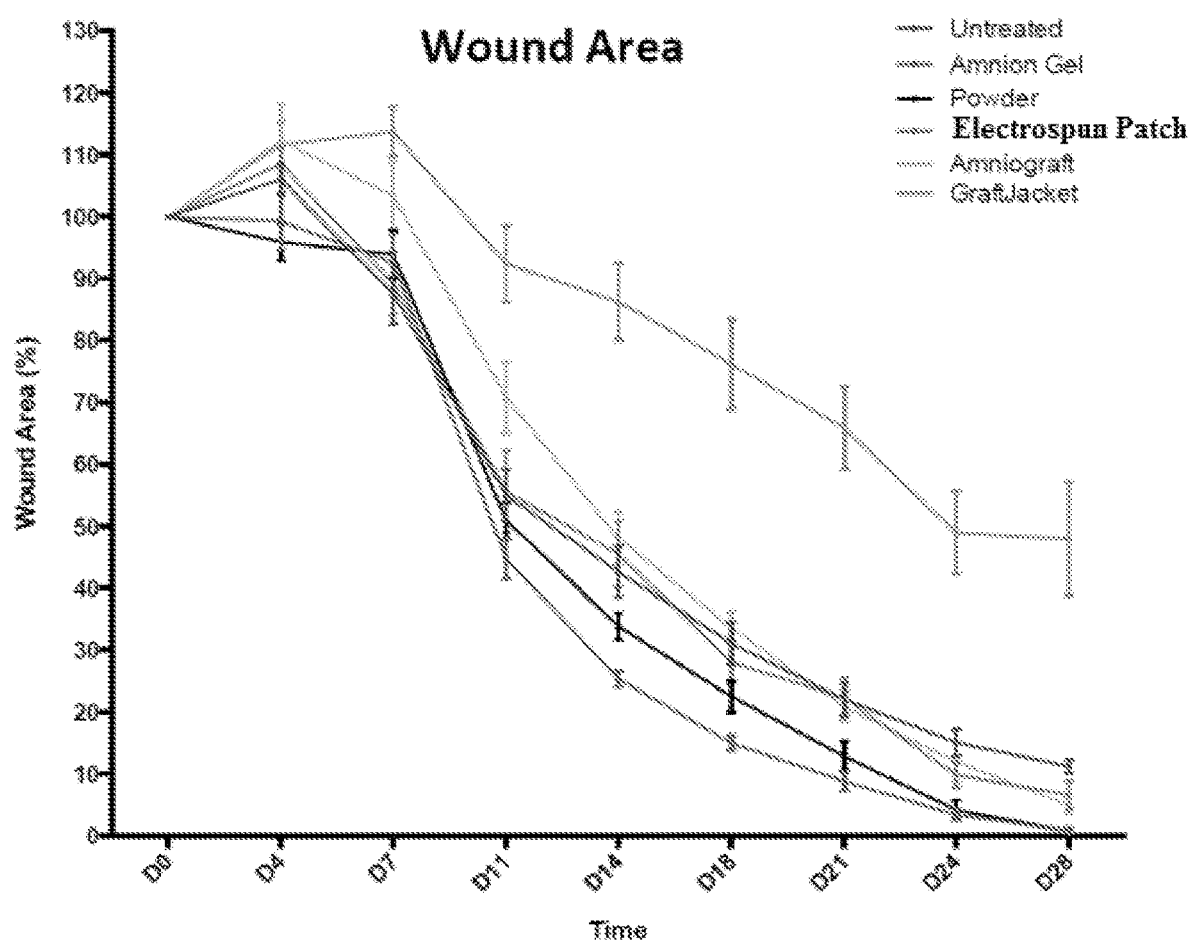
FIG. 10 is a graph illustrating the change of wound area at different time points under different treatments.

Wound Closure:

Wound closure correlates with successful wound healing. The higher the wound closure rate, the better healing outcome. Wound closure was measured for each time-point and expressed as a percentage of the wound present as relative to the original wound area (FIG. 10). The graph in FIG. 10 demonstrates that Amnion Hydrogel is the best performing for wound closure; Amnion Powder is the second best performing; Untreated, Electrospun Patch and AMNIOGRAFT® are in the middle, and GRAFTJACKET® is the worst performing. Average wound size was 17.6 cm$^2$ with no significant differences between treatments or pigs. This area was slightly larger than the initial 16 cm$^2$ area tattooed due to skin drooping following incisional wounding. This small difference had no effect on treatment administration. In the immediate time-point following wound treatment there was an initial increase of the wound area for the Untreated, GRAFTJACKET®, AMNIOGRAFT® and Electrospun Patch-treated wounds due to wound stretching/drooping. This suggests that application of these treatments do not immediately stabilize the wound area. In contrast Amnion Hydrogel and Amnion Powder-treated wounds did not show any significant increase in wound size. While the hydrogel is likely to have a role in stabilizing the wound area, this does not account for the effect in the Amnion Powder group. An earlier onset of granulation, which was observed for these groups at early time-points may account for this observation. Amnion Hydrogel and Amnion Powder-treated groups showed a consistent decrease in wound area from Day 0, with all other groups decreasing from Day 4-7 onwards. GRAFTJACKET®-treated regions showed the slowest rate of wound closure, with the product forming a hard scab like structure within the wound, preventing closure. Over time this product either degraded or dried and fell off the wound, facilitating closure of approximately 50% by the end of the study. AMNIOGRAFT®-treated wounds appeared to have a slightly delayed wound closure rate, but by day 14 showed similar wound closure to the Untreated and Electrospun Patch-treated wounds (~50%). These three products continued to promote wound closure resulting in approximately 10% wound area at the end of the study. Amnion Powder-treated wounds showed improved wound closure compared to these products with 10-15% acceleration of wound closure compared to AMNIOGRAFT®, Untreated and Electrospun Patch-treated wounds from Day 14 onwards. Amnion Hydrogel-treated wounds performed better than Amnion Powder-treated wounds between Day 11 and Day 24, showing at 25% wound area at Day 14. By Day 28 both Amnion Powder and Amnion Hydrogel-treated groups showed almost 100% wound closure, which was a 10% improvement over next best performing product and a 50% improvement over the least best performing product.

Figure 11:
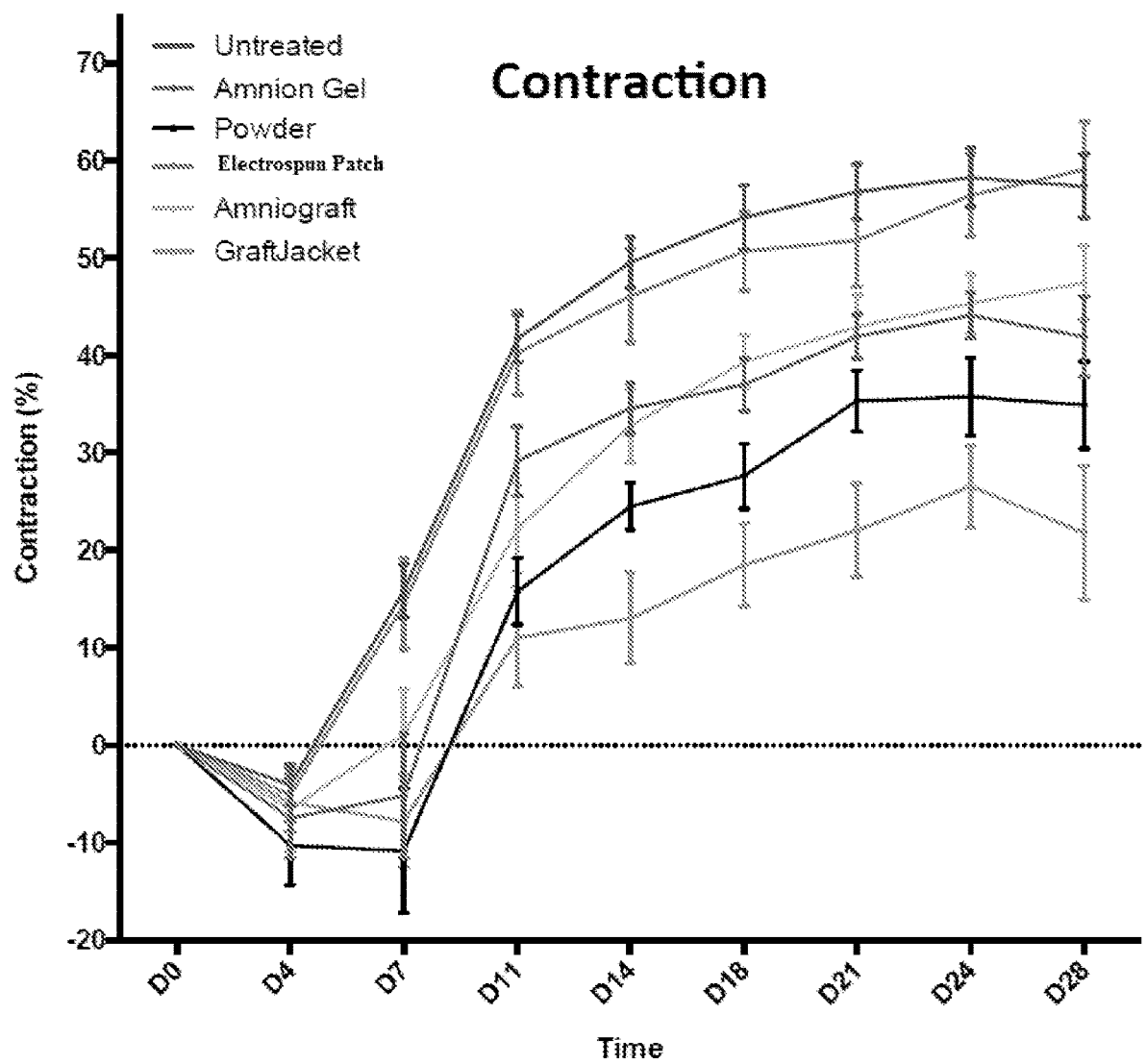
FIG. 11 is a graph illustrating the changes of wound contraction at different time points under different treatments.

Wound Contraction:

Wound contraction correlates with wound healing effectiveness. The higher the contraction rate, the worse the healing outcome. Wound contraction was measured for each time-point by measuring the area within the tattoo border and expressing the measurement as a percentage of the area relative to the original tattoo area (FIG. 11). The graph in FIG. 11 demonstrates that Untreated and Electrospun Patch are the most contracted; Amnion Hydrogel and AMNIOGRAFT® contract moderately; Amnion Powder is less contracted than Amnion Hydrogel and AMNIOGRAFT®; and GRAFTJACKET® contracts the least.

As with the wound closure data, an initial increase in the wound/tattoo area over the first 7 days was observed. This resulted in an initial negative contraction percentage of approximately 10%. Untreated and Electrospun Patch-treated wounds showed the most contraction, with rapid contraction occurring between Day 4 and Day 11, reaching approximately 40% of the original tattoo area. At the final time-point, these products showed 50-60% contraction. These measurements were consistent with observations throughout the study, where these treatments appeared to significantly contract the wounds over almost every time-point.

The next grouping of products were the Amnion Hydrogel and AMNIOGRAFT®-treated wounds, which showed a similar trend to the Untreated and Electrospun Patch-treated wounds, but with a delayed increase in contraction and a shorter and less rapid contraction period between Day 7 and Day 11 reaching a contraction of 20-30%. At the final time-point, these products showed 35-45% contraction. Amnion Powder performed better than these products with approximately 10% contraction by Day 11 and 30% contraction by Day 28.

GRAFTJACKET®-treated wounds had the least amount of contraction over most time-points. However this is due to the stiff, scab like structure formed by the product that both prevented wound closure and contraction.

Figure 12:
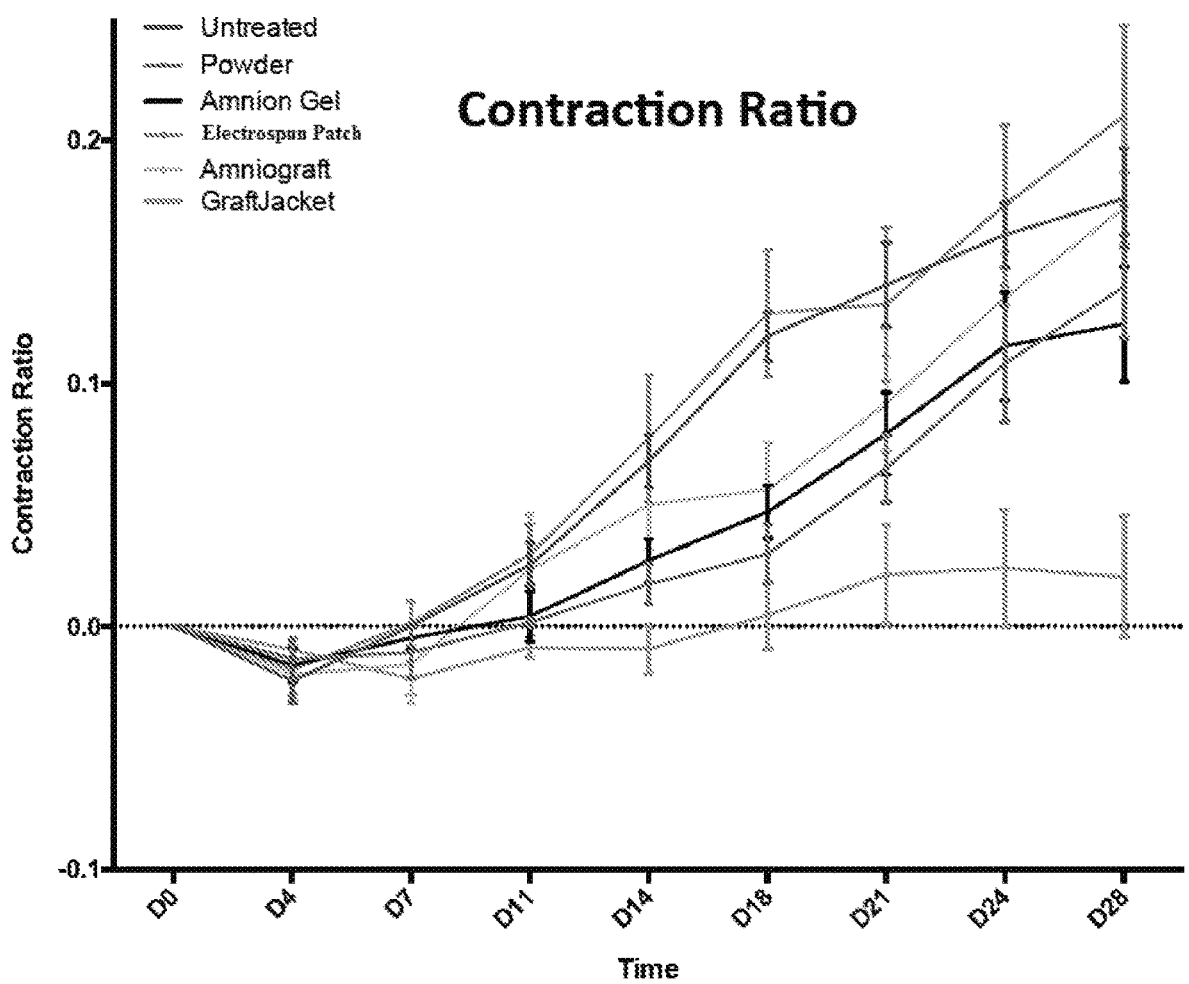
FIG. 12 is a graph illustrating the changes of the contraction ratio at different time points under different treatments.

Wound Contraction Ratio:

To measure this phenomenon several measurements of the wounds over all time-points were performed (FIG. 12). The distance of the left edge of the wound to the center point between the two left wound corners was measured and expressed as a ratio of the total distance between these corners. This ratio gives an approximate description of the amount of wound shape change. For reference, non-contracted square wounds had a ratio close to 0, while highly contracted 'star' shaped wounds had a ratio close to 0.2. Confirming contraction data, the ratio of Untreated and Electrospun Patch-treated wounds increased to approximately 0.2 over 28 days. Amnion Powder, Amnion Hydrogel and AMNIOGRAFT®-treated wounds all increased to a lesser extent, while GRAFTJACKET®-treated wounds only had a moderate increase of contraction ratio.

Figure 13:
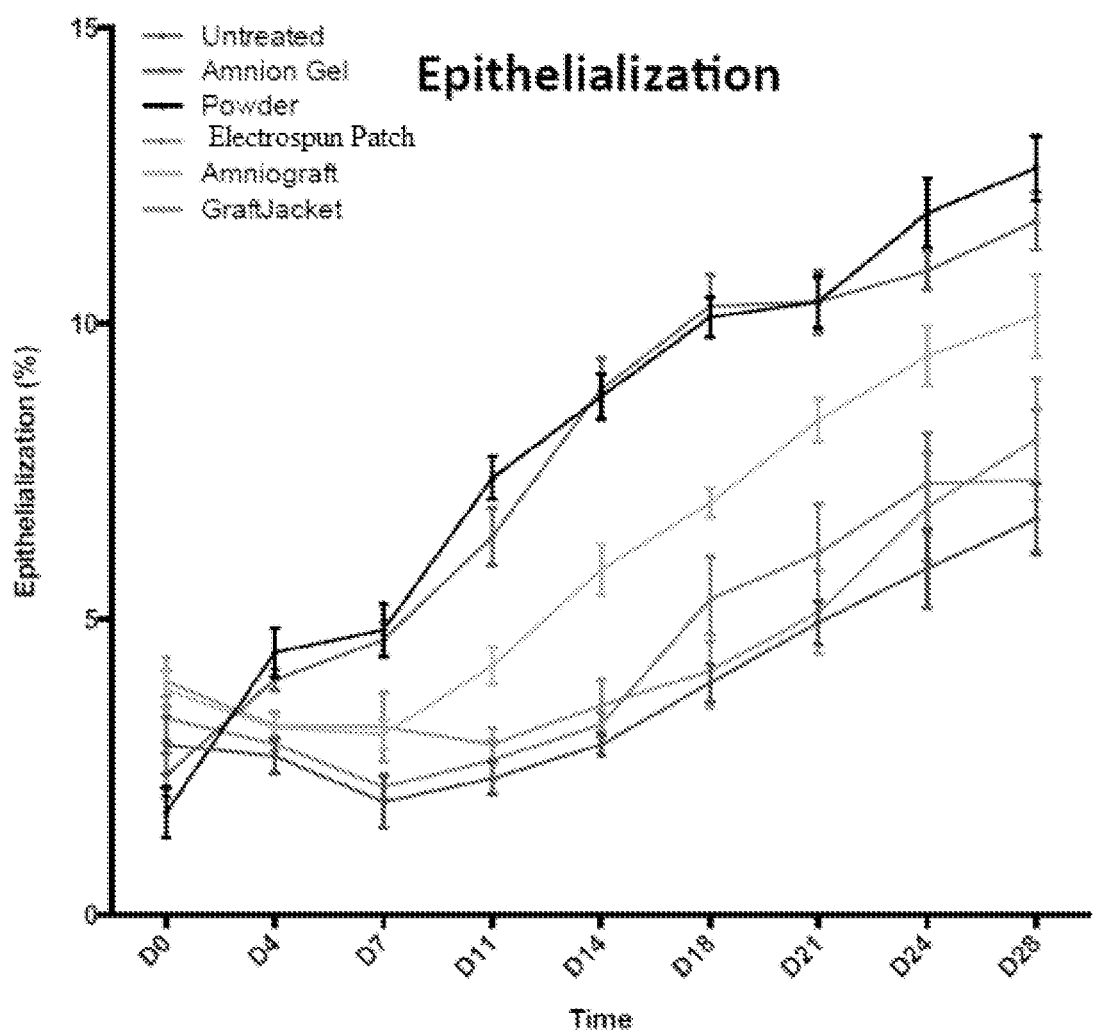
FIG. 13 is a graph illustrating the changes of epithelialization at different time points under different treatments.

Wound Epithelialization:

Wound epithelialization correlates with wound healing success. The higher the epithelialization rate, the better the wound heals. Epithelialization was measured at all time-points with mature and immature epithelium defined by the color (mature: white, immature: pink), and presence of a matte appearing epithelial coating distinct from the wound area. The graph in FIG. 13 illustrates Amnion Hydrogel and Amnion Powder treated wounds showing greatest amount of epithelialization. All tissues initially had some level of epithelialization due to the incisional wound being created inside the tattoo line. This initial area was consistent over all treatments and pigs. Untreated, Electrospun Patch and GRAFTJACKET®-treated wounds all showed the least wound epithelialization, showing a very slow onset of epithelialization (~2-3% at Day 14) and a low total epithelialization (~5-7%) at the end of the study. AMNIOGRAFT®-treated wounds showed an average level of wound epithelialization, with a slower initial epithelialization (5% at Day 14) and approximately 10% at the end of the study. Amnion Hydrogel and Amnion Powder-treated wounds were the best performing for total wound epithelialization, showing a rapid initial epithelialization reaching approximately 8-10% by Day 14 and 12% by the end of the study. These groups were significantly better than all other treatments at every time-point.

Figure 14:
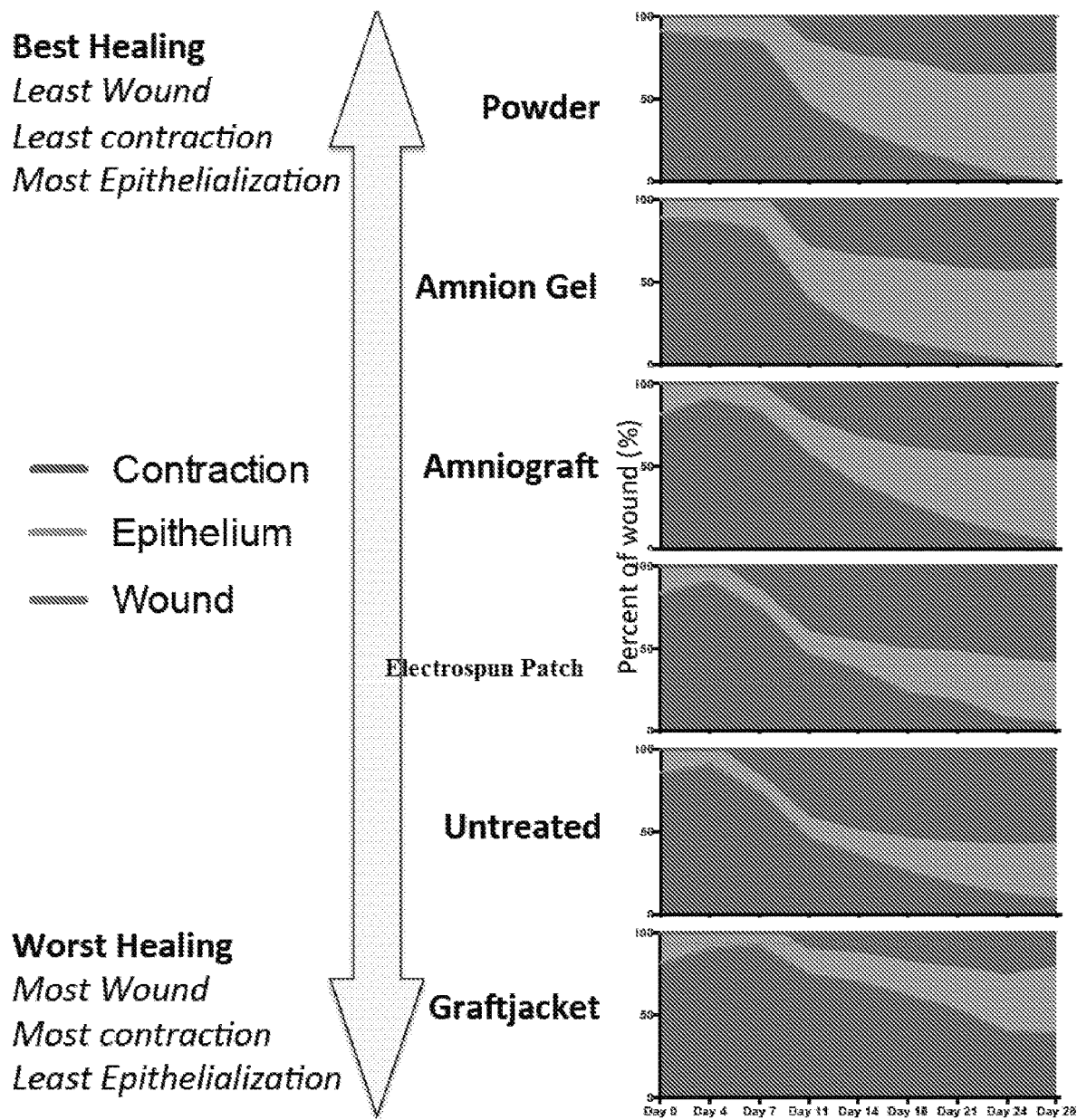
FIG. 14 is a set of graphs illustrating a combination of each individual component of the wound area during healing. Wound size (red), epithelialization (green) and contraction areas (blue) are shown. Products are ranked from the best healing (top) to worst healing (bottom).

Combined Analysis of Wound Area, Contraction and Epithelialization:

While important information can be gained from analyzing individual components of wound healing mechanisms, it is only by looking at the complete picture of the wound during healing that an accurate representation of the quality of healing can be obtained. To achieve this, the total wound area at each time-point divided into the percentage of wound area is represented, percentage contraction and percentage epithelialization (FIG. 14).

With these three measured components fully describing the healing wound over time, the competing mechanisms of contraction and epithelialization for each treatment can be observed. Ranking of each treatment was performed with the criteria for best healing as: small wound area, least contraction, and most epithelialization. Criteria for worst healing were; large wound area, most contraction, and least epithelialization. The graphs in FIG. 14 demonstrates that Amnion Powder and Amnion Hydrogel had significantly less wound, less contraction and more epithelialization compared to other products.

These data highlight the importance of the type and quality of wound healing, as contraction may result in a decrease in wound area, but also leads to disfigurement, scarring and loss of function. For this reason, wound closure by re-epithelialization is most desirable as this results in a rapid restoration of the skin barrier, with optimal cosmetic and functional outcomes. While GRAFTJACKET®-treated wounds showed minimal contraction, they also showed very little epithelialization, resulting in a persistent open wound area. For this reason GRAFTJACKET® ranked last of the products tested. AMNIOGRAFT®, Electrospun Patch and Untreated wounds grouped together next best performing products, with AMNIOGRAFT® having a faster rate of wound closure, driven by approximately 50% contraction and 50% epithelialization. Electrospun Patch and Untreated wounds had a similar rate and extent of wound closure compared to AMNIOGRAFT®, however with the majority of this closure driven by contraction. Amnion Powder and Amnion Hydrogel were the best performing products using these criteria, with the most rapid and complete closure of the wounds, which was driven by increased epithelialization and minimal contraction.

Histological Analysis

Figure 15:
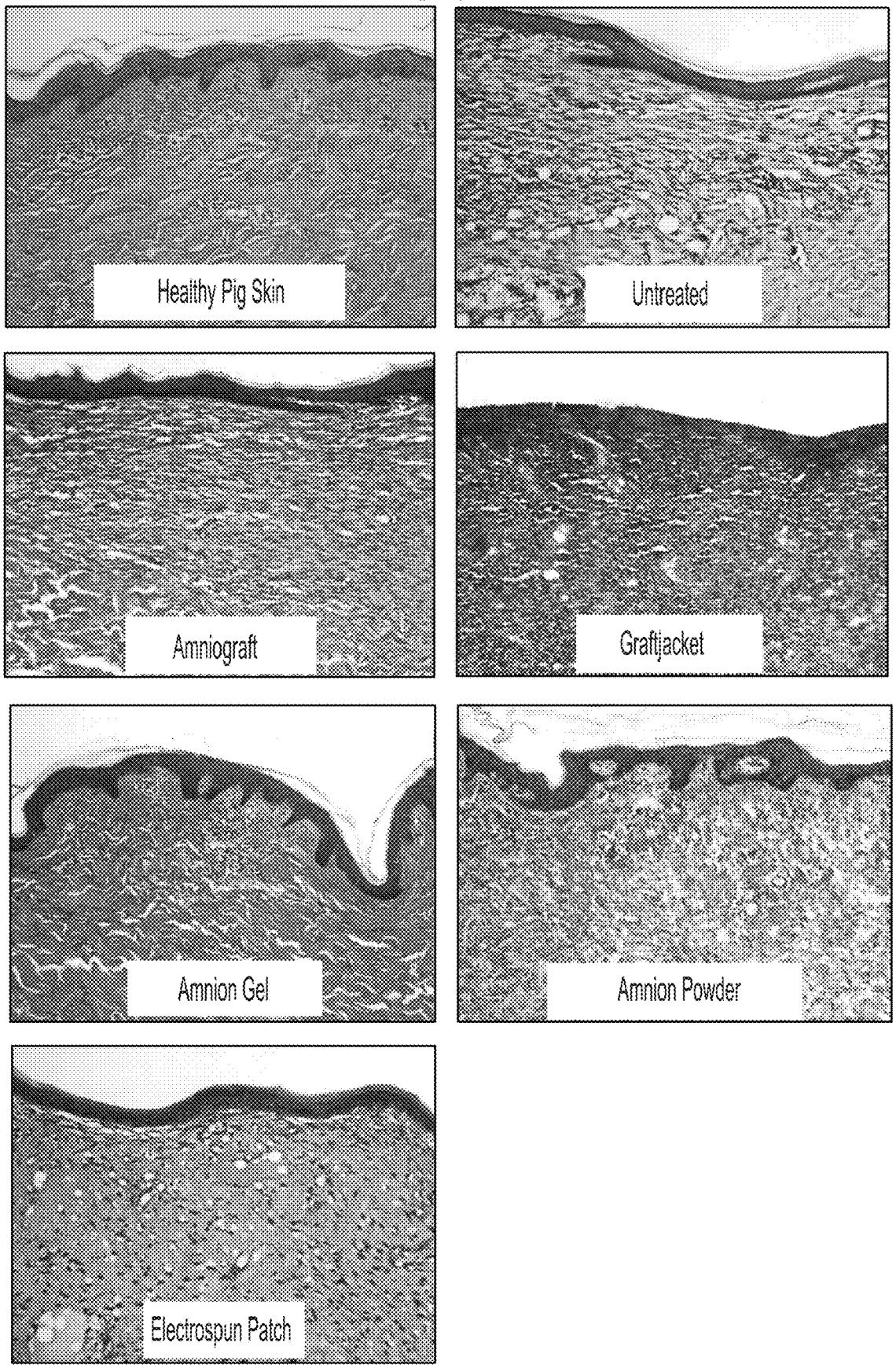
FIG. 15 is a set of images illustrating Hematoxylin and Eosin (H&E) stained histological images for pigs 1-3.
Figure 16:
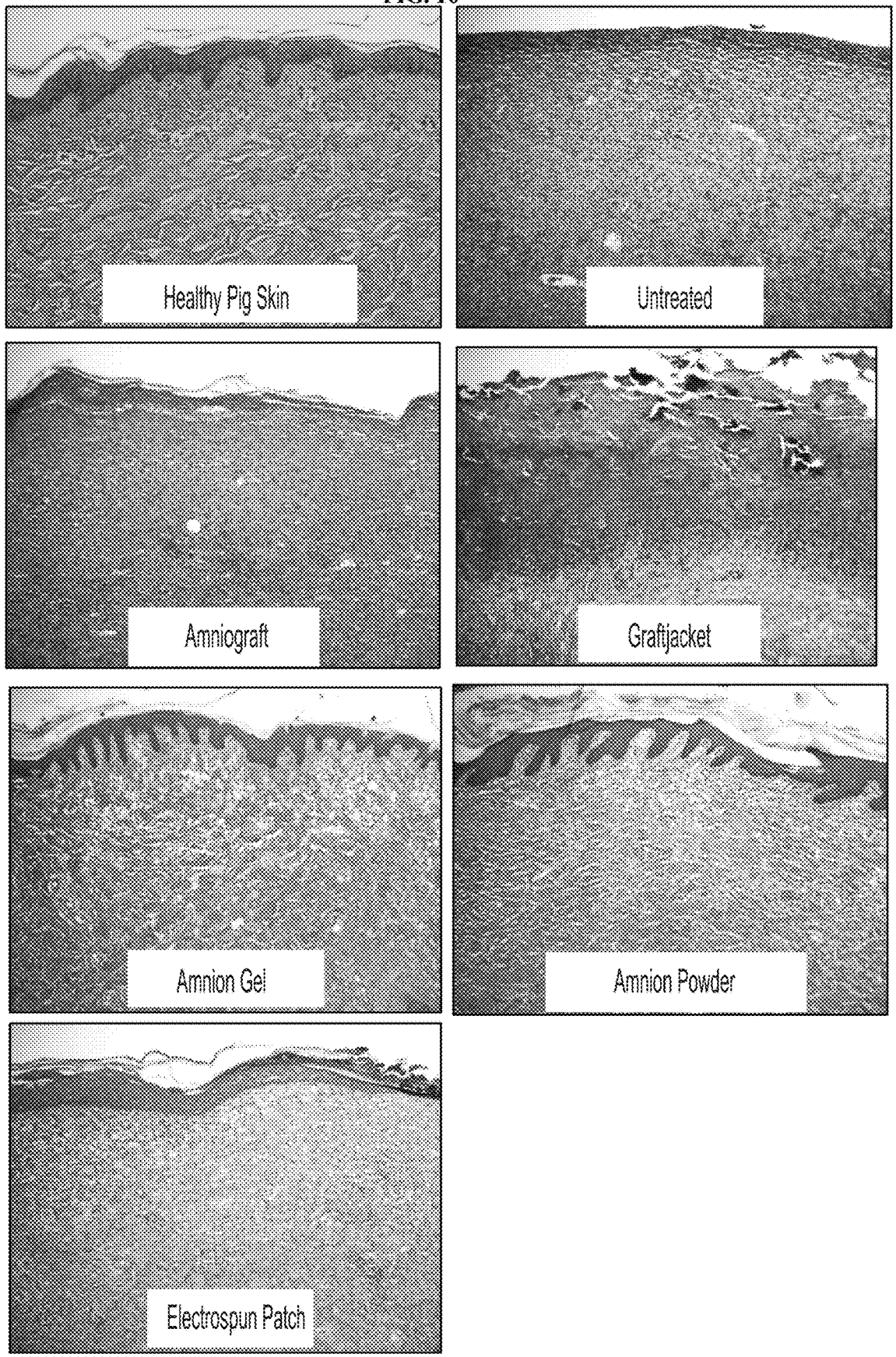
FIG. 16 is a set of images illustrating Hematoxylin and Eosin (H&E) stained histological images for pigs 4-6.

Hematoxylin and Eosin stained sections were used to evaluate and compare the general structure and composition of each of the wounds. Representative images from pigs 1-3 are shown in FIG. 15 and from pigs 4-6 in FIG. 16. Healthy pig skin was used as a control for this analysis. Analysis of wounds from pigs 1-3 revealed that most wounds has some degree of epidermal covering with the exception of GRAFTJACKET®. GRAFTJACKET®-treated wounds generally had an exposed dermis, or coverage with a variably deep scab-like tissue. Untreated, AMNIOGRAFT®, and Electrospun Patch-treated wounds appeared to have inconsistent coverage, a thinner epidermis, and lacked noticeable epithelial 'finger-like' protrusions into the dermal area (rete pegs). The epidermis from Amnion Hydrogel and Amnion Powder-treated wounds looked similar to healthy skin in regards to the coverage, thickness and presence of rete pegs. The dermis of healthy skin consisted of large organized fibers that were light pink in color, with only minimal disorganized, thin, purple fibers. GRAFTJACKET®-treated wounds appeared to contain many small cells with an appearance of inflammatory and fibrous cells. This transitioned into a thick fibrous tissue at the surface of the wound. Untreated and Electrospun-patch treated wounds did not show any organization of the dermal fibers, and consisted completely of small, purple unorganized fibers. AMNIOGRAFT®-treated wounds had some unorganized large pink fibers present in the dermis, but this was inconsistent between wounds, and also within individual wounds, with some areas dominated by the small, purple unorganized fibers. Amnion Hydrogel-treated wounds appeared most similar to healthy skin with only slightly more unorganized fibers. Amnion Powder-treated wounds seemed somewhat similar to healthy skin in the presence of large pink fibers, but the organization of these fibers was inconsistent between groups.

Pigs 4-6 had a very similar histological appearance to pigs 1-3. This analysis confirmed that Amnion Hydrogel and Amnion Powder-treated wounds had a very mature appearing epidermis with regular rete pegs. Some Untreated wounds did not have a consistent epidermis, while some Electrospun Patch-treated wounds showed thicker epidermal coverage, but without any rete pegs. AMNIOGRAFT® and GRAFTJACKET®-treated wounds were consistent with the first three pigs. Amnion Hydrogel and Amnion Powder-treated wounds both appeared to have a dermis very similar to that of healthy skin, with highly organized fibers that were light pink in color, and only minimal unorganized small fibers. The dermis of Untreated, AMNIOGRAFT® and Electrospun Patch-treated wounds seemed similar to that observed for pigs 1-3. Overall it appears that histologically, Amnion Hydrogel and Amnion Powder-treated wounds looked most similar to healthy skin. Untreated, AMNIOGRAFT® and Electrospun Patch-treated wounds all appeared to be progressing toward normal healing, but had an immature epidermis and unorganized dermis. Grafjacket-treated wounds appeared inflammatory and did not show signs of a developing epidermis or dermis.

Figure 17:
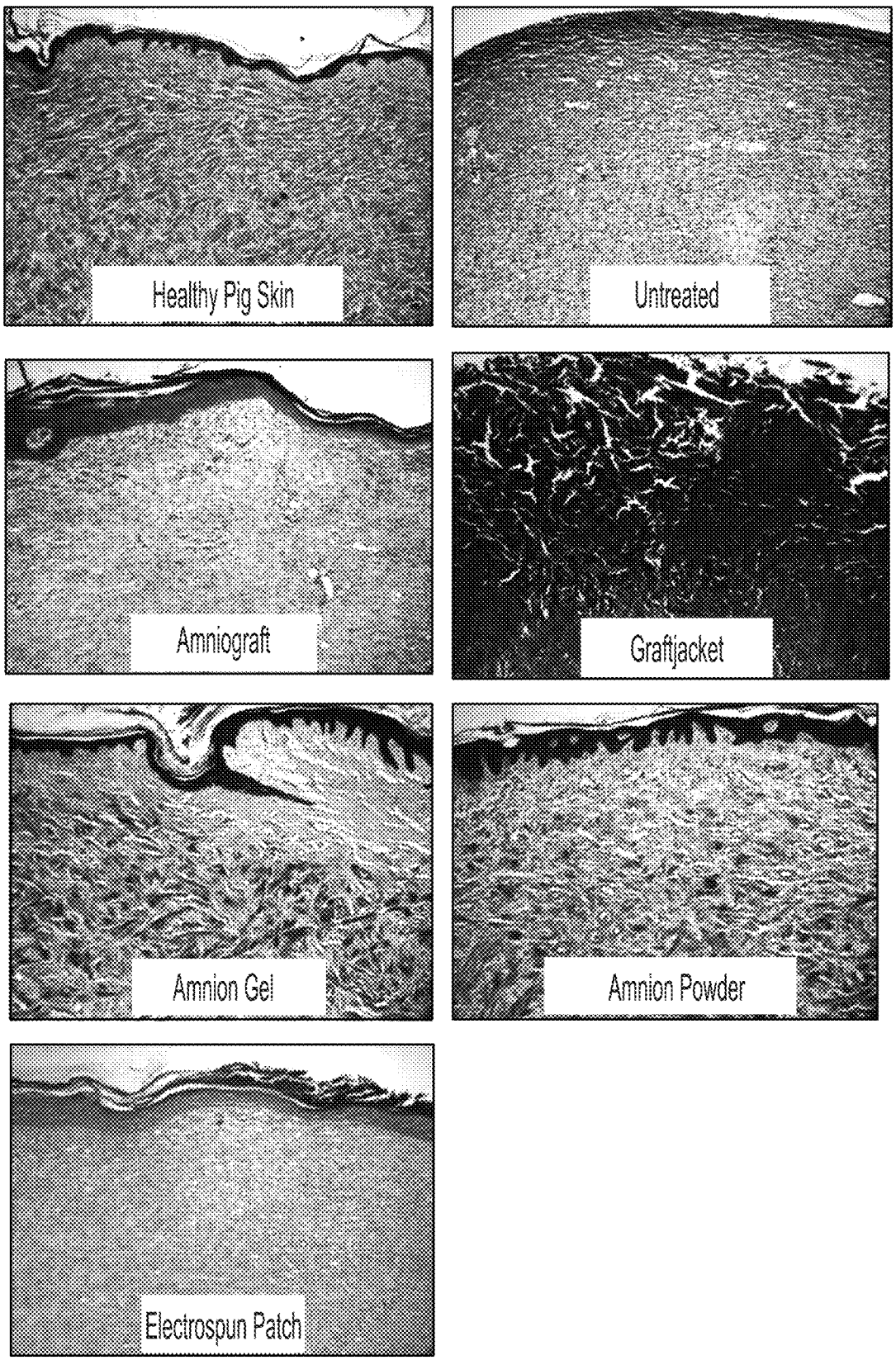
FIG. 17 is a set of images illustrating Pentachrome staining of tissues.

Pentachrome Staining:

Pentachrome straining was performed to give an overview of the extracellular matrix (ECM) composition of the wounds. Pentachrome is a stain that is able to identify multiple ECM components simultaneously. Pentachrome staining shows in collagen in yellow, mature fibers in red, mucins and glycosaminoglycans (GAGs) in blue/green, and nuclei and elastic fibers in black. FIG. 17 shows the representative images of the 6 treatment groups and healthy skin. In this study, the overlapping/close proximity of collagen and mucins/GAGs resulted in a green coloration of the tissues. Healthy skin had a dermis that consisted of thick mature collagen fibers (red) and positive yellow and green staining for collagen and mucins/GAGs. Very little black elastin or purple inflammatory or fibrotic cell infiltration was observed. Untreated and GRAFTJACKET®-treated tissues showed primarily densely-packed nuclei with little observable red, green, or yellow staining. This suggests that these areas may consist of granular tissue composed infiltrating inflammatory cells and fibroblasts. AMNIOGRAFT® and Electrospun Patch-treated wound tissues show some collagen and mucins/GAGs, but little red stained fibroid/muscle, indicating a lack of normal mature dermis structure. Amnion Hydrogel and Amnion Powder-treated wounds appeared very similar to healthy skin with an intermediate amount of thick mature collagen fibers (red) on a yellow/green background of collagen, mucins and GAGs. This suggests that these tissues are of similar composition to healthy skin, however containing slightly less mature collagen fibers, and more mucins/GAGs.

Figure 18:
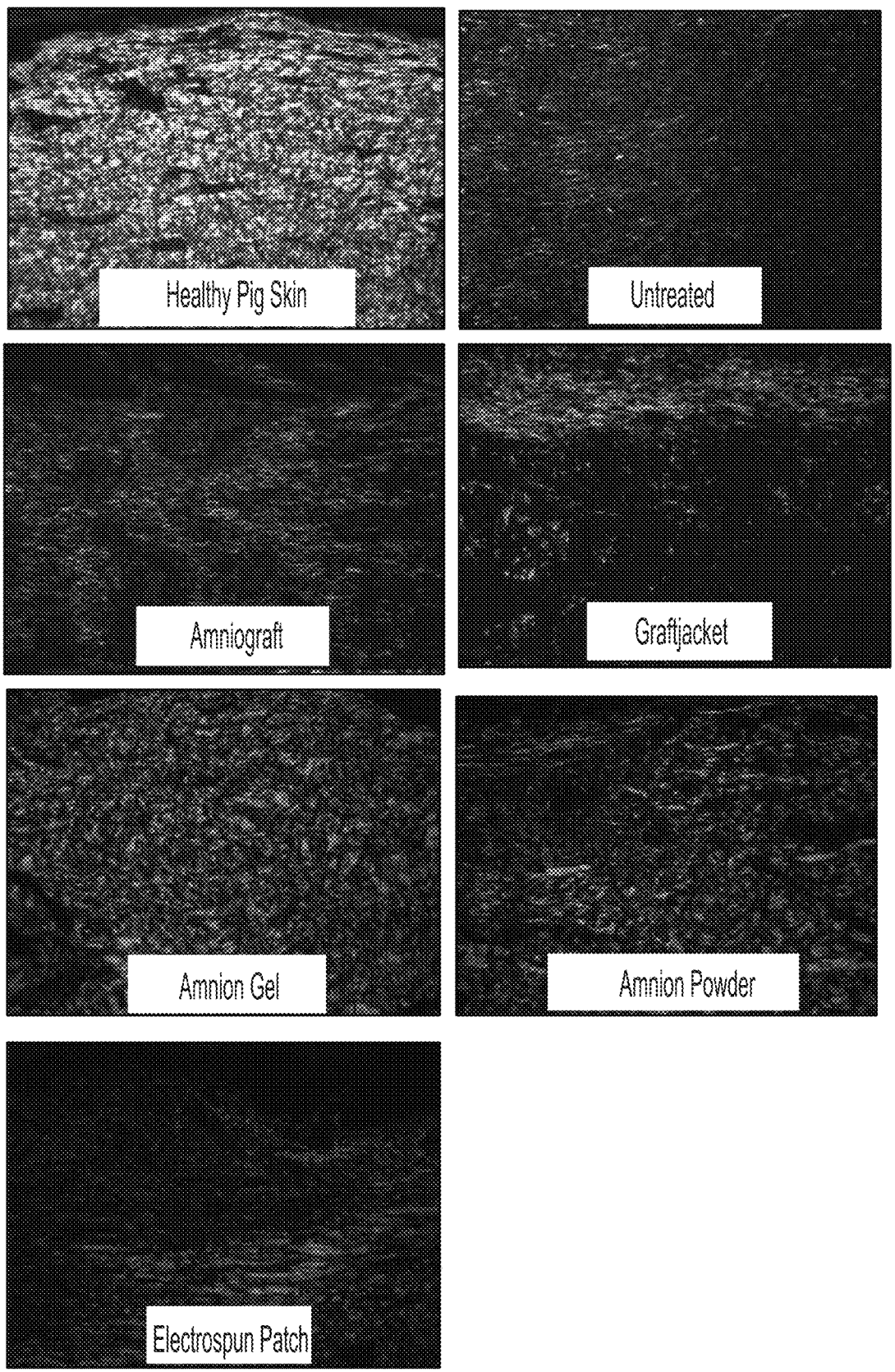
FIG. 18 is a set of images illustrating Sirius Red staining of tissues viewed with polarizing light.

Sirius Red Staining for Immature and Mature Collagen:

Sirius Red staining differentiates between immature and mature collagen when viewed under polarized light Immature unorganized collagen stains green and mature organized collagen stains yellow/orange. FIG. 18 illustrates the representative images of the 6 treatment groups and healthy skin. Healthy skin exhibited strong staining of both green and orange, indicating an organized network of larger mature collagen fibers with smaller collagen fibers intermixed. GRAFTJACKET®-treated wounds showed very little green staining, except within the scab region. Conversely, there was positive staining for orange-stained mature collagen. However, it was localized to small areas sporadically arranged throughout the tissue. The Electrospun Patch-treated wounds showed less, but still observable, orange-stained collagen. However, there was a higher green-orange ratio in the Electrospun Patch group, indicating slower ECM regeneration. Untreated and AMNIOGRAFT®-treated groups displayed little to no orange stain, and mostly appeared green, indicating even slower ECM regeneration. The Amnion Hydrogel treated-wounds appeared similar to the healthy skin, showing a similar distribution of orange and green. The Amnion Powder treated-wounds appeared to have slightly less orange-stained organized mature collagen, but did exhibit notable staining intensity and distribution.

In sum, Amnion Hydrogel-treated wounds and Amnion Powder-treated wounds showed similar organized staining for mature collagen (red) and immature collagen (green) compared to healthy skin. Electrospun Patch also showed some staining for immature collagen but very little organized mature collagen. Untreated and GRAFTJACKET® did not stain positive for organized collagen structures.

Figure 19:
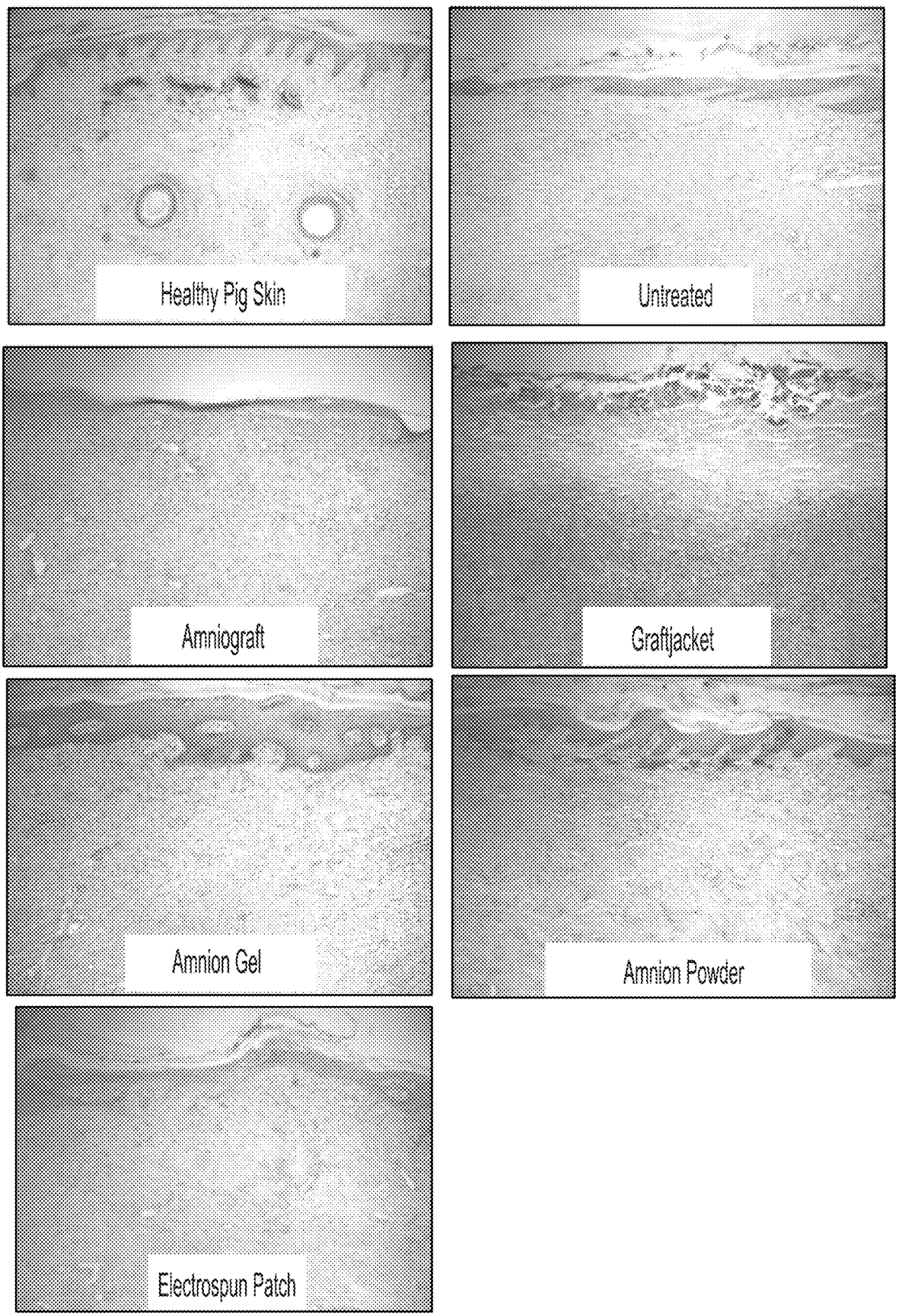
FIG. 19 is a set of images illustrating Alcian Blue staining of tissues to visualize Mucins/GAGs.

Aldan Blue and Iron Colloid Staining for Mucins and GAGs:

Alcian Blue stains mucins and GAGs in blue and nuclei in pink/red. FIG. 19 shows the representative images of the 6 treatment groups and healthy skin. The Amnion Hydrogel and Amnion Powder-treated wounds showed similar localization and intensity of Alcian Blue staining compared to the healthy skin, while GRAFTJACKET® showed intense staining underneath the scab area. Unfortunately, non-specific background staining made interpretation of this stain difficult.

Figure 20:
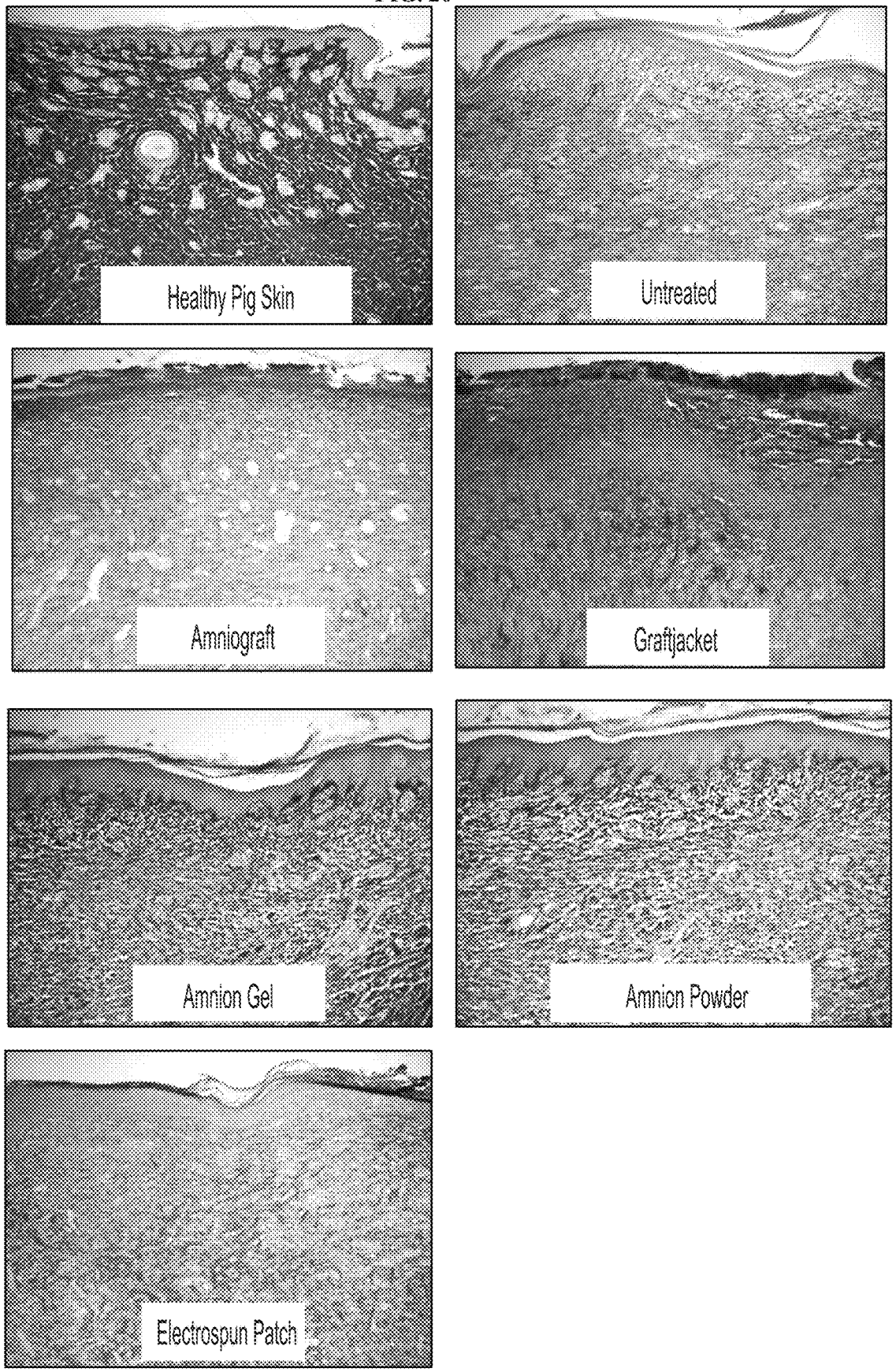
FIG. 20 is a set of images illustrating iron colloid staining of tissues to visualize Mucins/GAGs. This stain is more specific than Alcian blue staining and supported initial observations.

As an alternative method to visualize mucins and GAGs, iron colloid staining was used. iron colloid stains carboxylated and sulfated mucins and GAGs in blue and cytoplasm in pink/red. Additionally, dark red staining of the dermis showing organization of the dermis tissue is heavily apparent in the healthy skin. FIG. 20 shows the representative images of the 6 treatment groups and healthy skin. GRAFTJACKET®-treated wounds showed blue staining in the scab and in a random fashion below the scab. Untreated, AMNIOGRAFT®, and Electrospun Patch-treated tissues showed absent or minimal diffuse blue staining. The Amnion Hydrogel and Amnion Powder-treated wounds showed similar localization and intensity of blue staining compared to the healthy skin—specifically, blue staining directly under the epidermis. Similar dark red staining, but to a lesser degree than in healthy skin, was also observed in the Amnion Hydrogel and Amnion Powder groups. Less of this red staining was observed in the Electrospun Patch-treated group, and little to none of this red staining was observed in the Untreated, AMNIOGRAFT®, and GRAFTJACKET®-treated groups.

Figure 21:
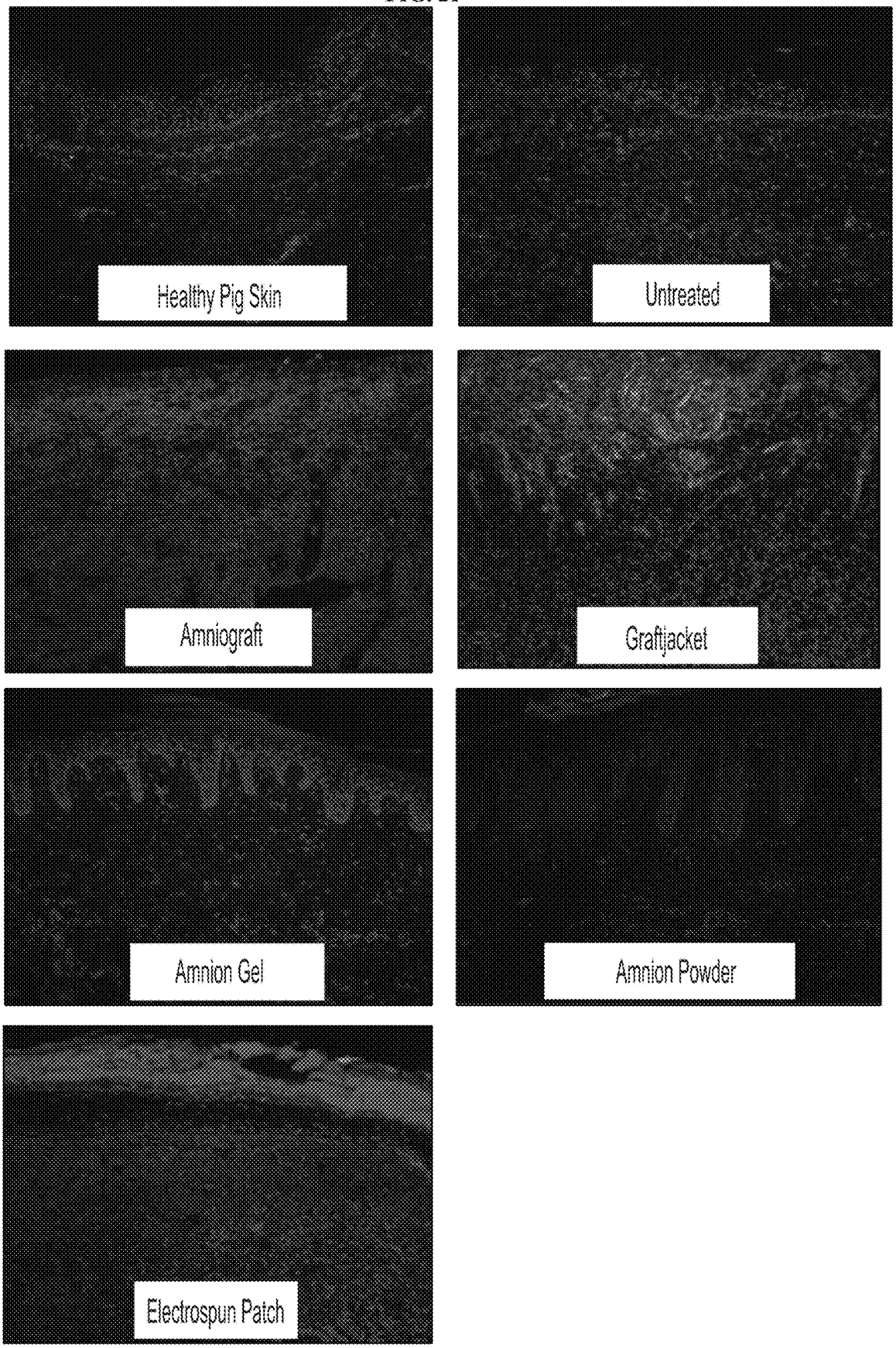
FIG. 21 is a set of images illustrating immuno-staining for Type I collagen (red) and Type III Collagen (green) with DAPI nuclear counterstain (blue).

Collagen Immunohistochemical Staining:

Immunohistochemical staining of collagen type I (red) and type III (green) was performed with fluorescent antibodies with a DAPI cell nuclei counterstain (blue) (FIG. 21). The resulting stained tissue sections from the 6 treatment groups and a healthy skin control showed a varying relative level of fluorescent staining that when combined with histological stains gives insight into the quality of the regenerating tissue and extracellular matrix. At the camera exposure times used to capture the fluorescent images (kept constant across samples), relatively weak collagen type I and type III staining in healthy skin was observed, although both were present. The GRAFTJACKET®-treated group displayed notably different tissue morphology than all the other groups. Due to the heavy scab formation observed in these wounds, the scab as a region densely packed with nuclei and unorganized streaks of strong collagen type III was observed. Beneath the scab, little to no collagen type III, and a low amount of collagen type I was observed, suggesting that the production of new extracellular matrix in this group was significantly delayed compared to other groups. In the Untreated, AMNIOGRAFT®, and Electrospun Patch-treated wounds, intense collagen type I staining was observed, accompanied by little collagen type III staining, suggesting unbalanced collagen type I production, and potentially the generation of fibrotic tissue. Conversely, in the Amnion Hydrogel and Amnion Powder-treated wounds, less collagen type I staining than the previous 3 fibrotic groups was observed, although more than in healthy skin, and a similar level of collagen type III staining as in healthy skin was observed. This suggests that the Amnion Hydrogel and Amnion Powder treatments achieve regeneration of skin that is more similar to healthy skin than the other treatments.

In sum, Amnion Hydrogel and Amnion Powder treated wounds show similar intensity collagen Type III as observed in healthy skin, with slightly greater Type I staining. Untreated, AMNIOGRAFT®, and Electrospun Patch-treated wounds showed intense Type I staining with little Type III. GRAFTJACKET® showed mostly Type III in the scab area.

Figure 22:
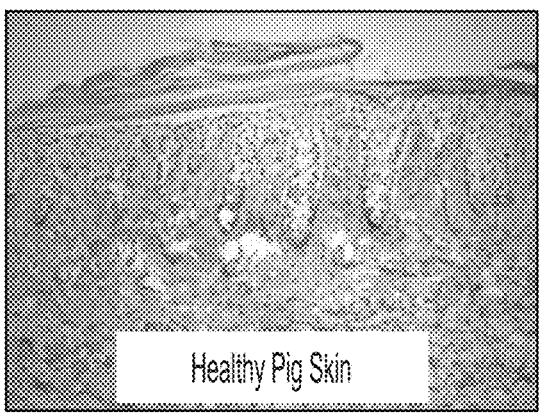
FIG. 22 is a set of images illustrating immuno-staining for Neutrophils (brown) with hematoxylin nuclear counterstain (blue).
Figure 22:
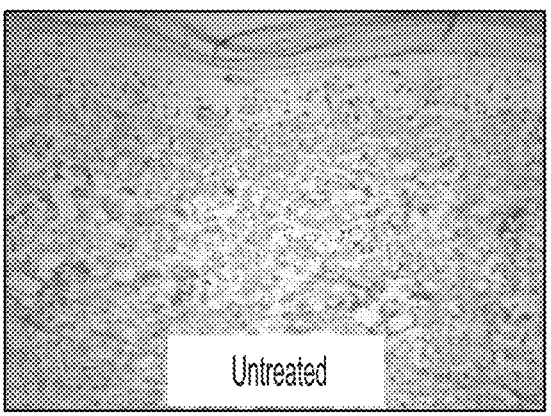
Figure 22:
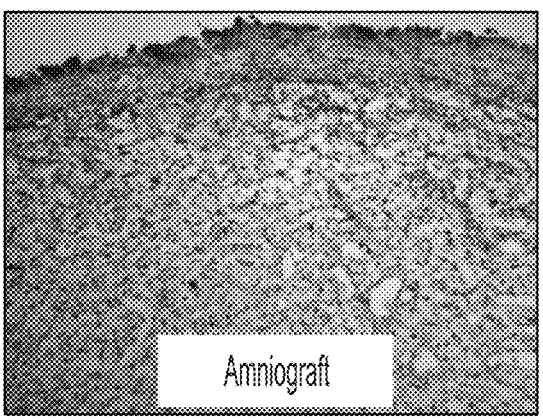
Figure 22:
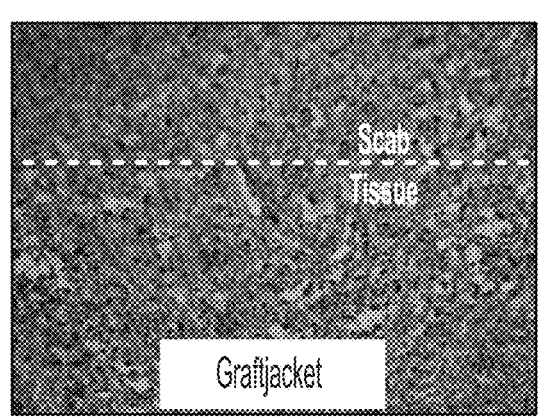
Figure 22:
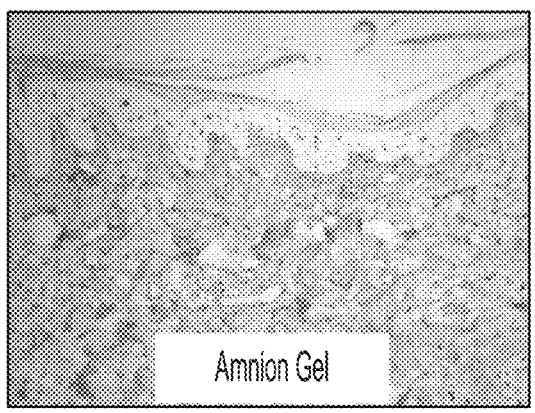
Figure 22:
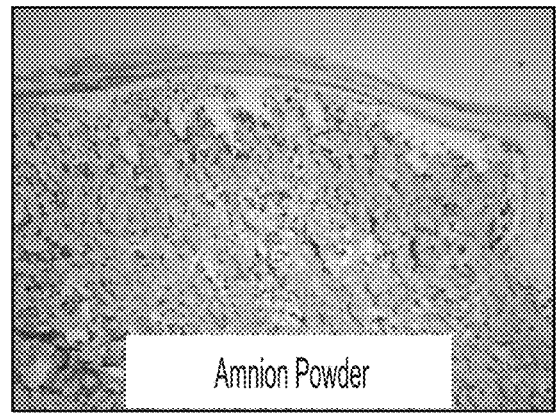
Figure 22:
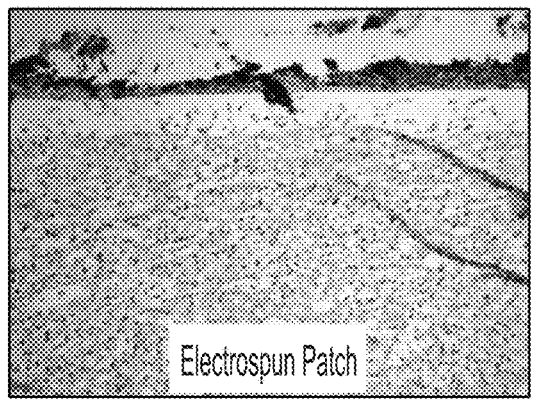

Neutrophil Immunohistochemical Staining:

Immunohistochemical visualization of neutrophils was performed with antibodies and HRP-streptavidin staining. The resulting stained tissue sections from the 6 treatment groups and a healthy skin control (FIG. 22) showed a varying relative level of brown staining that gives insight to the level of immune response occurring at the time of tissue harvest. GRAFTJACKET®-treated wounds showed a high density of brown stained neutrophils underneath the scab-tissue interface. AMNIOGRAFT® and Electrospun Patch groups showed localized areas of intense brown staining, primarily at the surface of the wound and/or interface with the applied treatment patch. In addition, neutrophils were observed throughout the dermis. Amnion Hydrogel, Amnion Powder, and Untreated groups showed similar low level neutrophil presence as was also observed in healthy skin. There was a low level of non-specific background staining, but it was consistent across these groups. These results suggest: 1) A lack of treatment (Untreated group) may allow the neutrophil immune response to happen at an earlier time, rendering it unobservable at 8 weeks; and 2) Amnion Hydrogel and Amnion Powder do not illicit a response, or because they are more easily remodeled, the immune response in truncated, while the AMNIOGRAFT®, GRAFTJACKET®, and Electrospun Patch illicit a prolonged response due to their composition or because they are less easily remodeled into normal ECM.

In sum, Amnion Hydrogel-treated wounds, Amnion Powder-treated wounds and Untreated wounds show similar low level neutrophil presence as observed in healthy skin. AMNIOGRAFT®, and Electrospun Patch showed localized areas of intense staining, markedly at the surface of the wound. GRAFTJACKET® showed a high density of intense stained neutrophils in the underlying scab area.

Figure 23:
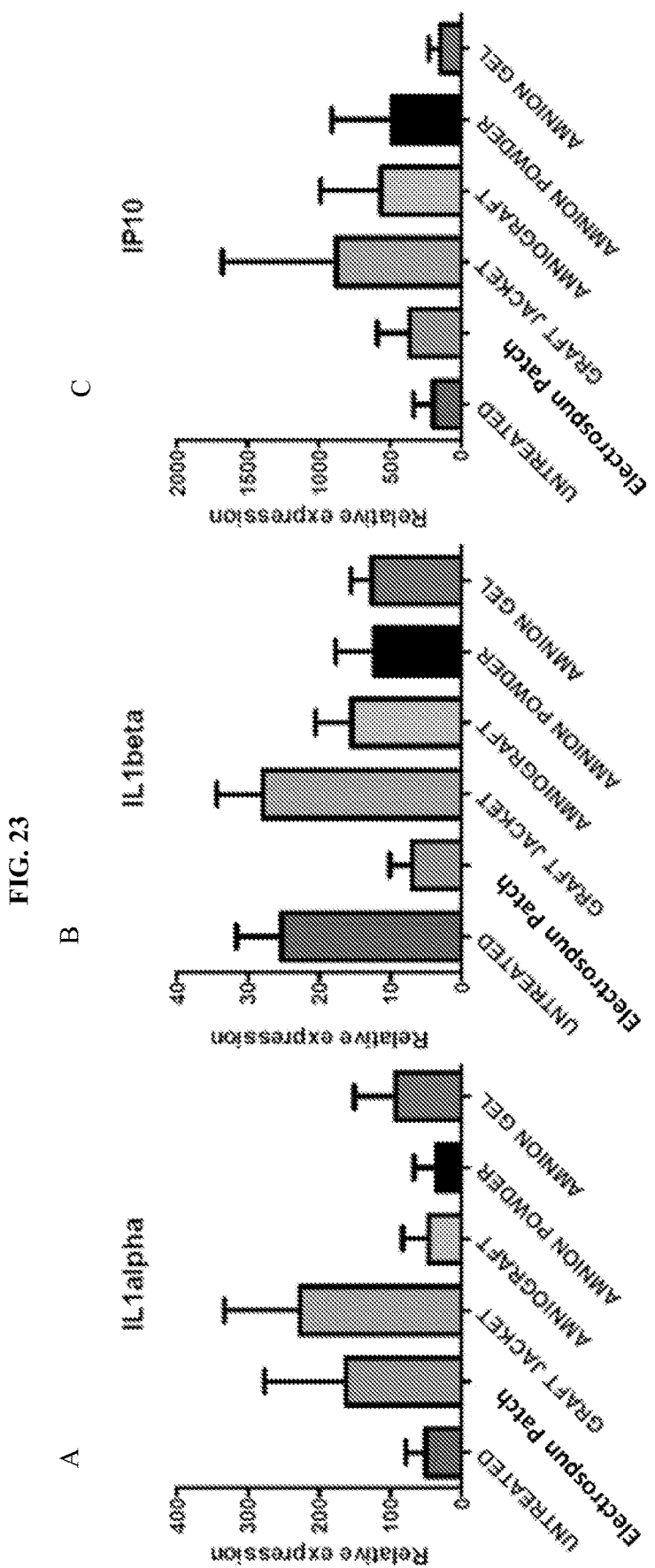
FIG. 23 is a set of three graphs where Panel A illustrates inflammatory markers IL1alpha of non-healing wounds under different treatments; Panel B illustrates inflammatory markers IL1beta of non-healing wounds under different treatments; and Panel C illustrates inflammatory markers IP10 of non-healing wounds under different treatments.
Figure 24:
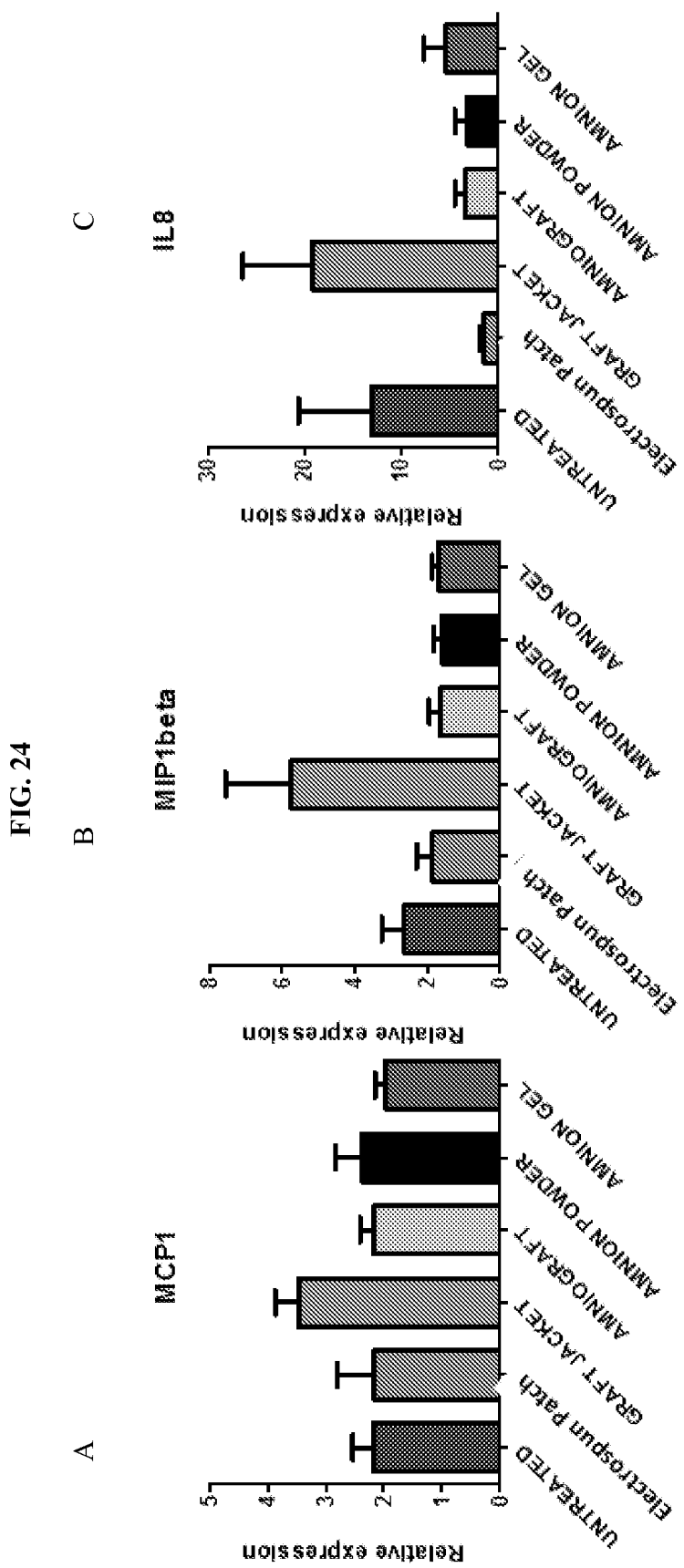
FIG. 24 is a set of three graphs where Panel A illustrates monocyte-related inflammatory markers MCP-1 under different treatments; Panel B illustrates monocyte-related inflammatory markers MIP1beta under different treatments; and Panel C illustrates monocyte-related inflammatory markers IL8 under different treatments.
Figure 25:
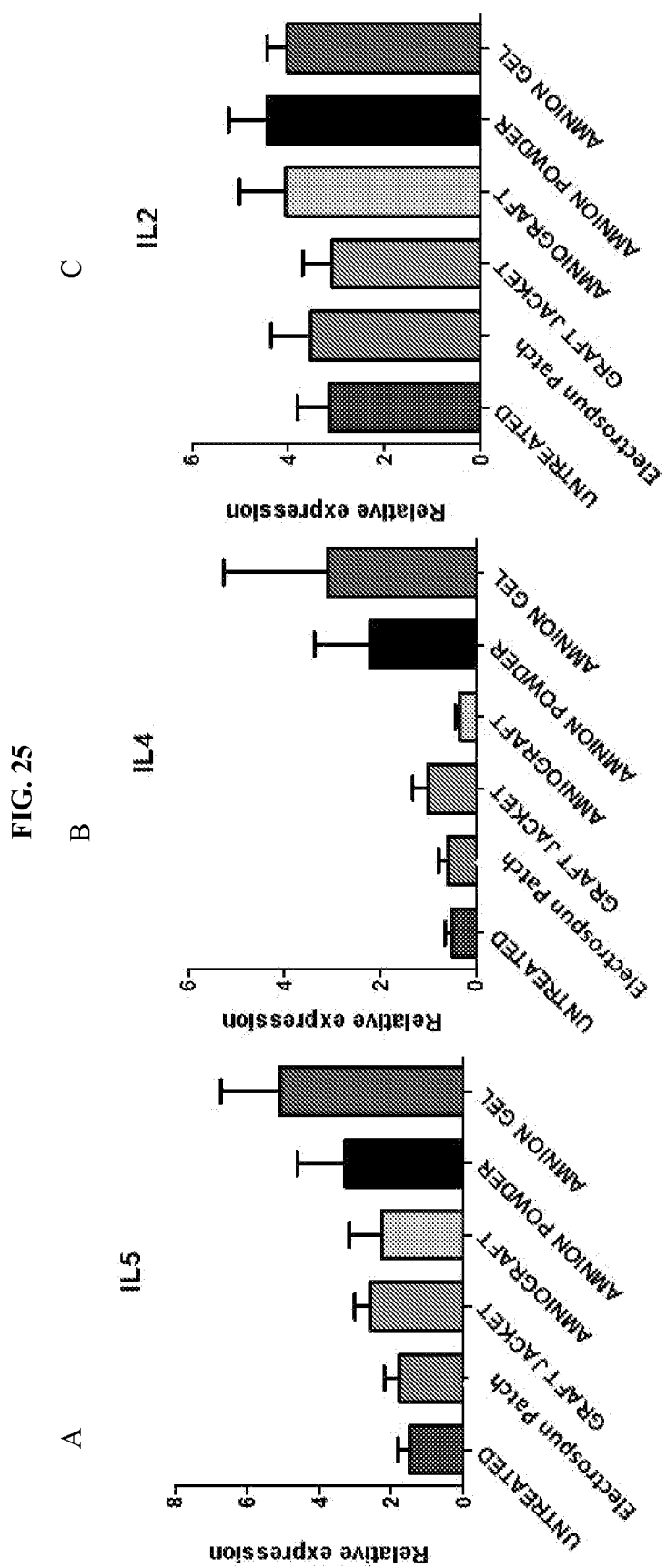
FIG. 25 is a set of three graphs where Panel A illustrates anti-inflammatory markers of healed wounds IL5 under different treatments; Panel B illustrates anti-inflammatory markers of healed wounds IL4 under different treatments; and Panel C illustrates anti-inflammatory markers of healed wounds IL2 under different treatments.

Wound Biomarker Analysis:

Wound biomarkers were selected due to their success in predicting wound healing or requirement for debridement in human patients. Biomarkers for inflammatory non-healing wounds (IL1 alpha, IL1 beta and IP-10), monocyte-related inflammatory markers (MCP-1, MIP-1 beta and IL-8) and anti-inflammatory markers of healed wounds (IL2, IL-4 and IL-5) were analyzed by quantitative PCR and expressed relative to normal skin. GRAFTJACKET®-treated wounds showed consistent high expression of biomarkers of inflammatory non-healing wounds, while Electrospun Patch-treated and Untreated wounds showed expression of inflammatory biomarkers IL1alpha and IL1beta, respectively, suggesting the presence of inflammation and potentially delayed healing outcomes (FIG. 23). AMNIOGRAFT®, Amnion Hydrogel and Amnion Powder-treated wounds all showed expression of biomarkers that were greater than healthy skin but significantly less than other treatment groups. GRAFTJACKET®-treated wounds again showed consistent high expression of biomarkers of monocyte-related inflammatory markers, consistent with the observation of infiltrating inflammatory cells in these tissues (FIG. 24). Untreated wounds had increased expression of MIP1beta and IL8, although this was only a minor trend. Electrospun Patch, AMNIOGRAFT®, Amnion Powder and Amnion Hydrogel-treated wounds had low expression of monocyte-related inflammatory biomarkers. While expression of anti-inflammatory markers of healing wounds was generally low and variable, Amnion Hydrogel and Amnion Powder-treated wounds trended higher than other treatment groups for IL4 and IL5 (FIG. 25). There was less variation between groups for IL2, although expression of this biomarker in AMNIOGRAFT®, Amnion Hydrogel and Amnion Powder-treated groups were slightly increased compared to other treatment groups.

In sum, while variation was observed between animals, there were clear trends observed for these markers. GRAFTJACKET®-treated wounds had increased expression of all markers of non-healing wounds consistent with image analysis. Electrospun Patch-treated wounds had increased expression of IL1 alpha, but not IL1 beta or IP10, while Untreated wounds had increased IL1beta but not IL1alpha or IP10. Overall, AMNIOGRAFT®-treated wounds, Amnion Powder-treated wounds and Amnion Hydrogel-treated wounds had low expression of all markers of non-healing wounds.

Summary

Ease of Treatment Administration:

Observations from the surgeries revealed that application of the patch-type treatments was influenced by the stiffness and flexibility of the product, with the stiffer and thicker GRAFTJACKET® not conforming well to the wound area, even with only minor differences in size and shape. The very thin and flexible AMNIOGRAFT® was difficult to handle and place on the wound even with two surgeons. While a thicker, stiffer product was easier to handle and apply, this property seemed detrimental to wound healing, inhibiting wound closure and epithelialization. Amnion Powder was the easiest product to administer, with a pre-measured weight of powder simply sprinkled over the wound area followed by wetting with 1 mL sterile saline. The application of the Amnion Powder by first suspending the powder in the volume of saline before application to the wound was also tested and found that this further simplified the procedure without detriment to the treatment outcome. This methodology also provides the option of increasing the dose per area wound if desirable. The Amnion Hydrogel was very simple to administer with gelation of the product taking approximately 10-15 seconds within the wound area. While this product required the use of a UV light, development of the product has now eliminated this requirement. With the elimination of the UV light, the Amnion Hydrogel would have the easiest application.

Wound Healing Quality:

Analysis of wound closure, contraction and epithelialization demonstrated that Amnion Hydrogel and Amnion Powder were superior in wound closure and epithelialization, and were among the best performers in preventing contraction. It is important that a global analyses of wound healing is performed to adequately include the mechanisms of wound healing. Amnion Hydrogel and Amnion Powder accelerated the rate and extent of total wound closure through the significant acceleration of wound re-epithelialization. This suggests that wounds regenerated using these products will not only heal faster, but will heal with a mature and healthy epidermal coverage, with less scarring and contraction. While these studies were performed in a healthy skin model with significant endogenous wound healing capability, it is likely that these effects would be magnified in wounds that have delayed or inhibited epithelial growth potential. Interestingly, AMNIOGRAFT® was the next best performing product following the other two amnion products. This suggests the regeneration potential of these treatments is related to the original amnion starting material, and that the processing steps taken to produce the hydrogel and powder did not degrade this property, rather promoting the availability/release of therapeutic factors. This may be related to the release profile of the hydrogel and powder in the wound, which may be more beneficial to wound healing compared to the natural degradation profile of the amnion membrane. Over all outcome measurements of the image analysis, the Electrospun Patch performed almost identical to Untreated wounds, suggesting that this product neither had a beneficial or detrimental effect on wound closure, contraction or epithelialization. As discussed above, the thick and stiff GRAFTJACKET® patch performed poorly in all outcome measurements, and appeared to inhibit wound closure, contraction and epithelialization. This is likely to be due to the mismatch between the rates of degradation of the product and the rate of natural wound closure. This highlights the importance of a wound healing product to seamlessly support and integrate into the regenerating wound over a clinically relevant time-line. Products that can be modified to match the wound environment, such as a gel, would greatly accelerate the closure of varying and difficult to treat wounds.

Skin Quality:

Observations of the dermis showed that the Amnion Hydrogel and Amnion Powder-treated wounds had a dermis similar to healthy skin, consisting of large organized collagen fibers. This suggested that the dermis had matured in these groups having functional and mechanical properties similar to healthy skin. Observation of increased epidermal coverage during wound healing was confirmed by histological analysis of the tissues. While analysis of tissue sections at early time-points was not done, the presence of a thick and mature epidermis with dermal protrusions support the findings of accelerated epithelialization in the Amnion Hydrogel and Amnion Powder-treated groups. While other treatments resulted in an epidermal covering, this appeared thinner and lacked these dermal protrusions. This suggests that the epidermis in these tissues was less mature, perhaps developing later during the healing period. The quality of the wound ECM is of key importance to the long-term success of the healing wound. ECM composition has a major influence over the properties of healing wounds. A normal healthy ECM facilitates normal cellular and mechanical properties, and an abnormal ECM composition causes scarring, contraction and loss of function. For this reason extensive characterization of the tissue histology and composition of the ECM for these products was performed. Histological staining confirmed initial observations, showing that Amnion Hydrogel and Amnion Powder-treated wounds had a dermal ECM composition consisting of thick mature collagen fibers intertwined with less immature collagen and mucins/GAGs with localizations and staining intensities consistent with mature skin. In the IHC collagen stains, less type I collagen in the Amnion Hydrogel and Amnion Powder-treated groups compared to the other groups was observed. This may indicate less scar-like fibrotic collagen, which is typically unorganized. It appears that slowing down unorganized collagen type I deposition in the regenerating tissue may result in slower forming, but more organized mature collagen fibers, of which the tissue would be less fibrotic in nature. Additionally, slightly increased iron colloid staining of mucins/GAGs in the Amnion Hydrogel and Amnion Powder-treated groups compared to other groups was observed. This may further suggest that by preventing unorganized fibrotic collagen formation, not only are mature collagen fibers able to form, but also other ECM components such as hyaluronic acid, heparan sulfate, chondroitin sulfate, and other GAGs/proteoglycans that are important for healthy matrix and tissue. On the other hand, Untreated, AMNIOGRAFT®, and Electrospun Patch-treated wounds showed a dermal ECM composition that consisted of unorganized and immature collagen, and diffuse mucins/GAGs. This was supported by observation of intense collagen type I staining, accompanied by little collagen type III staining, suggesting that these tissue may be progressing to the generation of fibrotic tissue, leading to contraction and scarring.

Immune Response:

As previous studies were performed in immune compromised animals, it was important to evaluate whether human tissue-derived materials induce an immune response in these immune competent animals. Interestingly increased inflammatory cell infiltration in the AMNIOGRAFT® and Electrospun Patch-treated wounds was observed. This may be due to the presence of intact human cells in the AMNIOGRAFT®, however as the composition of the Electrospun Patch is unknown, the cause of the inflammation in these groups is unknown. As expected, Untreated wounds only had a low level of inflammatory cell infiltration similar to healthy skin. GRAFTJACKET®-treated wounds exhibited a major inflammatory response, both within the scab area and in the underlying tissue. Whether or not these responses would have also been observed in the allogeneic application in human patients is unknown. However it does suggest the presence of stimulatory antigens these products. Importantly, increased inflammatory cell infiltration in Amnion Hydrogel or Amnion Powder at time of tissue harvest was not observed, suggesting that these products do not stimulate a detrimental immune reaction in the xenogeneic setting to the same extent as the other treatments. This supports the application of this product in the allogenic setting with minimal risk. Inflammatory biomarkers have shown some success in predicting the success or failure of various wound healing treatment strategies. A panel of 9 biomarkers based on their ability to predict wound healing outcomes in human wounds was selected. Strong trends over all three categories of biomarkers were observed, with the delayed-healing GRAFTJACKET® showing high expression of inflammatory biomarkers of non-healing wounds, and low expression of biomarkers of healing wounds. The opposite result when analyzing Amnion Hydrogel and Amnion Powder-treated wounds was observed, showing low expression of inflammatory biomarkers of non-healing wounds, and increased expression of biomarkers of healing wounds. This supports the use of these biomarkers to predict wound healing in this model. However there were several limitations to use of biomarkers in the model. First, in this healthy animal model of wound healing most other treatments do eventually result in complete wound closure, albeit with varying levels of efficacy. Compared to genuine non-healing wounds, the differences in the expression levels between these treatment options were likely to be smaller, even though the observed trends do match image and histological analysis. Second, tissues were collected at the final time-point of this study, potentially after the time of peak inflammation. This may account for the overall low levels of expression observed for several markers in these experiment.

In conclusion, the Amnion Hydrogel and Amnion Powder were the easiest products to administer to full thickness wounds in the porcine model. Application of these products resulted in the most rapid wound closure rates, driven primarily by new epithelialization, and without immune rejection. These observations were supported by histological and biomarker analysis, which demonstrated that these treatments promote the rapid healing of these full-thickness wounds, resulting in the formation of a mature epidermis and dermis with similar composition to healthy skin.

In Vivo Study Two

In Vivo Study with New Hydrogel Crosslinked with PEGDMal

The purpose of this study was to evaluate whether replacing the Polyethylene (glycol) Diacrylate (PEGDA) crosslinker with a Maleimide functionalized polyethylene glycol (PEGDMal) altered the basic hydrogel properties. This in vivo study demonstrated that there were no significant differences between hydrogels crosslinked with either product.

PEGDMal is a reactive PEG derivative capable of forming stable bonds between the maleimide and thiol groups of the hydrogels. The maleimide-thiol reaction speeds up the crosslinking in comparison to the traditional acrylate-thiol reaction, resulting in almost instantaneous crosslinking upon mixing of the hydrogel components, thus eliminating the requirement for UV light to crosslink the hyaluronic hydrogel.

The new hydrogel formulation can also be combined with amnion powder or solubilized amnion membrane, by combing the PEGDMal crosslinker with amnion powder/solution and saline in one syringe piston, and HA and gelatin in the other. Additionally, the individual components can be stored frozen indefinitely within the dual chamber syringe without cross-linking. Following thawing, working time has been shown to be up to approximately 8 hours, before thiol-thiol disulfide bonds begin forming within the thiolated HA and gelatin solution.

Animals and Wounds:

Three Specific Pathogen Free (SPF) Yorkshire pigs were purchased and allowed to acclimatize for the required 2-week period. At the start of the study the pigs weighed approximately 40-50 kg. This study was reviewed and approved by the Wake Forest University Institutional Animal Care and Use Committee (A13-015-Amnion products for Wound Healing in Pigs). All training, wound creation and bandaging was performed as described above. Briefly, 8 areas of skin wound were created by removing 4×4 cm of full thickness skin in the central back along the thoracic and lumbar area. Incisions were made along the wound edges to the panniculus carnosus layer and the overlying skin was excised.

Figure 30:
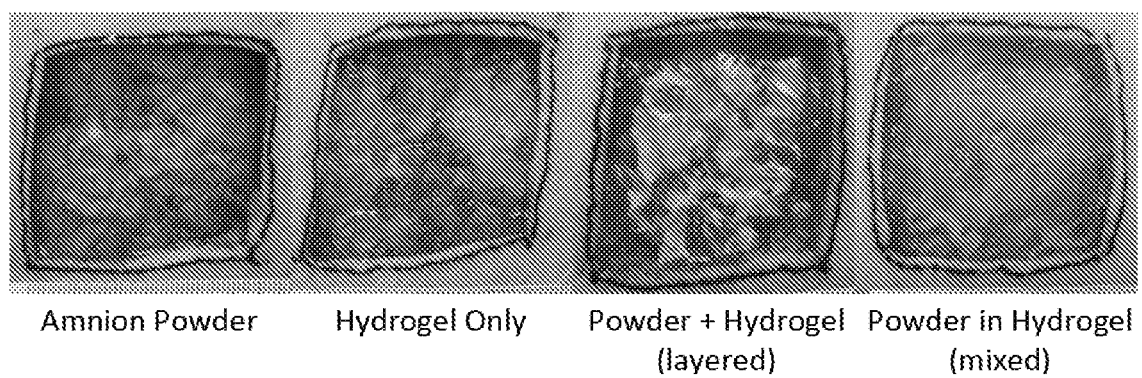
FIG. 30 is a set of images of the four samples in the study. Powder was applied directly to the wound followed by 1 mL sterile saline. Hydrogel was prepared in a two-part syringe system and cross-linked directly into the wound, either alone, layered above amnion powder or pre-mixed with the powder and loaded into each chamber of the syringe.
Figure 31:
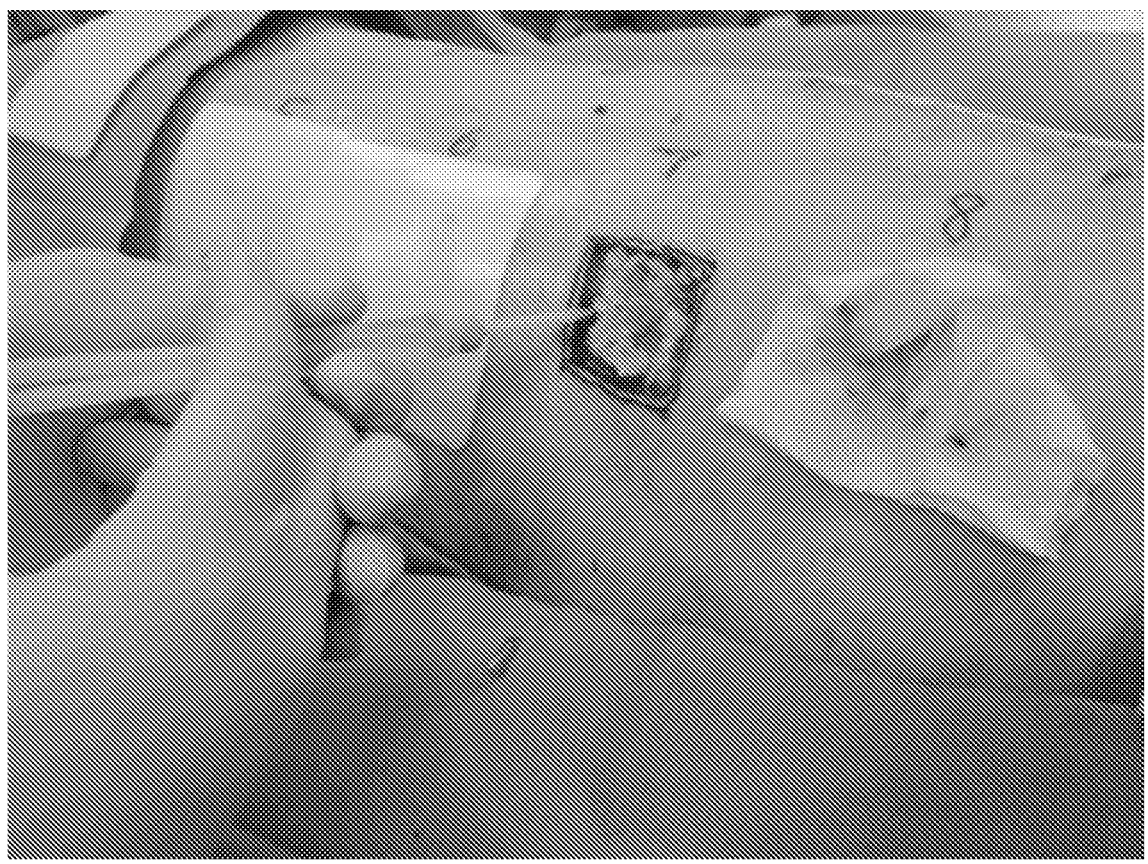
FIG. 31 is an image illustrating how the hydrogel was prepared in a two-part syringe system.

Wound Treatments:

The wound area was treated either with 88 mg Amnion Powder, applied directly to the wound surface, 8 mL of the modified hyaluronan hydrogel carrier only, Amnion Powder layered under the hydrogel or Amnion Powder pre-mixed with the hydrogel. An additional group underwent no treatment. Images of wounds treated with each of the amnion/hydrogel formulations are shown in FIG. 30 and FIG. 31. The five experimental options were distributed over the 8 skin defects to control for differences in wound locations. The experimental round ran for 28 days, during which the wounds were inspected 2 times each week for 1) documentation of wound size, re-epithelialization, and closure, and 2) cleaning, and re-bandaging.

Preparation of Hydrogel

Figure 27:
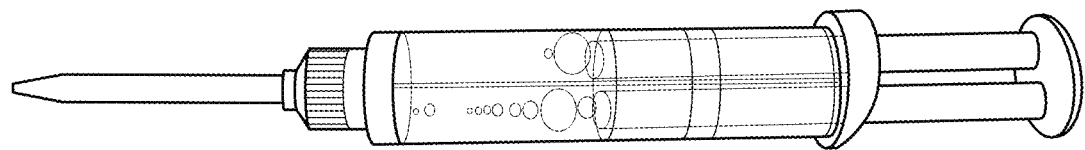
FIG. 27 is an image illustrating that the two-part hyaluronic acid (HA) hydrogel can be loaded into a dual chamber syringe keeping the thiolated components separated from multifunctional cross-linking agents (crosslinker).
Figure 28:
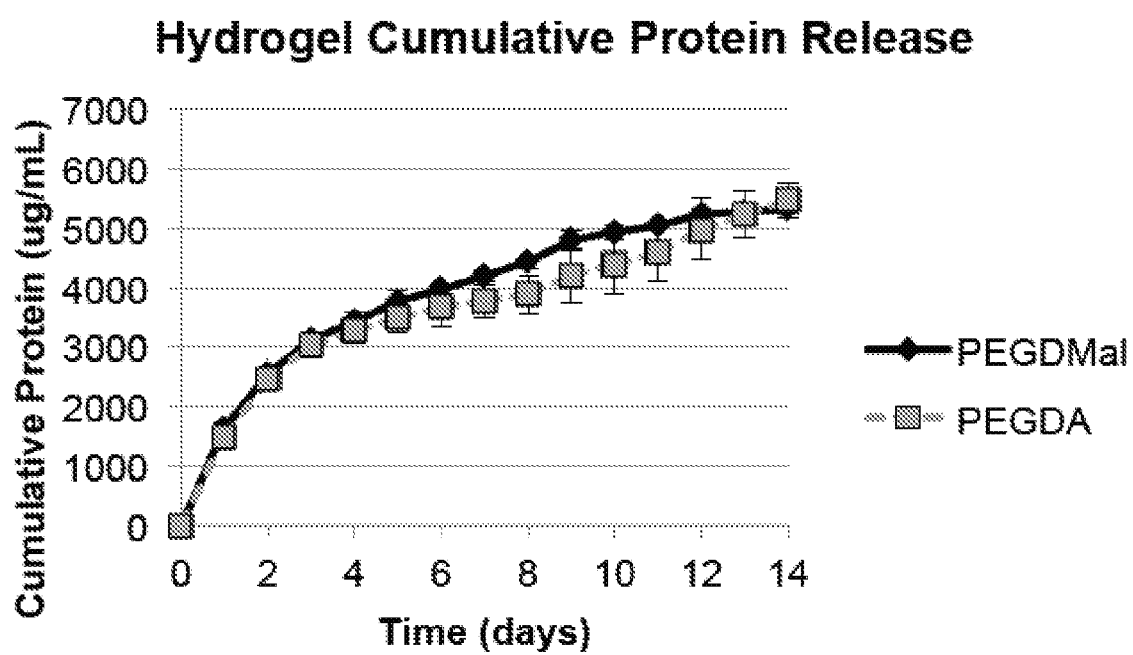
FIG. 28 is a graph illustrating the cumulative protein release from two hydrogels. One comprises poly (ethylene glycol) based crosslinker with maleimide functional groups (PEGDMal); the other comprises poly(ethylene glycol) diacrylate (PEGDA).
Figure 29:
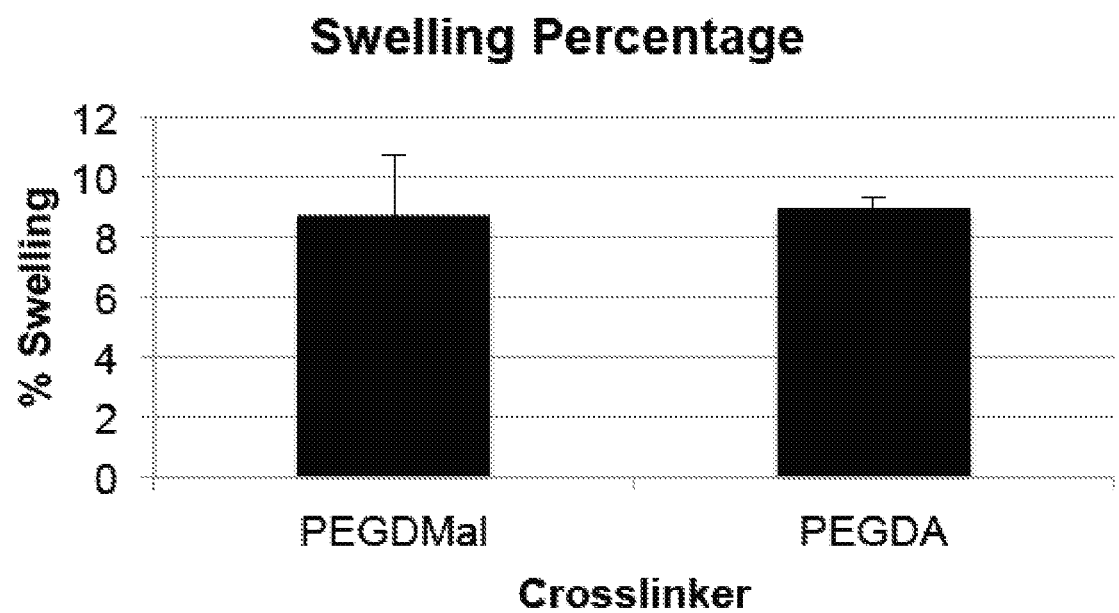
FIG. 29 is a graph illustrating the swelling characteristics of hydrogels made by PEGDMal and PEGDA.

The preparation of hydrogel used in this in vivo study followed the same procedure described in In Vivo Study One herein, except using PEGDMal as the crosslinker. The final concentration of HA:gelatin:crosslinker (PEGDMal) are the same as HA:gelatin:crosslinker (PEGDA) in In Vivo Study One, but the starting concentrations and volumes above are altered to allow for creation of 2 equal volume reagents that can be placed into dual syringes w/mixing syringe tips for deposition (FIG. 27). Cumulative protein release and gel swelling over a period of 14 days was measured (FIG. 28 and FIG. 29). No significant differences between hydrogels crosslinked with either product were observed.

Groups:
1. Untreated control
2. Hydrogel
3. Amnion Powder
4. Amnion Powder+Hydrogel (layered powder under hydrogel)
5. Amnion Powder in Hydrogel (mixed before application)

TABLE 3

| | | | Wound Distribution: | | | | | |
|---|---|---|---|---|---|---|---|---|
| Pig | Wound 1 | Wound 2 | Wound 3 | Wound 4 | Wound 5 | Wound 6 | Wound 7 | Wound 8 |
| #7 | Untreated | Powder | Hydrogel | Powder + Hydrogel | Powder in Hydrogel | Powder | Powder + Hydrogel | Hydrogel |

TABLE 3-continued

Wound Distribution:

| Pig | Wound 1 | Wound 2 | Wound 3 | Wound 4 | Wound 5 | Wound 6 | Wound 7 | Wound 8 |
|---|---|---|---|---|---|---|---|---|
| #8 | Powder | Hydrogel | Powder + Hydrogel | Powder in Hydrogel | Hydrogel | Untreated | Powder in Hydrogel | Untreated |
| #9 | Powder + Hydrogel | Powder in Hydrogel | Powder | Hydrogel | Untreated | Powder in Hydrogel | Powder + Hydrogel | Powder |

Study Analysis:

At 28 days post-treatment, the study was terminated and the wound areas were harvested. Wounds were split into two halves: one for histology and immunohistochemistry and one for mechanical testing. Following mechanical testing, this tissue was divided again and stored for potential use for PCR analysis of wound healing biomarkers and protein assays.

Figure 38:
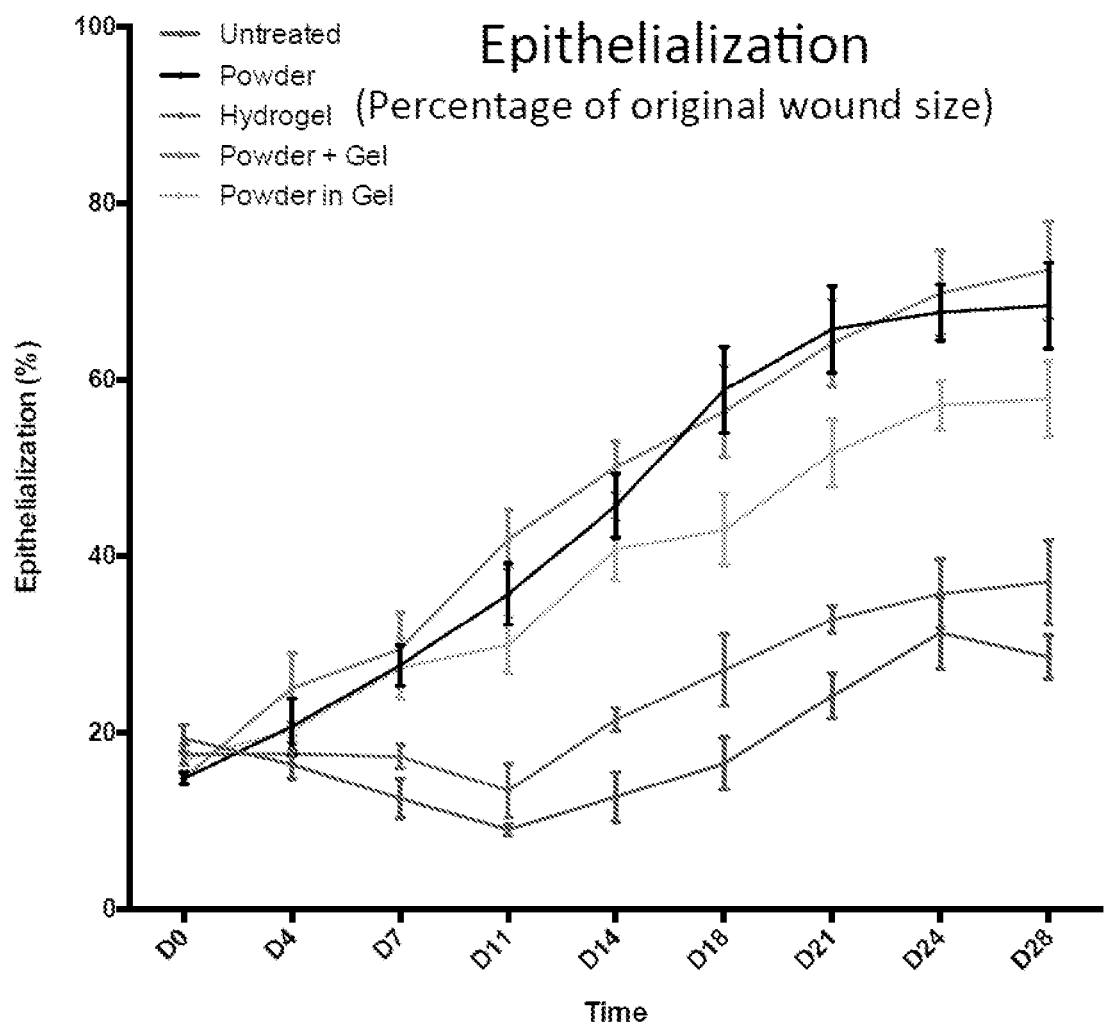
FIG. 38 is a graph illustrating the changes of percentage of original wound size over time under different treatments.

Image Analysis:

Contraction was measured at each of the time-points by measuring the area inside the tattooed square using the software ImageJ and expressed relative to original tattoo size. The wound contraction ratio describes the extent of which the wound has changed shape from the initial square wound. Wounds healing by re-epithelialization normally maintain their initial square shape while contracting slightly and symmetrically. Highly contractile wounds usually contract from the edges of the wound, resulting in a star shaped wound. Wound closure and epithelialization was measured by using ImageJ to determine the area of open wound, mature, and immature epithelium, which can be identified by color and texture of the healing wound. Generally open wounds were dark red and shiny, immature epithelium was light red and opaque/matte (due to a thin epidermis covering), and mature epithelium was white/pink and opaque/matte. These components were measured expressed as individual measurements relative to the original wound size, and combined to demonstrate the contribution of all components to the wound healing over time (FIG. 38).

Figure 44:
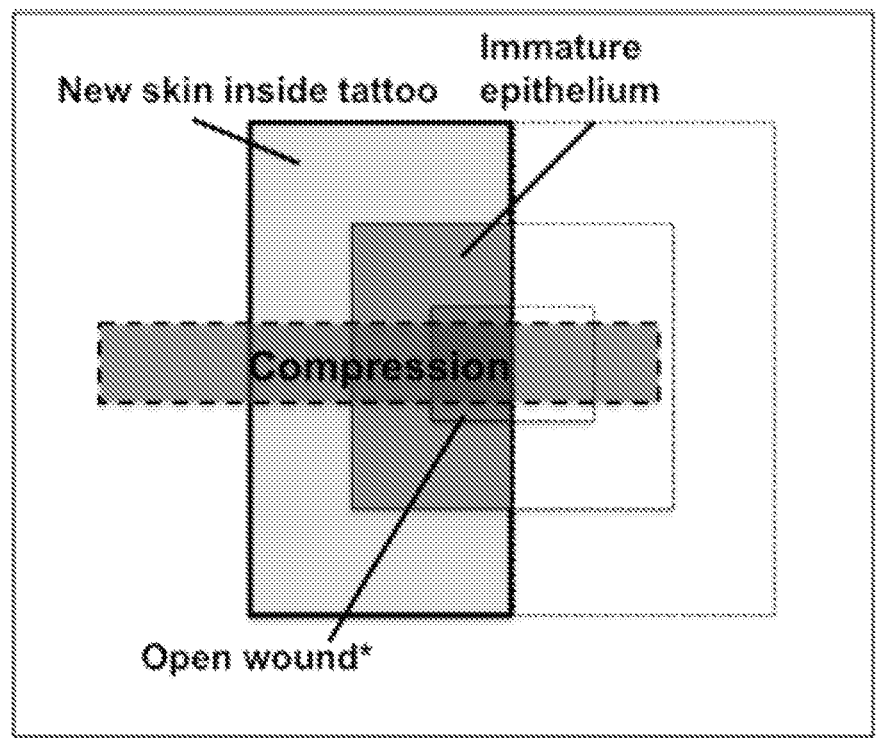
FIG. 44 is a schematic diagram illustrating the compression testing to measure mechanical properties of regenerated skin.

Histology and IHC:
1) H&E staining
2) Pentachrome staining for collagen, mucins/GAGs, elastin and mature fibers
3) Sirius Red staining for mature and immature collagens Mechanical Testing:

To analyze mechanical properties of the regenerated skin wounds, half of each excised wound at time of euthanasia was immediately assessed by compression testing using an Instron mechanical testing machine. Samples consisted of the outer edge of the wound to the center of the wound, and the compressing device was oriented along this path as depicted in FIG. 44. Each sample underwent compression at a rate of 5 mm/minute, during which load, stress, and strain were measured and recorded using the Bluehill Software package accompanying the Instron machine.

Figure 45:
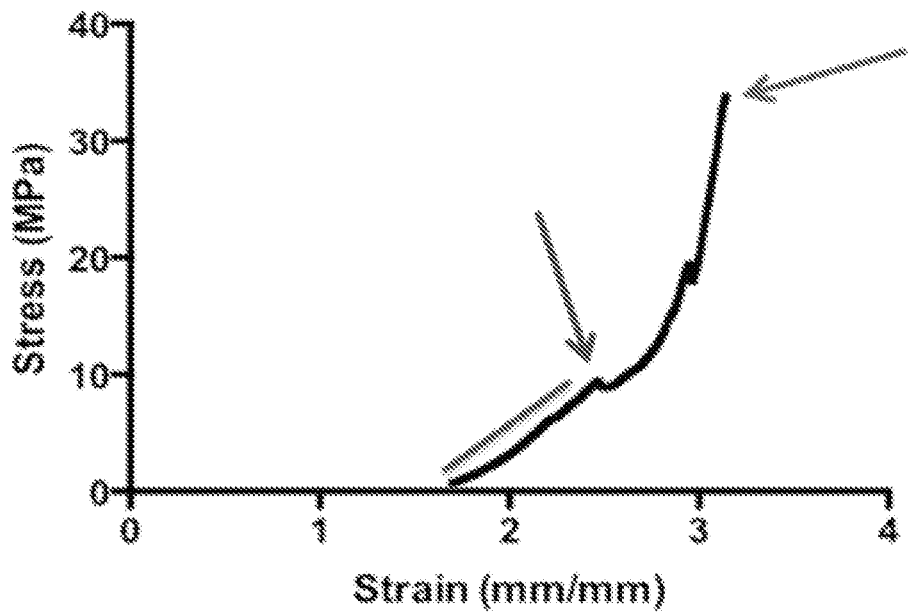
FIG. 45 is a graph illustrating a representative non-linear stress-strain curve for regenerating porcine skin: compressive strength (red arrow), the elastic region of which the slope gives Young's modulus for compression (green line), and the yield point, above which the material becomes damaged and acts plastically (blue arrow).

Stress-strain curves were compiled for each sample by importing the data into GraphPad Prism, where all downstream analysis was performed. In general, soft tissues result in non-linear stress-strain curves, as they are not perfectly elastic. As such a representative stress-strain curve resemble that which is depicted in FIG. 45. Such a curve yields the following data, also depicted in FIG. 45:

Compressive strength, which corresponds to the final strength at where the material fails. This is indicated by the red arrow.

The initial nearly linear portion of the curve, which describes the elastic domain of the material. In this domain, the material stretches, but has the capability to rebound if the applied force is removed. The slope of this linear portion gives the Young's modulus for compression E. This is indicated by the green line.

The termination of the elastic domain, or initial linear portion of the curve, indicated by the blue arrow, is the yield point. Above this point, damage occurs to the material, and it behaves plastically and will not return to its original state.

Results

General Observations

All surgical procedures were performed without complications. Wounds were created with a uniform size and depth. Some sagging of the skin was observed following removal of the square skin section. Amnion Powder was evenly distributed by tapping the tube gently over the wound, followed by the application of 1 mL of sterile saline to wet the powder. Alternatively the powder could have been applied by first mixing with saline. Previous studies have shown no differences between each method of delivery for any measured parameters. The new hydrogel formulation was prepared under sterile conditions in the morning before surgery and transported to the operation room on ice. Each of the hydrogel treatments were very easy to administer, requiring only one hand and resulting in the formation of a gel almost instantaneously within the wound. No dripping, or loss of material occurred. Pre-mixing of the Amnion Powder in the hydrogel components and delivery via dual chamber syringe was easy to perform. Although the powder was not 100% soluble at the delivered concentrations, the powder mixed in hydrogel treatment was easily delivered without loss of product.

Figure 32:
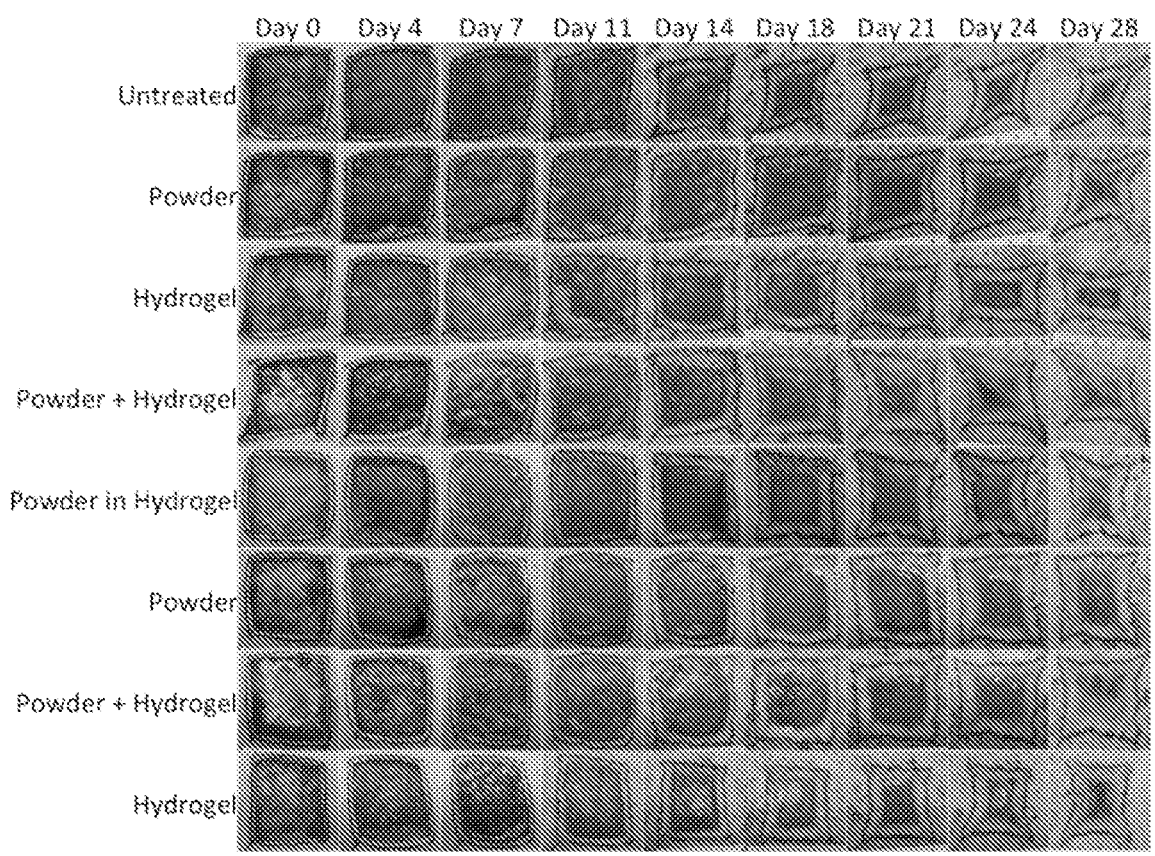
FIG. 32 is a set of images illustrating how the wounds heal under different treatments over time (pig 7).
Figure 33:
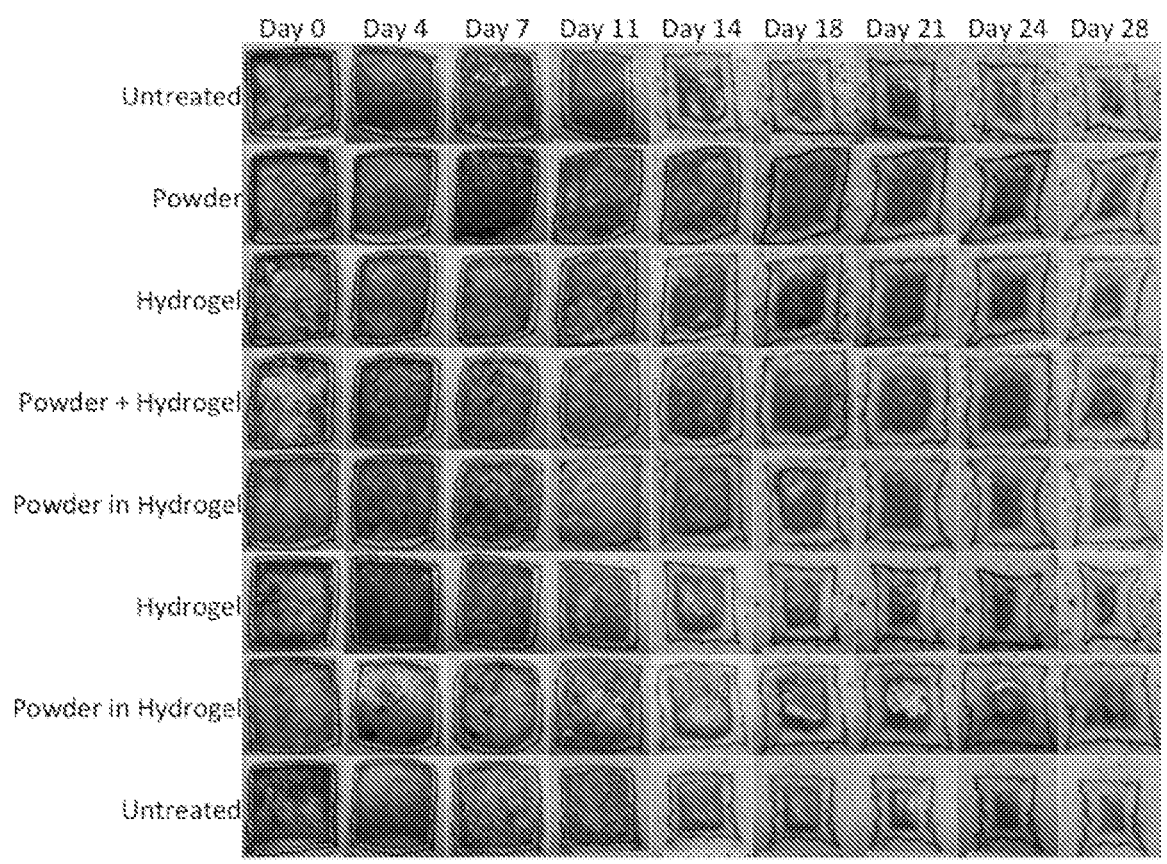
FIG. 33 is a set of images illustrating how the wounds heal under different treatments over time (pig 8).
Figure 34:
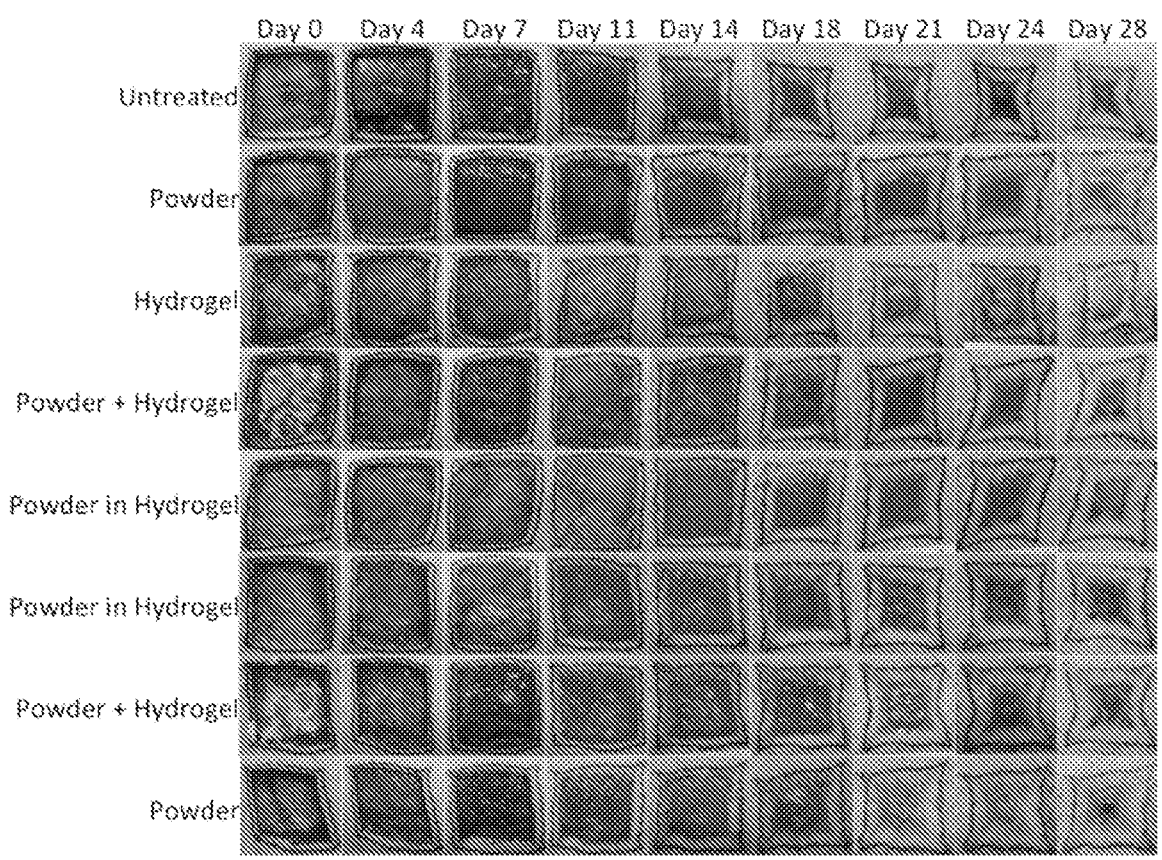
FIG. 34 is a set of images illustrating how the wounds heal under different treatments over time (pig 9).

Image Analysis:

Digital photos were taken for each of the time-points (Days 0, 4, 7, 11, 14, 18, 21, 24 and 28) and compiled for each of the 8 wounds (FIG. 32, FIG. 33, and FIG. 34). Note: Wound-treatment distribution is described in Table 3 above. Treatment options are kept in the same order for each animal for ease of comparison. The lower three treatments on each pig are the repeated three treatment options for that pig.

Figure 35:
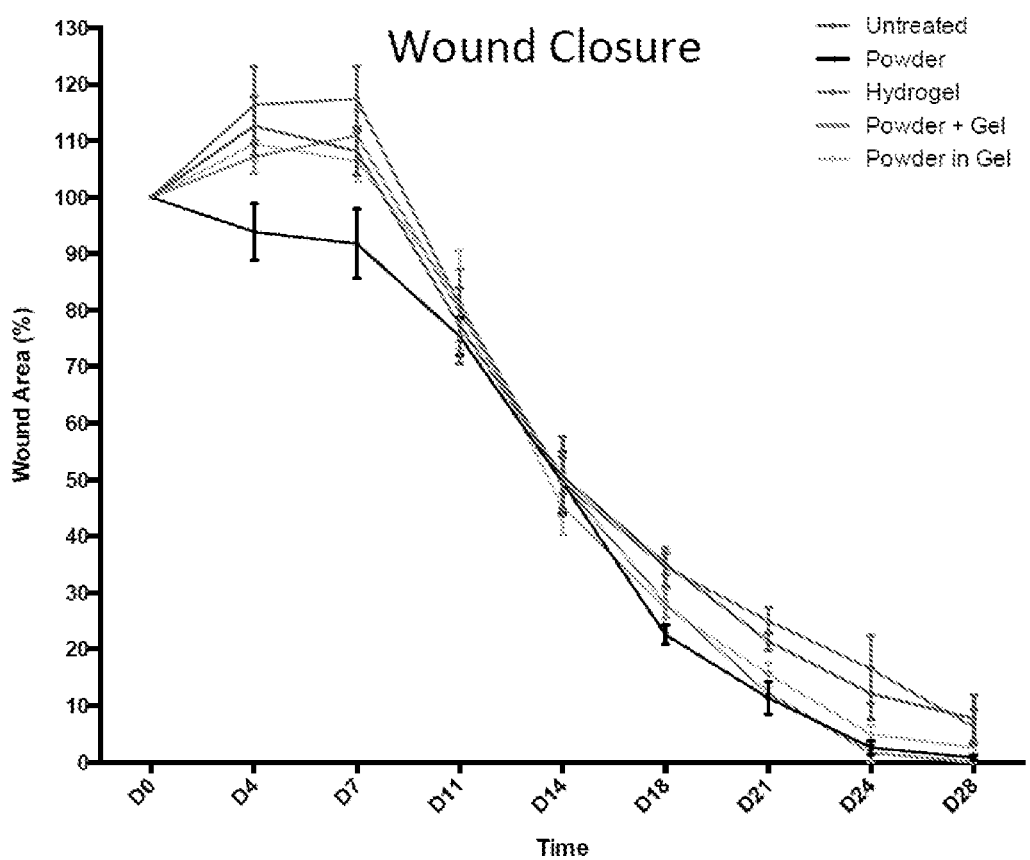
FIG. 35 is a graph illustrating wound closure over time.
Figure 48:
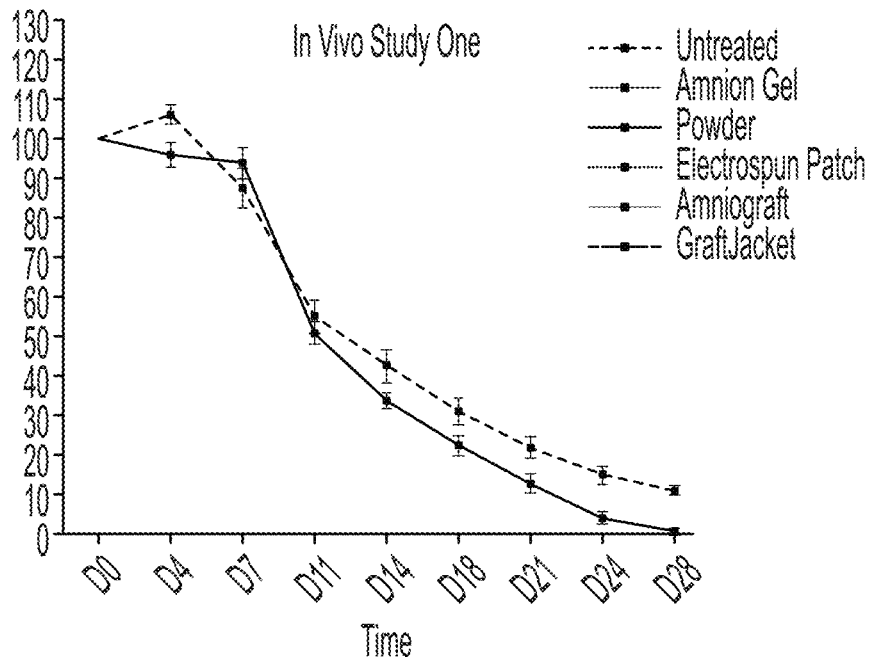
FIG. 48 illustrates wound contraction comparison results. Panel A illustrates the wound contraction among Untreated and Amnion Powder-treated groups in in vivo study one. Panel B illustrates the wound contraction among Untreated and Amnion Powder-treated groups in in vivo study two.
Figure 48:
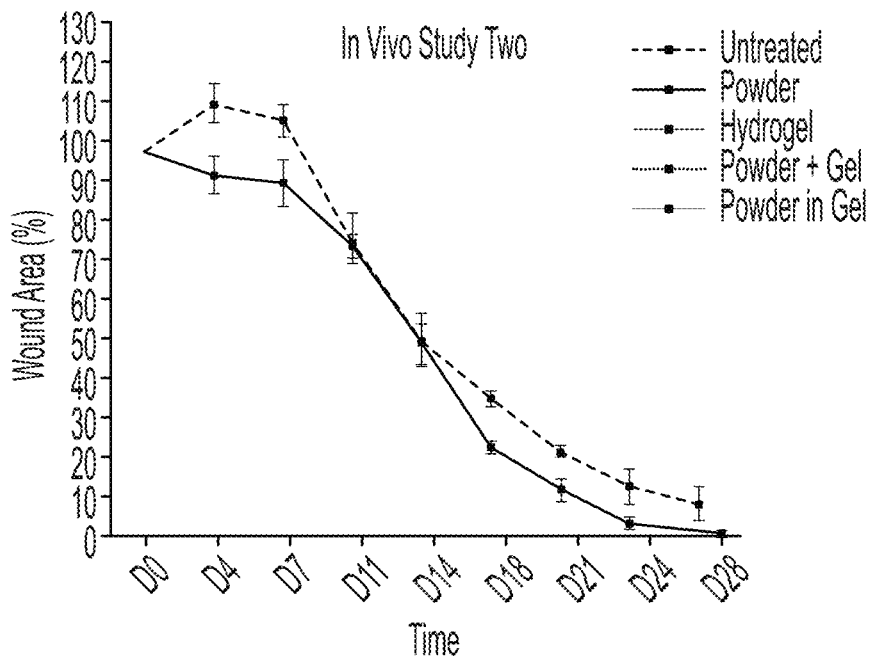

Wound Closure:

Wound closure correlates with successful wound healing. The higher the wound closure rate, the better the healing outcome. Wound closure was measured for each time-point and expressed as a percentage of the wound present as relative to the original wound area (FIG. 35). Average wound size was 17.5 $cm^2$ with no significant differences between treatments or pigs. In the immediate time-point following wound treatment there was an initial increase of the wound area for all wounds other than Amnion Powder-treated wounds due to wound stretching/drooping. This suggests that application of Amnion Powder helps to immediately stabilize the wound area. Untreated and Hydrogel-treated wounds showed the greatest expansion in wound size in the early time-points Amnion Powder-treated groups showed an earlier and more pronounced onset of granulation. This primarily occurred between Day 4 and Day 11 and occurred in every treatment formulation containing Amnion Powder. All groups showed a rapid decrease in wound area between Day 7 and Day 14, with all groups performing similarly during this period. However, between Day 14 and Day 28, the three Amnion Powder-treated groups showed accelerated wound closure, resulting in almost 100% closure by Day 24. At this point, Untreated and Hydrogel-treated wounds still showed approximately 15-20% wound area. This difference was observed at every time-point after Day 14. To compare outcomes between the two in vivo studies herein, replicate groups from each study (Untreated and Amnion Powder) were plotted and compared (FIG. 48). This comparison shows that although some minor differences were seen in the timing of wound expansion and contraction the trends and rate of wound closure was very similar, as was the improvement when powder was applied.

Figure 36:
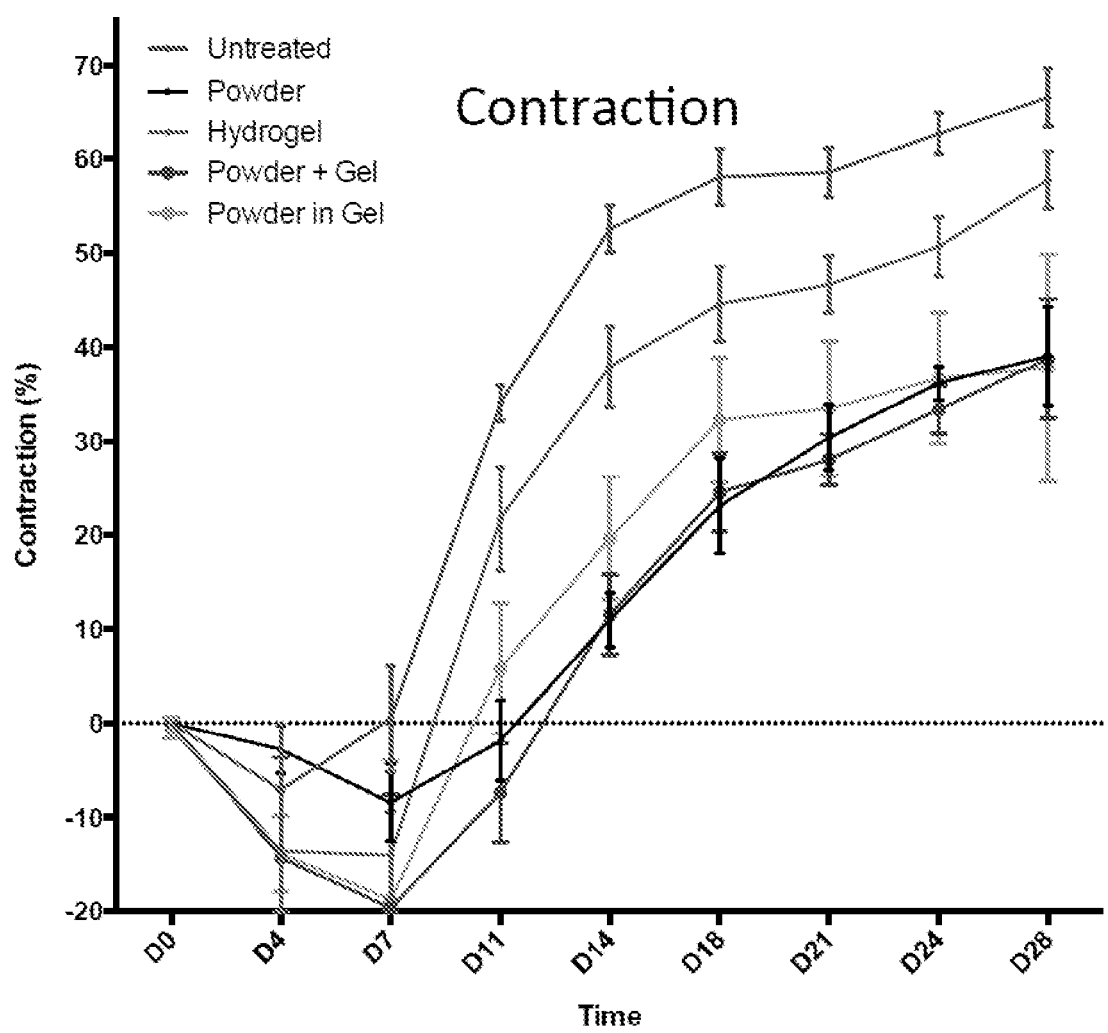
FIG. 36 is a graph illustrating the changes of wound contraction over time under different treatments.

Wound Contraction:

Wound contraction correlates with wound healing effectiveness. The higher the contraction rate was, the worse the healing outcome became. Wound contraction was measured for each time-point by measuring the area within the tattoo border and expressed as a percentage of the area relative to the original tattoo area (FIG. 36). As with the wound closure data, it was observed that an initial increase in the wound/tattoo area over the first 7 days. This resulted in an initial negative contraction percentage of approximately 20%. Untreated and Hydrogel-treated wounds showed the most contraction, with rapid contraction occurring between Day 7 and Day 14, reaching approximately 50% of the original tattoo area. At the final time-point these products showed 60% contraction. Amnion Powder, Powder+Gel and Powder in Gel contracted the least, with Powder and Powder+Gel performing the best. These products showed a delayed increase in contraction and a shorter and less rapid contraction period between Day 7 and Day 18 reaching a contraction of approximately 30%. At the final time-point these products showed 35% contraction.

Figure 37:
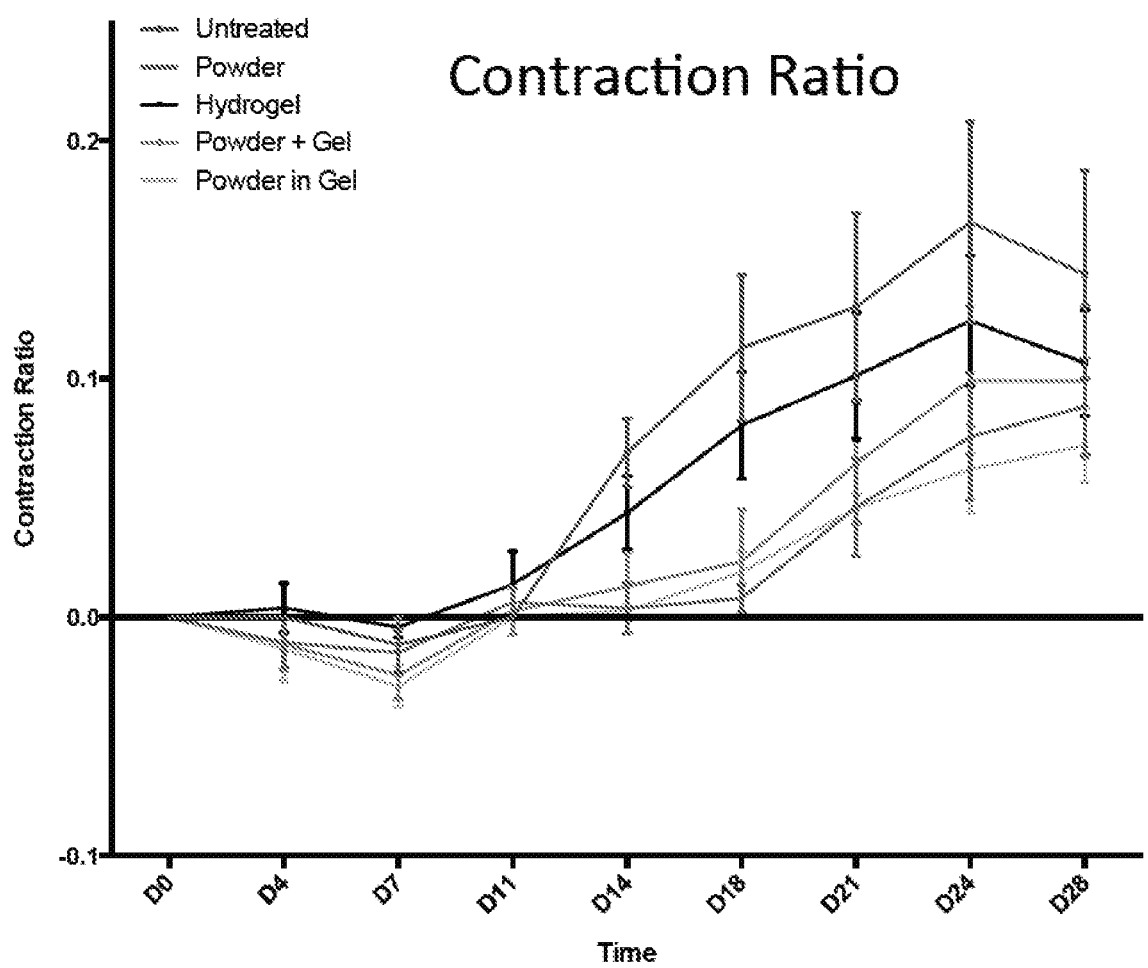
FIG. 37 is a graph illustrating the changes of wound contraction ratio over time under different treatments.

Wound Contraction Ratio:

To measure this phenomenon, several measurements of the wounds over all time-points were taken (FIG. 37). The distance of the left edge of the wound to the center point between the two left wound corners was measured and expressed as a ratio of the total distance between these corners. This ratio gives an approximate description of the amount of wound shape change. Non-contracted square wounds have a ratio close to 0, while highly contracted 'star' shaped wounds have a ratio close to 0.2. Confirming contraction data, the ratio of Untreated and Hydrogel-treated wounds increased to approximately 0.15 over 28 days. All Amnion Powder-treated groups increased to a lesser extent, maintaining a ratio of less than 0.1 over the course of the study.

Figure 39:
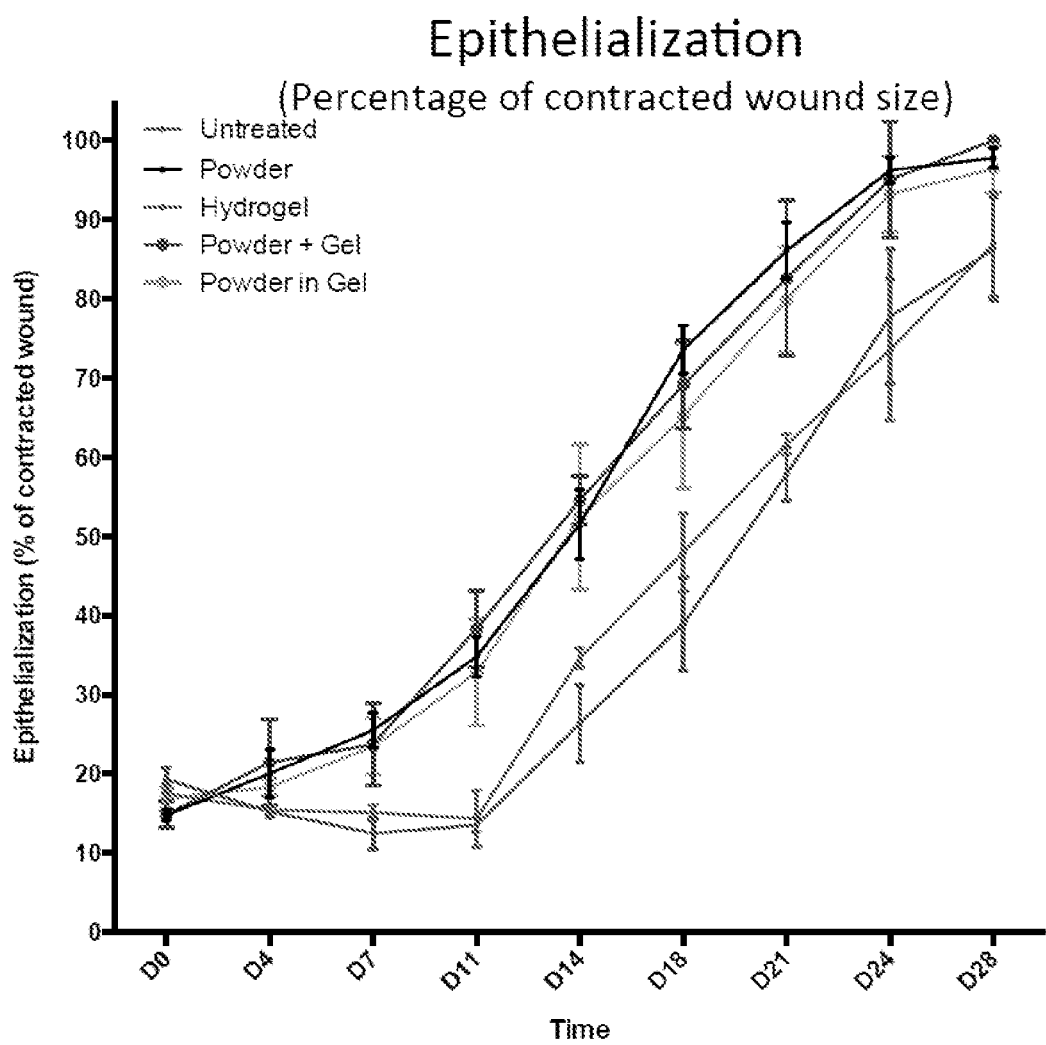
FIG. 39 is a graph illustrating percentage of contracted wound size over time under different treatments.

Wound Epithelialization:

Wound epithelialization correlates with wound healing success. The higher the epithelialization rate, the better the wound heals. Epithelialization was measured at all time-points by the presence of a matte appearing epithelial coating distinct from the wound area (FIG. 38). Epithelialization is described as the percentage of the original wound area covered by epithelium at each time-point. Therefore, the percentage of wound remaining, contraction and epithelialization should be approximately 100%. All tissues initially had some level of epithelialization due to the incisional wound being created inside the tattoo line. This initial area was approximately 18-20% of the area inside the tattoo and was consistent over all treatments and pigs. Untreated, and Hydrogel-treated wounds showed the least wound epithelialization, showing a very slow onset of epithelialization (0% increase until at Day 14-18) and a low total epithelialization (~25-30%) at the end of the study. Amnion Powder and Powder+Gel-treated wounds were the best performing for total wound epithelialization, showing a rapid initial epithelialization reaching approximately 45% by Day 14 and almost 70% by the end of the study. Amnion in Hydrogel showed slightly less epithelialization compared to the other two Amnion Powder-treated groups but was still significantly better than the Untreated and Hydrogel Groups. Wound epithelialization was also analyzed relative to the contracted wound area by dividing the area of wound epithelialization by the area of the contracted tattoo boundary (FIG. 39). This provides information of the wound composition within the boundaries of contraction and shows the wound closure as influenced by epithelialization.

Figure 40:
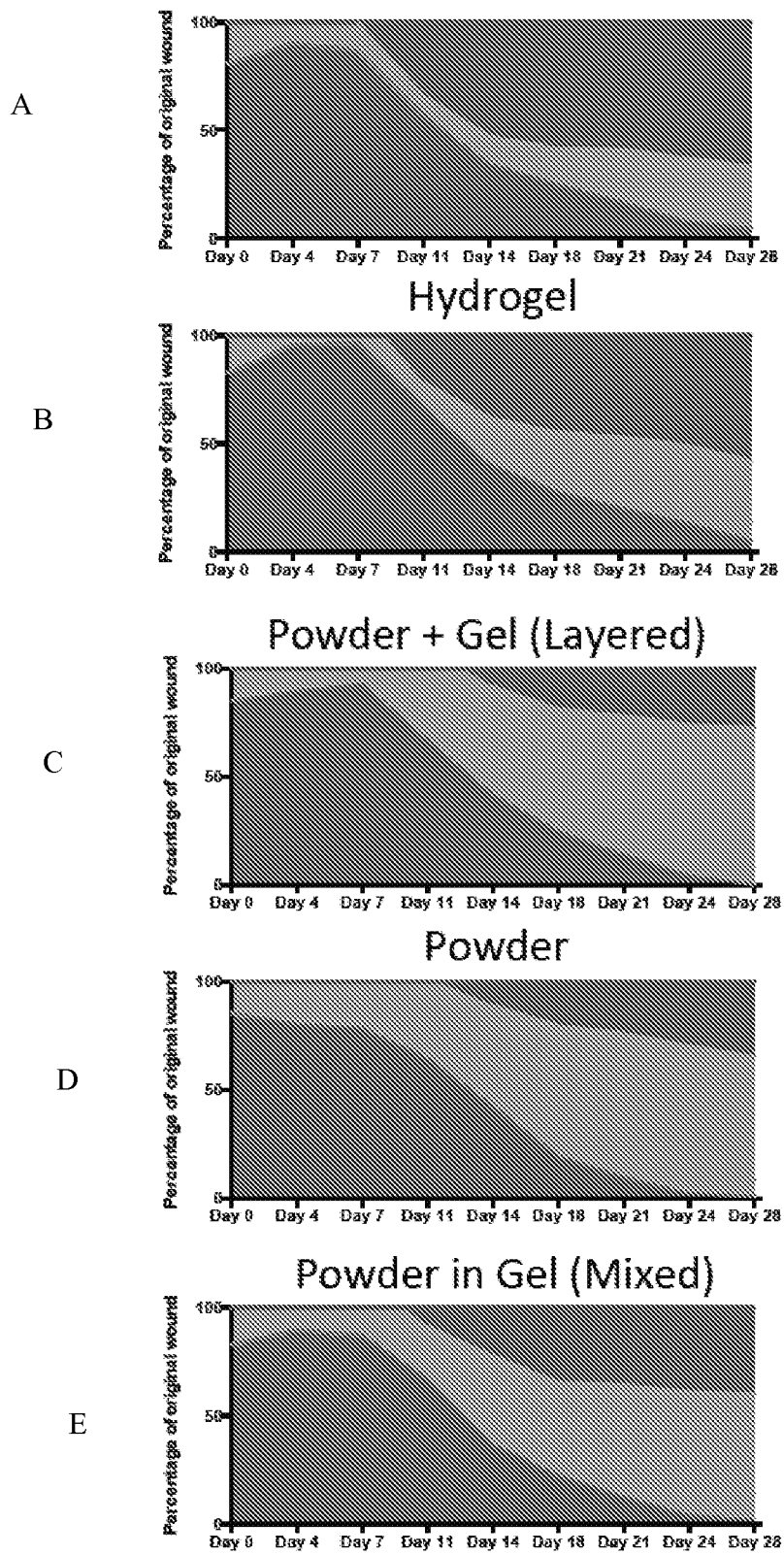
FIG. 40 illustrates the comparison wound healing result. Panel A illustrates a combination of wound size (red), epithelialization (green) and contraction areas (blue) of the wound area during healing when the wound was left untreated. Panel B illustrates a combination of wound size (red), epithelialization (green) and contraction areas (blue) of the wound area during healing when the wound was treated with hydrogel. Panel C illustrates a combination of wound size (red), epithelialization (green) and contraction areas (blue) of the wound area during healing when the wound was treated with Amnion Powder layered under hydrogel. Panel D illustrates a combination of wound size (red), epithelialization (green) and contraction areas (blue) of the wound area during healing when the wound was treated with Amnion Powder. Panel E illustrates a combination of wound size (red), epithelialization (green) and contraction areas (blue) of the wound area during healing when the wound was treated with Amnion Powder mixed with hydrogel.

Combined Analysis of Wound Area, Contraction and Epithelialization:

While important information can be gained from analyzing individual components of wound healing mechanisms, it is only by looking at the complete picture of the wound during healing that an accurate representation of the quality of healing can be obtained. To achieve this, the total wound area is represented at each time-point divided into the percentage of wound area, percentage contraction and percentage epithelialization (FIG. 40). With these three measured components fully describing the healing wound over time, the competing mechanisms of contraction and epithelialization for each of treatments can be observed. Ranking of each treatment was performed with the criteria for best healing as: small wound area, least contraction, and most epithelialization. Criteria for worst healing were; large wound area, most contraction, and least epithelialization. All three Amnion Powder-treated groups were the best performing products using these criteria, with the most rapid and complete closure of the wounds, which was driven by increased epithelialization and minimal contraction. In these groups contraction accounted for approximately 30% of wound closure, while 70% was driven by epithelialization by the end of the study. Untreated and Hydrogel-treated groups were the worst performing, showing 60-70% contraction, 20-30% epithelialization and 10% open wound remaining by the end of the study. These data highlight the importance of the type and quality of wound healing, as contraction may result in a decrease in wound area, but also leads to disfigurement, scarring and loss of function. For this reason, wound closure by re-epithelialization is most desirable as this results in a rapid restoration of the skin barrier, with optimal cosmetic and functional outcomes.

Histological Analysis

Figure 41:
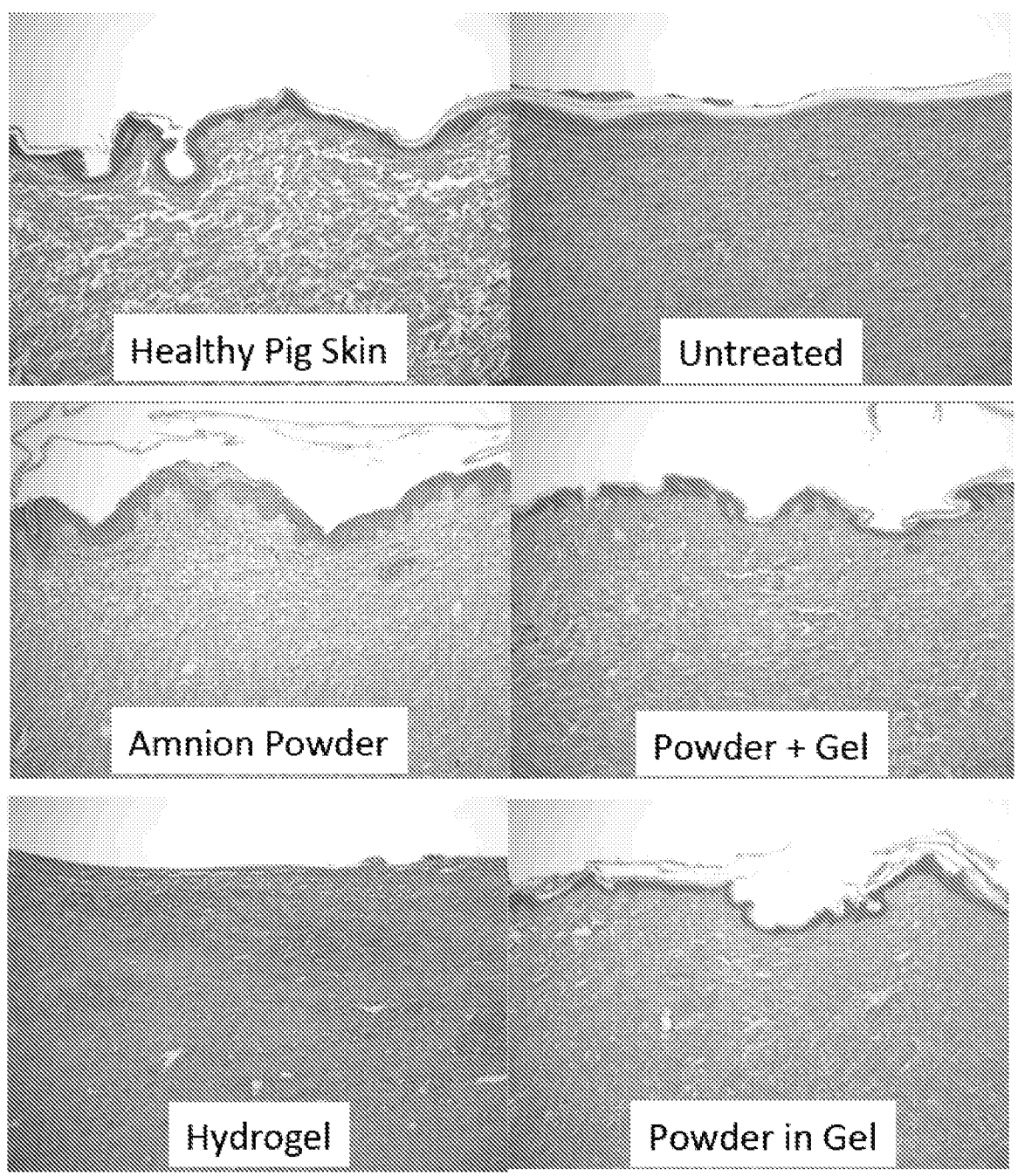
FIG. 41 is a set of images illustrating representative Hematoxylin and Eosin (H&E) stained histological images for pigs 7, 8, and 9.

Hematoxylin and Eosin stained sections were used to evaluate and compare the general structure and composition of each of the wounds. Representative images from pigs 7-9 are shown in FIG. 41. Healthy pig skin was used as a control for this analysis. Analysis of wounds from pigs 7-9 showed that the epidermis from Amnion Powder, Amnion+Gel and Amnion in Gel-treated wounds looked similar to healthy skin in regards to the epidermis coverage, thickness and presence of rete pegs. The epidermis of Untreated and Hydrogel-treated wounds was not always present, but when it was it appeared thin and immature, lacking a defined boundary with the dermis and lacking rete pegs. The dermis of healthy skin consisted of large organized fibers that were light pink in color, with only minimal disorganized, thin, purple fibers. Amnion Powder, Amnion+Gel and Amnion in Gel-treated wounds looked similar to healthy skin, with similar composition including large organized dermal fibers intertwines with smaller fibers. Untreated and Hydrogel-treated wounds showed a dense network of small dark fibers and hypertrophic cells. Overall, all Amnion Powder-treated groups appeared most similar to healthy skin in regards to both the epidermis and dermis.

Figure 42:
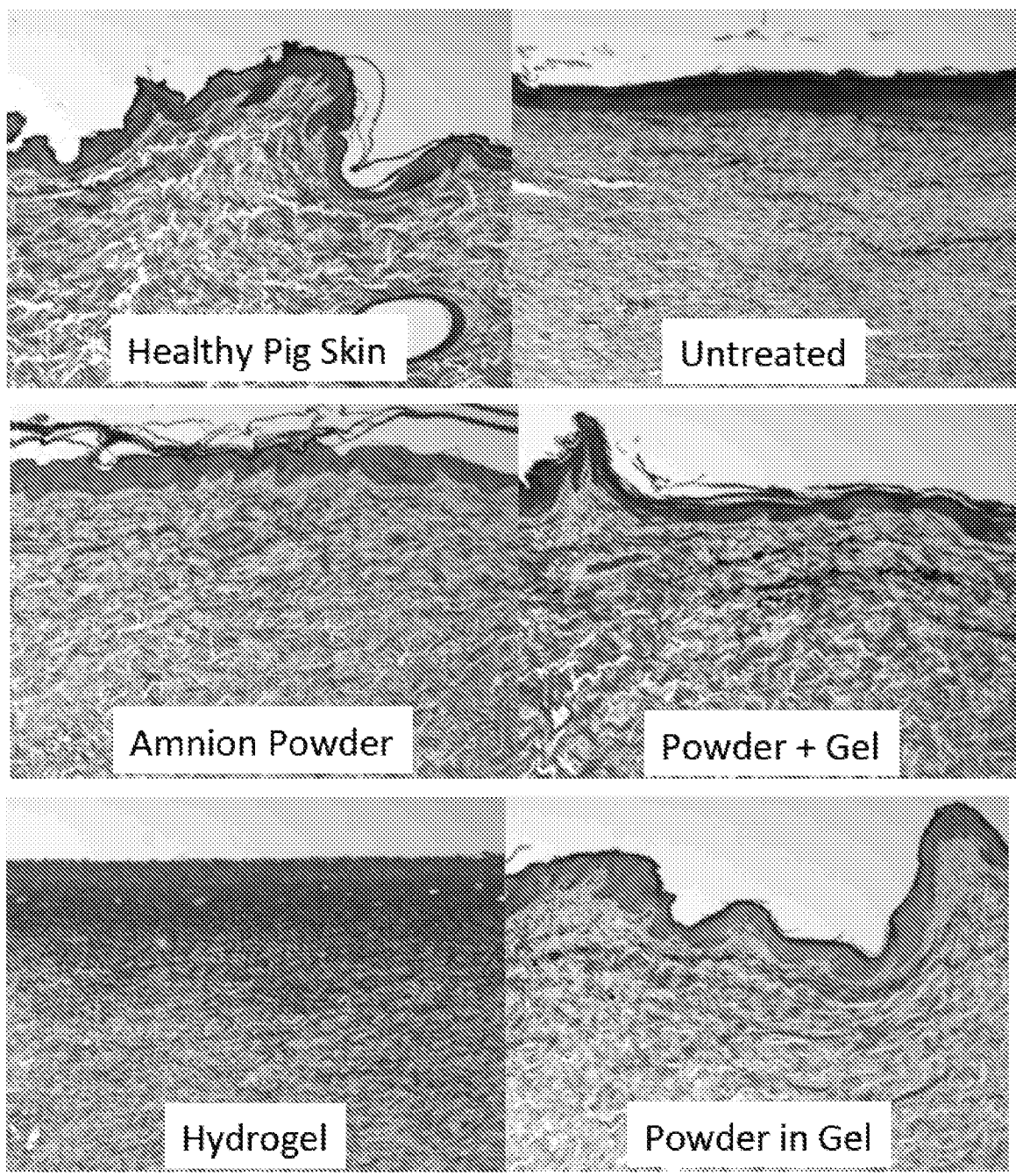
FIG. 42 is a set of images illustrating representative Pentachrome staining of tissues under different treatments.

Pentachrome Staining:

Pentachrome straining was performed to give an overview of the extracellular matrix (ECM) composition of the wounds. Pentachrome is a stain that is able to identify multiple ECM components simultaneously. Pentachrome staining shows in collagen in yellow, mature fibers in red, mucins and glycosaminoglycans (GAGs) in blue/green, and nuclei and elastic fibers in black. FIG. 42 shows the representative images of the 5 treatment groups and healthy skin. Healthy skin had a dermis that consisted of thick mature collagen fibers (red) and positive yellow and green staining for collagen and mucins/GAGs. Some black elastin staining was also observed in the upper dermis. Amnion Powder, Amnion+Gel and Amnion in Gel-treated wounds looked similar to healthy skin, with an intermediate amount of thick mature collagen fibers (red) on a yellow/green background of collagen, mucins and GAGs. Elastin fibers were also observed to a varying degree in all Amnion Powder-treated groups. Untreated wounds were primarily immature collagen fibers (yellow) with some GAG/mucin staining (blue). Very little mature collagen staining was observed. Hydrogel-treated wounds showed some staining for mature collagen, however this was not obvious and the fibers still appeared small and unorganized. Both Untreated and Hydrogel-treated wounds showed cellular hypertrophy.

Figure 43:
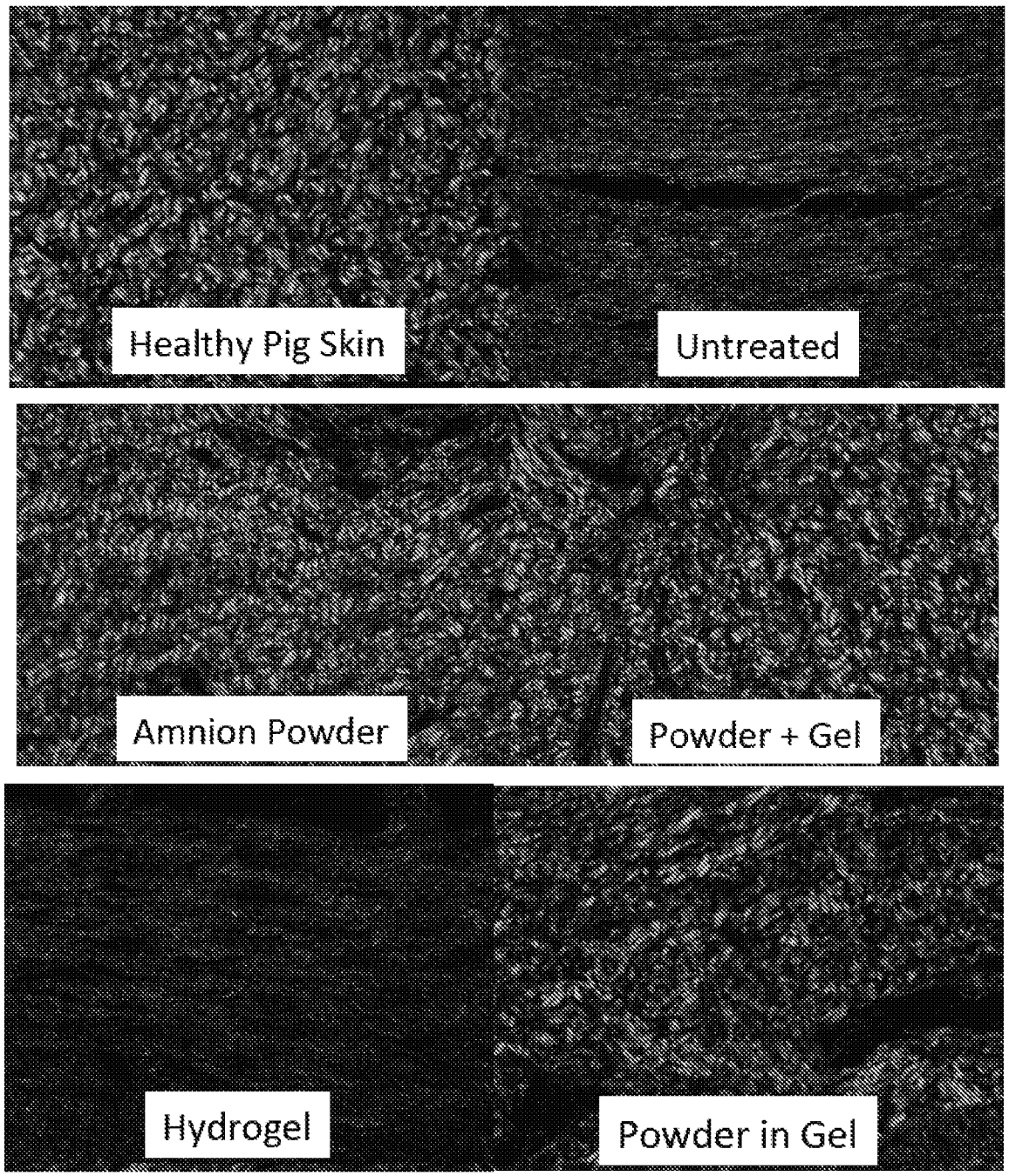
FIG. 43 is a set of images illustrating representative Sirius Red staining of tissues viewed with polarizing light.

Sirius Red Staining for Immature and Mature Collagen:

Sirius Red staining differentiates between immature and mature collagen when viewed under polarized light Immature unorganized collagen stains green and mature organized collagen stains yellow/orange. FIG. 43 shows the representative images of the 5 treatment groups and healthy skin. Healthy skin shows a strong staining of both green and orange, indicating an organized network of larger mature collagen fibers with smaller collagen fibers intermixed. All Amnion Powder treated-groups appear similar to the healthy skin, showing a similar distribution of orange and green throughout the dermis. Untreated and Hydrogel-treated groups showed minimal collagen staining, with only a small amount of mature (red) collagen visible.

Compressive Strength

Figure 46:
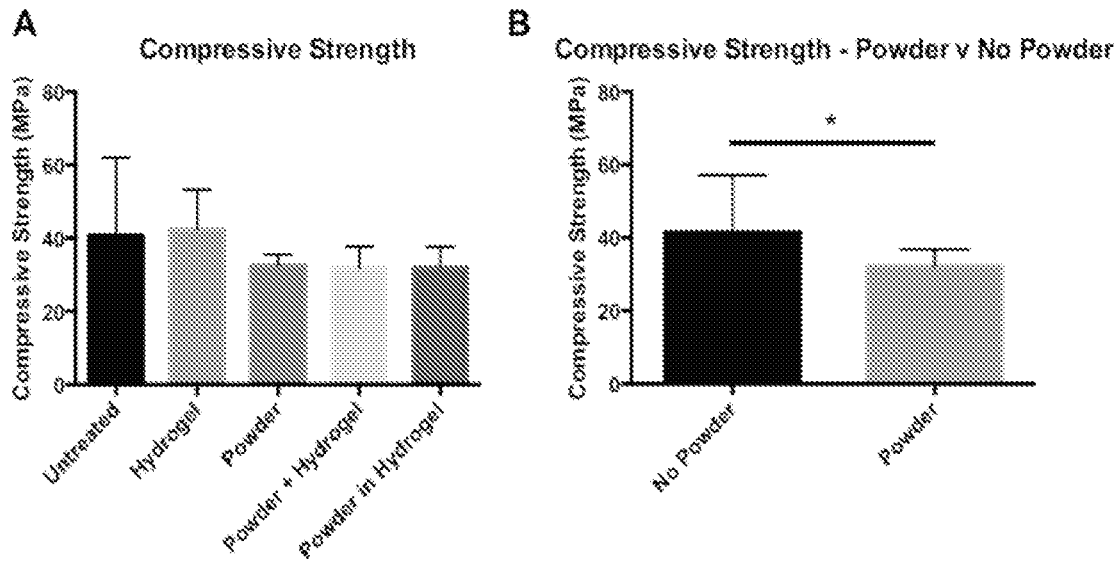
FIG. 46 illustrates the effects of Amnion Powder on skin compressive strength. Panel A illustrates maximum compressive strength of the regenerated skin samples from the 5 experimental conditions. Panel B illustrates maximum compressive strength of compiled groups without Amnion Powder and with Amnion Powder (p<0.05).

Compressive strength was measured to be generally higher in the Untreated and Hydrogel groups (40.72 and 42.35 MPa respectively) in comparison to the Powder, Powder+Hydrogel, and Powder in Hydrogel groups (32.69, 31.93, and 32.01 MPa respectively; FIG. 46A). Although, these differences were not significantly different, they show a consistent trend in that inclusion of Amnion Powder reduced compressive strength. In fact, if Untreated and Hydrogel experimental values are combined and all the Powder-including groups are combined, then the inclusion of Amnion Powder reduces compressive stress significantly (41.54 vs 32.21 MPa, respectively; $p<0.05$) (FIG. 46B).

Young's Modulus

Young's modulus was lowest in the Untreated group (9.78 MPa). The other groups—Hydrogel, Powder, Powder+Hydrogel, and Powder in Hydrogel—had higher Young's moduli of 11.10, 12.84, 10.07, and 11.62 MPa, respectively. None of the differences observed were statistically significant (FIG. 47A).

Yield Point

Figure 47:
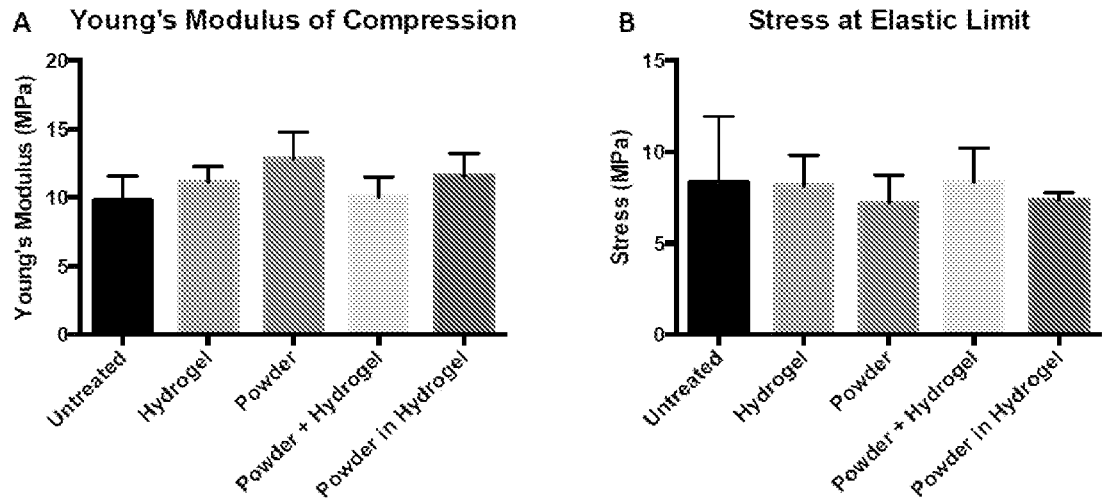
FIG. 47 illustrates the effects of Amnion Powder on skin Young's modulus. Panel A illustrates Young's modulus of the regenerated skin samples from the 5 experimental conditions. Panel B illustrates the stress at elastic limit under 5 experimental conditions.

No significant differences were found between any groups in terms of yield stress (FIG. 47B).

Summary

Ease of Treatment Administration:

Application of the modified hydrogel system required minimal preparation and only one hand for sterile application. This hydrogel system can be stored frozen in the ready-to-use duel chamber syringe. For application the product be simply thawed and applied.

Wound Healing Quality:

Analysis of wound closure, contraction and epithelialization demonstrated that all Amnion Powder—containing groups were superior in wound closure and epithelialization, and were the best performers in preventing contraction. Untreated and Hydrogel-treated wounds showed increased contraction, reduced epithelialization and slower wound closure time, with Hydrogel performing marginally better than untreated. Amnion Powder-containing treatments accelerated the rate and extent of total wound closure through the significant acceleration of wound re-epithelialization. A minimal difference was noted between the rate of epithelialization of the Powder in Hydrogel group compared to the other two Amnion groups. While the Amnion Powder and Amnion+Hydrogel treatments involved the application of the entire dose of powder onto the wound, diluting the Amnion Powder with the Hydrogel may have slightly delayed the release of bioactive factors to the wound bed, potentially also diluting the effect of the Amnion Powder at key time-points during wound healing.

Skin Quality:

Histological observations showed that all Amnion Powder-groups had a wound composition similar to healthy skin, consisting of similar epidermis coverage, thickness and presence of rete pegs and a dermis composition including large organized dermal fibers intertwines with smaller fibers. The quality of the wound ECM is of key importance to the long-term success of the healing wound. ECM composition has a major influence over the properties of healing wounds. Histological staining confirmed initial observations, showing that all Amnion Powder-treated groups had a dermal ECM composition consisting of thick mature collagen fibers intertwined with less immature collagen and staining for elastin fibers with localizations and staining intensities consistent with mature skin. In regards to dermal collagen composition, Sirius red staining showed that all Amnion Powder-treated groups had a similar ratio and composition of immature and mature collagen fibers within the dermis. Untreated and Hydrogel-treated wounds showed immature or absent epidermis, and a dermis composition of dense, immature and unorganized collagen fibers and cellular hyperplasia.

Compression Testing

Differences in compression testing were not statistically significant, for the most part. However, based on the overall trends, the combined No Powder vs. Powder compressive strength data, and histological examination of excised tissue samples, the data suggests that including amnion powder in treatments decreases compressive strength. Compressive strength represents the non-elastic component of tissue compression biomechanics and increased compressive strength means a reduced ability of the regenerated skin to deform and then elastically rebound. Therefore, this data suggests that at this point in the healing process, powder-treated groups are less rigid and more elastic. Furthermore, all combinations of hydrogel with or without amnion powder result in a higher Young's modulus that the untreated group. This may suggest that these treatments do indeed increase the elasticity of the regenerating skin. However, these tissues, from which measurements were taken at 28 days post-injury are likely too early in the regeneration process to be sufficient. It is possible that should the study occur for a longer duration of time, the differences in mechanical properties may yield statistical significance.

In conclusion, the Amnion Powder, Amnion Powder+Hydrogel (layered) and Amnion Powder in Hydrogel (mixed) were equally easy to administer to full thickness wounds and resulted in the most rapid wound closure rates, driven primarily by new epithelialization, and result in the formation of a mature epidermis and dermis with similar composition to healthy skin. These observations are consistent with the other in vivo study described herein and provide multiple options for the delivery of this product for clinical wound healing applications.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An amniotic membrane powder composition comprising an amount of total released protein in the range of 30 mg/g to 500 mg/g,
    wherein the composition further comprises a cross-linked hydrogel matrix;
    wherein the cross-linked hydrogel matrix comprises hyaluronic acid cross-linked to gelatin through a polyethylene glycol comprising crosslinker; and
    wherein the crosslinking occurs via maleimide-thiol bonds.

2. The composition of claim 1, wherein the total protein is in the range of 50 mg/g to 250 mg/g.

3. The composition of claim 1, further comprising an amount of elastin in the range of 4 mg/g to 100 mg/g.

4. The composition of claim 1, further comprising an amount of collagen in the range of 10 mg/g to 800 mg/g.

5. The composition of claim 1, further comprising an amount of glycosaminoglycans in the range of 0.1 mg/g to 5 mg/g.

6. The composition of claim 1, further comprising an amount of thrombospondin-1 (TSP-1) in the range of 30 µg/g to 1000 µg/g.

7. The composition of claim 1, further comprising an amount of pentraxin 3 (PTX-3) in the range of 0.1 µg/g to 50 µg/g.

8. The composition of claim 1, further comprising an amount of TSG-6 less than 1.5 ng/g.

9. The composition of claim 1, wherein the hydrogel comprises PEGDMal.

10. The composition of claim 1, wherein the scaffold comprises at least one synthetic polymer selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate.

11. The composition of claim 4, wherein the collagen is in the range of 10 mg/g to 600 mg/g.

12. An amniotic membrane powder composition comprising an amount of elastin in the range of 4 mg/g to 100 mg/g, wherein the composition further comprises a cross-linked hydrogel matrix,
    wherein the cross-linked hydrogel matrix comprises hyaluronic acid cross-linked to gelatin through a polyethylene glycol comprising crosslinker; and
    wherein the crosslinking occurs via maleimide-thiol bonds.

13. The composition of claim 12, wherein the elastin is in the range of 5 mg/g to 60 mg/g.

14. The composition of claim 12, further comprising an amount of collagen in the range of 10 mg/g to 800 mg/g.

15. The composition of claim 12, further comprising an amount of glycosaminoglycans in the range of 0.1 mg/g to 5 mg/g.

16. The composition of claim 12, further comprising an amount of thrombospondin-1 (TSP-1) in the range of 30 µg/g to 1000 µg/g.

17. The composition of claim 12, further comprising an amount of pentraxin 3 (PTX-3) in the range of 0.1 µg/g to 50 µg/g.

18. The composition of claim 12, further comprising an amount of TSG-6 less than 1.5 ng/g.

19. The composition of claim 14, wherein the collagen is in the range of 10 mg/g to 600 mg/g.

20. An amniotic membrane powder composition comprising total released protein in the range of 30 mg/g to 500 mg/g, elastin in the range of 4 mg/g to 100 mg/g, collagen in the range of 10 mg/g to 800 mg/g, and glycosaminoglycans in the range of 0.1 mg/g to 5 mg/g, wherein the composition further comprises a cross-linked hydrogel matrix,
    wherein the cross-linked hydrogel matrix comprises hyaluronic acid cross-linked to gelatin through a polyethylene glycol comprising crosslinker; and
    wherein the crosslinking occurs via maleimide-thiol bonds.

21. The composition of claim 20, further comprising an amount of thrombospondin-1 (TSP-1) in the range of 30 µg/g to 1,000 µg/g.

22. The composition of claim 20, further comprising an amount of pentraxin 3 (PTX-3) in the range of 0.1 µg/g to 50 µg/g.

23. The composition of claim 20, further comprising an amount of tumor necrosis factor-stimulated gene 6 (TSG-6) less than 1.5 ng/g.

24. An amniotic membrane powder composition comprising total released protein in the range of 30 mg/g to 500 mg/g, elastin in the range of 4 mg/g to 100 mg/g, collagen in the range of 10 mg/g to 800 mg/g, glycosaminoglycans in the range of 0.1 mg/g to 5 mg/g, thrombospondin-1 (TSP-1) in the range of 30 µg/g to 1,000 µg/g, pentraxin 3 (PTX-3) in the range of 0.1 µg/g to 50 µg/g, and tumor necrosis factor-stimulated gene 6 (TSG-6) less than 1.5 ng/g, wherein the composition further comprises a cross-linked hydrogel matrix,
- wherein the cross-linked hydrogel matrix comprises hyaluronic acid cross-linked to gelatin through a polyethylene glycol comprising crosslinker; and
- wherein the crosslinking occurs via maleimide-thiol bonds.

25. A method of inducing wound healing and tissue regeneration in a subject comprising administering the amniotic membrane powder composition of claim 1 to a treatment site in the subject.

\* \* \* \* \*